US012754171B2

(12) United States Patent
Zhou et al.

(10) Patent No.: US 12,754,171 B2
(45) Date of Patent: Oct. 6, 2026

(54) ANALYSIS DEVICE AND ANALYSIS METHOD FOR QUALITY INDEX OF NATURAL GAS PRODUCT AND APPLICATION

(71) Applicant: PETROCHINA COMPANY LIMITED, Beijing (CN)

(72) Inventors: Li Zhou, Beijing (CN); Xiaoqin Wang, Beijing (CN); Wenping Zeng, Beijing (CN); Lin Shen, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 193 days.

(21) Appl. No.: 18/761,191

(22) Filed: Jul. 1, 2024

(65) Prior Publication Data

US 2024/0353378 A1 Oct. 24, 2024

Related U.S. Application Data

(63) Continuation of application No. PCT/CN2022/102440, filed on Jun. 29, 2022.

(30) Foreign Application Priority Data

Dec. 31, 2021 (CN) ........................ 202111675665.9

(51) Int. Cl.
*G01N 30/20* (2006.01)
*B01D 15/08* (2006.01)
(Continued)

(52) U.S. Cl.
CPC ............. *G01N 30/20* (2013.01); *B01D 15/08* (2013.01); *B01D 53/025* (2013.01); *G01N 30/14* (2013.01);
(Continued)

(58) Field of Classification Search
CPC ........ G01N 30/02; G01N 30/06; G01N 30/88; G01N 2030/027; G01N 30/34;
(Continued)

(56) References Cited

U.S. PATENT DOCUMENTS 4,234,315 A * 11/1980 Scott ...................... G01N 31/12 436/115
5,069,690 A * 12/1991 Henderson ................ C01B 9/08 95/902
(Continued)

FOREIGN PATENT DOCUMENTS

CA 2780637 A1 * 5/2011 ......... B01D 53/0462
CN 2585232 Y 11/2003
(Continued)

OTHER PUBLICATIONS

Grant-Decision issued on Jan. 9, 2025, in Russian Application No. 2024118604.

(Continued)

*Primary Examiner* — Andre J Allen
(74) *Attorney, Agent, or Firm* — Meunier Carlin & Curfman LLC

(57) ABSTRACT

The present invention provides a device and method for analyzing quality indicators of a natural gas product and an application. The device comprises a sample loading assembly, and first, second, third, fourth, and fifth chromatographic column analysis systems connected in parallel, wherein the first chromatographic column analysis system is configured for separating sulfides from natural gas; the second chromatographic column analysis system is configured for separating hydrocarbons having $C_3$ and higher from the natural gas; the third chromatographic column analysis system is configured for separating oxygen, nitrogen, methane, and carbon monoxide from the natural gas; the fourth chromatographic column analysis system is configured for
(Continued)

separating carbon dioxide and ethane from the natural gas; and the fifth chromatographic column analysis system is configured for separating helium and hydrogen from the natural gas; each chromatographic column analysis system is provided with a quantitative tube, a carrier gas tube, and a chromatographic column.

20 Claims, 13 Drawing Sheets

(51) Int. Cl.

| | |
|---|---|
| ***B01D 53/02*** | (2006.01) |
| ***G01N 30/02*** | (2006.01) |
| ***G01N 30/14*** | (2006.01) |
| ***G01N 30/64*** | (2006.01) |
| ***G01N 30/74*** | (2006.01) |
| ***G01N 30/78*** | (2006.01) |
| ***G01N 33/00*** | (2006.01) |

(52) U.S. Cl.

CPC ............ *G01N 30/64* (2013.01); *G01N 30/74* (2013.01); *G01N 30/78* (2013.01); *G01N 33/0027* (2013.01); *B01D 2257/102* (2013.01); *B01D 2257/104* (2013.01); *B01D 2257/108* (2013.01); *B01D 2257/11* (2013.01); *B01D 2257/30* (2013.01); *B01D 2257/502* (2013.01); *B01D 2257/504* (2013.01); *B01D 2257/7025* (2013.01); *G01N 2030/025* (2013.01)

(58) Field of Classification Search

CPC .. G01N 30/74; G01N 30/32; G01N 2030/025; G01N 30/72; G01N 30/30; G01N 30/96; G01N 30/20; G01N 2030/062; G01N 30/56; G01N 30/90; G01N 2030/324; G01N 30/6004; G01N 30/24; G01N 30/60; G01N 30/14; G01N 30/7233; G01N 30/6095; G01N 30/461; G01N 30/16; G01N 30/6026; G01N 33/558; G01N 30/6017; G01N 30/463; G01N 30/8679; G01N 30/6052; G01N 30/38; G01N 30/466; G01N 30/6021; G01N 2030/326; G01N 30/8675; G01N 30/603; G01N 30/6047; G01N 30/6091; G01N 30/8658; G01N 2030/884; G01N 2030/201; G01N 30/36; G01N 30/54; G01N 2030/8831; G01N 30/7266; G01N 2030/202; G01N 2030/047; G01N 30/12; G01N 30/7206; G01N 2030/8813; G01N 30/468; G01N 2030/565; G01N 30/86; G01N 30/94; G01N 2030/965; G01N 30/6039; G01N 30/8631; G01N 30/64; G01N 2030/8804; G01N 30/08; G01N 30/50; G01N 30/68; G01N 2030/522; G01N 30/52; G01N 2030/045; G01N 33/6848; G01N 2030/067; G01N 30/465; G01N 2030/3007; G01N 2030/085; G01N 30/04; G01N 2030/562; G01N 30/84; G01N 30/8634; G01N 30/42; G01N 30/62; G01N 2030/8881; G01N 30/95; G01N 30/6069; G01N 30/8693; G01N 2030/207; G01N 2030/347; G01N 30/89; G01N 30/26; G01N 30/78; G01N 30/46; G01N 2030/146; G01N 30/82; G01N 2030/065; G01N 30/8686; G01N 33/54388; G01N 30/6034; G01N 30/606; G01N 30/80; G01N 2030/328; G01N 2030/889; G01N 2030/3084; G01N 30/22; G01N 2030/8809; G01N 30/18; G01N 30/8665; G01N 2030/528; G01N 30/00; G01N 2030/042; G01N 33/577; G01N 30/10; G01N 30/6043; G01N 30/92; G01N 30/28; G01N 33/6854; G01N 35/1097; G01N 30/6078; G01N 2030/567; G01N 30/8651; G01N 2030/8854; G01N 30/40; G01N 33/533; G01N 30/93; G01N 33/543; G01N 30/6065; G01N 30/8624; G01N 2030/8822; G01N 2030/121; G01N 1/405; G01N 30/58; G01N 21/05; G01N 30/462; G01N 33/531; G01N 33/6803; G01N 30/6082; G01N 30/91; G01N 33/56983; G01N 30/8668; G01N 2030/524; G01N 30/44; G01N 2030/009; G01N 21/33; G01N 2030/3046; G01N 2030/385; G01N 33/68; G01N 2030/3076; G01N 2030/885; G01N 2030/3061; G01N 2030/525; G01N 33/538; G01N 33/54306; G01N 33/54313; G01N 2030/628; G01N 30/66; G01N 2030/8827; G01N 33/54393; G01N 30/8696; G01N 2030/623; G01N 2030/126; G01N 2030/6013; G01N 2030/626; G01N 33/54353; G01N 2030/386; G01N 2030/3015; G01N 2030/8886; G01N 2030/8872; G01N 1/40; G01N 2030/8836; G01N 2030/402; G01N 2030/527; G01N 33/54346; G01N 2030/122; G01N 33/54387; G01N 2030/645; G01N 2030/8877; G01N 2030/167; G01N 30/8617; G01N 1/34; G01N 2030/342; G01N 2030/746; G01N 2030/3053; G01N 33/582; G01N 33/532; G01N 2030/3023; G01N 30/8641; G01N 33/6851; G01N 2030/383; G01N 33/566; G01N 2030/127; G01N 2030/8417; G01N 33/2823; G01N 2030/125; G01N 2030/8411; G01N 33/5308; G01N 2030/3038; G01N 2030/381; G01N 27/62; G01N 33/28; G01N 2030/008; G01N 27/44747; G01N 30/467; G01N 33/15; G01N 2030/387; G01N 33/53; G01N 33/6845; G01N 33/54373; G01N 2030/128; G01N 1/28; G01N 2030/625; G01N 30/70; G01N 2030/642; G01N 2021/0346; G01N 21/8483; G01N 30/6073; G01N 21/6428; G01N 2560/00; G01N 30/6086; G01N 2030/285; G01N 30/8662; G01N 2030/143; G01N 21/78; G01N 21/64; G01N 30/8644; G01N 35/1095; G01N 27/66; G01N 2030/205; G01N 21/01; G01N 33/94; G01N 30/8637; G01N 35/10; G01N 33/587; G01N 1/44; G01N 2030/0095; G01N 30/8682; G01N 2001/2229; G01N 2030/945; G01N 33/02; G01N 35/00732; G01N 1/38; G01N 2030/322; G01N 2030/8494; G01N 33/442; G01N 2030/303; G01N 30/8606; G01N 2030/8435; G01N 1/4055; G01N 21/31; G01N 2030/906; G01N 2030/847; G01N 27/622; G01N 33/52; G01N 33/54366;

G01N 33/6893; G01N 33/6842; G01N 33/92; G01N 33/56911; G01N 2030/8818; G01N 33/545; G01N 33/58; G01N 2030/8859; G01N 30/8672; G01N 2030/208; G01N 2030/8429; G01N 27/44721; G01N 2030/405; G01N 33/6806; G01N 35/00623; G01N 2030/185; G01N 2030/587; G01N 21/6486; G01N 27/623; G01N 33/54386; G01N 21/6402; G01N 27/447; G01N 2030/521; G01N 2030/6008; G01N 21/65; G01N 27/626; G01N 27/64; G01N 2030/8868; G01N 33/585; G01N 2440/38; G01N 33/44; G01N 2030/165; G01N 21/85; G01N 1/2214; G01N 21/658; G01N 35/0099; G01N 35/1004; G01N 1/14; G01N 27/624; G01N 33/493; G01N 35/04; G01N 2001/4061; G01N 2035/00495; G01N 30/7273; G01N 30/8603; G01N 30/724; G01N 33/54326; G01N 21/53; G01N 33/74; G01N 2030/388; G01N 27/22; G01N 35/1011; G01N 21/4133; G01N 35/1079; G01N 2035/0441; G01N 2469/10; G01N 30/8689; G01N 2030/407; G01N 2035/00524; G01N 33/721; G01N 1/22; G01N 33/00; G01N 33/497; G01N 33/743; G01N 33/82; G01N 30/7253; G01N 33/723; G01N 35/028; G01N 2030/123; G01N 33/5302; G01N 2013/006; G01N 2030/8423; G01N 2333/11; G01N 2469/20; G01N 33/56916; G01N 35/00; G01N 33/50; G01N 33/553; G01N 2030/8447; G01N 2030/8845; G01N 21/359; G01N 33/72; G01N 21/3504; G01N 21/645; G01N 2333/165; G01N 33/6809; G01N 15/0205; G01N 33/573; G01N 21/6408; G01N 27/44717; G01N 27/4473; G01N 33/48; G01N 33/588; G01N 35/00584; G01N 2030/8405; G01N 33/2829; G01N 1/4077; G01N 21/84; G01N 2800/52; G01N 30/278; G01N 35/025; G01N 2030/022; G01N 2030/445; G01N 2001/4033; G01N 2021/6439; G01N 2030/3069; G01N 2030/582; G01N 21/25; G01N 21/47; G01N 2400/00; G01N 30/76; G01N 33/80; G01N 2030/77; G01N 2570/00; G01N 30/8627; G01N 15/02; G01N 15/075; G01N 30/7213; G01N 2030/8441; G01N 21/03; G01N 21/76; G01N 31/12; G01N 33/564; G01N 35/109; G01N 2035/00198; G01N 21/07; G01N 2333/4737; G01N 33/76; G01N 2001/4088; G01N 2030/621; G01N 2333/805; G01N 24/08; G01N 35/1009; G01N 1/4044; G01N 2030/0035; G01N 27/18; G01N 33/2835; G01N 1/286; G01N 2035/00435; G01N 2035/1025; G01N 30/7246; G01N 33/548; G01N 33/96; G01N 35/00871; G01N 35/1016; G01N 2030/743; G01N 2035/00752; G01N 27/26; G01N 27/30; G01N 27/44743; G01N 31/22; G01N 33/0047; G01N 33/24; G01N 33/689; G01N 2035/103; G01N 21/3577; G01N 21/39; G01N 2333/31; G01N 27/226; G01N 27/44704; G01N 27/44756; G01N 2035/0484; G01N 2291/021; G01N 2333/015; G01N 33/552; G01N 33/56933; G01N 33/66; G01N 21/643; G01N 27/221; G01N 30/7293; G01N 30/861; G01N 33/241; G01N 33/491; G01N 33/544; G01N 35/0092; G01N 35/026; G01N 1/2273; G01N 2030/7226; G01N 2035/00326; G01N 21/255; G01N 21/41; G01N 2201/0221; G01N 27/4045; G01N 30/0005; G01N 33/5076; G01N 33/56944; G01N 2001/2893; G01N 2021/0112; G01N 2030/685; G01N 29/022; G01N 33/287; G01N 33/54333; G01N 1/2226; G01N 15/06; G01N 2001/4016; G01N 2035/0091; G01N 27/12; G01N 27/44795; G01N 29/0672; G01N 33/487; G01N 35/1065; G01N 1/10; G01N 21/73; G01N 2201/0621; G01N 23/046; G01N 2458/15; G01N 27/44791; G01N 33/569; G01N 33/56938; G01N 33/726; G01N 2035/00356; G01N 21/3581; G01N 21/45; G01N 2201/0693; G01N 2291/0256; G01N 2291/0426; G01N 27/301; G01N 33/535; G01N 33/542; G01N 33/56988; G01N 33/5758; G01N 33/686; G01N 33/9493; G01N 35/085; G01N 2001/4027; G01N 2021/3595; G01N 2030/862; G01N 2035/0439; G01N 2035/0444; G01N 2035/0465; G01N 21/67; G01N 22/00; G01N 2291/0423; G01N 23/04; G01N 2440/14; G01N 27/44752; G01N 30/722; G01N 33/0001; G01N 33/1826; G01N 33/5306; G01N 33/54391; G01N 33/6896; G01N 35/00009; G01N 1/18; G01N 1/24; G01N 15/0211; G01N 2015/0038; G01N 2035/0498; G01N 2201/08; G01N 2440/10; G01N 27/44773; G01N 27/70; G01N 2800/324; G01N 30/7286; G01N 33/5695; G01N 33/60; G01N 33/78; G01N 1/02; G01N 11/04; G01N 2201/0321; G01N 2021/0357; G01N 2035/00554; G01N 2035/00782; G01N 21/72; G01N 21/86; G01N 2333/47; G01N 2333/976; G01N 25/147; G01N 27/16; G01N 33/182; G01N 33/22; G01N 33/48735; G01N 33/5008; G01N 11/08; G01N 2001/045; G01N 2021/6482; G01N 2021/7759; G01N 21/0332; G01N 21/6458; G01N 27/4166; G01N 2800/042; G01N 31/16; G01N 33/0062; G01N 33/6857; G01N 35/08; G01N 1/00; G01N 1/2202; G01N 1/26; G01N 13/00; G01N 15/08; G01N 2035/041; G01N 2035/1053; G01N 21/3103; G01N 21/35; G01N 21/59; G01N 2201/0627; G01N 2333/35; G01N 25/18; G01N 27/00; G01N 27/06; G01N 27/14; G01N 2800/348; G01N 30/726; G01N 33/12; G01N 33/49; G01N 33/536; G01N 33/559; G01N 33/9446; G01N 1/4022;

G01N 2001/383; G01N 2001/4083; G01N 2021/335; G01N 2030/3092; G01N 2030/647; G01N 2030/8452; G01N 2030/8476; G01N 2030/903; G01N 2035/00564; G01N 2035/00851; G01N 2035/1037; G01N 21/0303; G01N 21/09; G01N 21/274; G01N 21/631; G01N 2333/4716; G01N 31/005; G01N 33/0098; G01N 33/025; G01N 33/225; G01N 33/54389; G01N 33/571; G01N 35/1002; G01N 5/04; G01N 2021/6432; G01N 2035/00792; G01N 2035/00811; G01N 2035/1032; G01N 2035/1046; G01N 2201/129; G01N 2333/08; G01N 2333/195; G01N 2333/20; G01N 2496/00; G01N 25/04; G01N 31/00; G01N 33/0004; G01N 33/0027; G01N 33/521; G01N 33/5764; G01N 33/581; G01N 35/00722; G01N 15/01; G01N 2021/6417; G01N 2030/8648; G01N 2035/00772; G01N 21/82; G01N 2223/419; G01N 2291/0289; G01N 23/2258; G01N 2333/415; G01N 2400/40; G01N 2600/00; G01N 2800/50; G01N 33/0009; G01N 33/0011; G01N 33/0019; G01N 33/0032; G01N 33/0034; G01N 33/2811; G01N 33/2882; G01N 33/6827; G01N 33/6887; G01N 2001/2873; G01N 2021/6467; G01N 2021/8488; G01N 2030/162; G01N 2030/8863; G01N 2035/00158; G01N 2035/0429; G01N 2035/0491; G01N 2035/1027; G01N 21/49; G01N 21/77; G01N 2201/061; G01N 2201/062; G01N 2333/162; G01N 2333/38; G01N 2333/59; G01N 27/041; G01N 27/423; G01N 1/4005; G01N 2021/052; G01N 2021/3181; G01N 2035/00346; G01N 2035/00514; G01N 2035/00762; G01N 2035/00801; G01N 21/6456; G01N 2201/1242; G01N 2333/005; G01N 2333/37; G01N 2430/00; G01N 25/14; G01N 2800/04; G01N 2800/085; G01N 2800/7028; G01N 31/10; G01N 33/0031; G01N 33/14; G01N 33/4977; G01N 33/6812; G01N 33/9406; G01N 35/00693; G01N 1/42; G01N 11/00; G01N 15/0625; G01N 2015/0687; G01N 2021/1765; G01N 2021/7789; G01N 2035/00831; G01N 2035/0415; G01N 2035/042; G01N 2035/0422; G01N 21/00; G01N 21/031; G01N 21/11; G01N 21/1702; G01N 2333/916; G01N 27/04; G01N 2800/28; G01N 29/44; G01N 30/8655; G01N 31/168; G01N 33/0014; G01N 33/184; G01N 33/48707; G01N 33/5002; G01N 33/5085; G01N 33/5434; G01N 33/56961; G01N 33/6818; G01N 35/00712; G01N 35/1081; G01N 1/2813; G01N 2001/028; G01N 2021/1787; G01N 2035/00108; G01N 2035/0475; G01N 2035/0477; G01N 2035/106; G01N 21/4795; G01N 2333/075; G01N 2333/09; G01N 2333/255; G01N 2333/4712; G01N 2333/4725; G01N 2333/70596; G01N 2333/924; G01N 2400/10; G01N 2470/04; G01N 2496/80; G01N 2500/00; G01N 27/02; G01N 27/07; G01N 27/44769; G01N 2800/065; G01N 33/10; G01N 33/18; G01N 33/188; G01N 33/523; G01N 33/526; G01N 33/5304; G01N 33/56972; G01N 33/56994; G01N 33/6869; G01N 1/04; G01N 15/00; G01N 15/0826; G01N 2001/1463; G01N 2011/0026; G01N 2013/003; G01N 2015/0216; G01N 2021/8887; G01N 2035/00881; G01N 2035/0093; G01N 2035/0418; G01N 2035/0453; G01N 2035/1051; G01N 21/15; G01N 21/171; G01N 21/23; G01N 21/27; G01N 21/314; G01N 21/3563; G01N 21/3586; G01N 21/453; G01N 21/4788; G01N 21/5911; G01N 21/766; G01N 21/8851; G01N 2201/0642; G01N 2201/068; G01N 2333/01; G01N 2333/135; G01N 2333/245; G01N 2333/4709; G01N 2333/4719; G01N 2333/4724; G01N 2333/585; G01N 2333/7051; G01N 2333/70517; G01N 2333/918; G01N 24/087; G01N 25/72; G01N 2500/10; G01N 27/045; G01N 2800/2821; G01N 2800/60; G01N 33/04; G01N 33/146; G01N 33/2805; G01N 33/48714; G01N 33/56966; G01N 33/57515; G01N 33/86; G01N 33/9486; G01N 1/2205; G01N 15/082; G01N 2001/002; G01N 2021/151; G01N 2030/765; G01N 2035/00306; G01N 2035/00445; G01N 2035/1058; G01N 2035/1088; G01N 21/21; G01N 21/4738; G01N 21/553; G01N 21/63; G01N 21/71; G01N 2223/03; G01N 2333/315; G01N 2333/575; G01N 2333/65; G01N 2470/10; G01N 2474/00; G01N 27/08; G01N 27/10; G01N 27/453; G01N 3/02; G01N 33/5005; G01N 33/5436; G01N 33/5438; G01N 33/551; G01N 33/57525; G01N 33/6824; G01N 33/9413; G01N 35/0098; G01N 15/1023; G01N 2001/2866; G01N 2001/4011; G01N 2015/0288; G01N 2015/1028; G01N 2201/1793; G01N 2021/6463; G01N 2021/6484; G01N 2035/00277; G01N 2035/1055; G01N 21/0317; G01N 21/43; G01N 21/51; G01N 21/69; G01N 2201/064; G01N 2201/124; G01N 2333/16; G01N 2458/40; G01N 27/185; G01N 27/228; G01N 27/24; G01N 27/302; G01N 27/308; G01N 27/44782; G01N 2800/36; G01N 2800/7095; G01N 29/02; G01N 29/032; G01N 29/069; G01N 33/0016; G01N 33/03; G01N 33/5097; G01N 33/537; G01N 33/6815; G01N 5/00; G01N 1/2035; G01N 1/2258; G01N 15/0806; G01N 2001/022; G01N 2001/1427; G01N 2001/205; G01N 2001/4066; G01N 2015/0046; G01N 2015/0846; G01N 2021/414; G01N 2021/5957; G01N 2021/6419; G01N 2021/6491; G01N 2021/7786; G01N

2030/001; G01N 2030/8895; G01N 2035/00237; G01N 2035/009; G01N 2035/102; G01N 2035/1069; G01N 21/17; G01N 21/19; G01N 21/251; G01N 21/552; G01N 21/718; G01N 2201/0668; G01N 2291/023; G01N 2291/0234; G01N 2333/23; G01N 2333/30; G01N 2333/42; G01N 2333/4731; G01N 2333/475; G01N 2333/61; G01N 2333/76; G01N 2333/79; G01N 2430/10; G01N 2440/00; G01N 2500/04; G01N 27/3272; G01N 27/416; G01N 27/44739; G01N 27/68; G01N 27/74; G01N 27/82; G01N 2800/26; G01N 2800/30; G01N 2800/347; G01N 33/0006; G01N 33/0022; G01N 33/0036; G01N 33/143; G01N 33/5011; G01N 33/525; G01N 33/539; G01N 33/575; G01N 33/57557; G01N 33/57565; G01N 33/5761; G01N 33/6821; G01N 33/84; G01N 33/88; G01N 33/946; G01N 35/1067; G01N 1/2211; G01N 1/2247; G01N 1/30; G01N 11/02; G01N 15/0272; G01N 15/0656; G01N 2001/387; G01N 2021/0367; G01N 2021/1706; G01N 2021/1736; G01N 2021/3129; G01N 2021/458; G01N 2021/6421; G01N 2021/6469; G01N 2021/651; G01N 2030/0015; G01N 2035/0493; G01N 21/61; G01N 21/648; G01N 21/75; G01N 21/763; G01N 21/8422; G01N 21/8806; G01N 2201/0639; G01N 2201/1293; G01N 2223/612; G01N 2291/018; G01N 2291/0231; G01N 2291/0232; G01N 2291/02809; G01N 2333/032; G01N 2333/14; G01N 2333/185; G01N 2333/285; G01N 2333/32; G01N 2333/43508; G01N 2333/45; G01N 2333/471; G01N 2333/525; G01N 2333/70539; G01N 2333/765; G01N 2333/78; G01N 2333/922; G01N 2333/986; G01N 2458/20; G01N 25/00; G01N 25/12; G01N 2500/02; G01N 27/38; G01N 27/403; G01N 27/44765; G01N 27/83; G01N 27/9006; G01N 2800/00; G01N 2800/044; G01N 2800/067; G01N 2800/12; G01N 2800/24; G01N 2800/368; G01N 2800/56; G01N 29/024; G01N 29/4454; G01N 29/4481; G01N 33/0013; G01N 33/0057; G01N 33/1846; G01N 33/26; G01N 33/5014; G01N 33/5038; G01N 33/5091; G01N 33/534; G01N 33/557; G01N 33/561; G01N 33/563; G01N 33/5752; G01N 33/5755; G01N 33/6866; G01N 33/6884; G01N 33/9453; G01N 33/9466; G01N 35/00594; G01N 35/02; G01N 7/14; G01N 13/02; G01N 15/1404; G01N 2001/021; G01N 2001/1006; G01N 2001/1031; G01N 2001/2217; G01N 2001/2223; G01N 2001/2261; G01N 2001/227; G01N 2001/242; G01N 2001/248; G01N 2001/288; G01N 2015/0011; G01N 2015/0053; G01N 2015/084; G01N 2021/0106; G01N 2021/115; G01N 2021/1714; G01N 2021/216; G01N 2021/4126; G01N 2021/4146; G01N 2021/4711; G01N 2021/641; G01N 2021/6478; G01N 2021/7753; G01N 2021/7796; G01N 2021/8466; G01N 2030/0025; G01N 2030/8458; G01N 2035/00386; G01N 2035/0094; G01N 2035/0406; G01N 2035/1039; G01N 21/29; G01N 21/474; G01N 21/55; G01N 21/68; G01N 21/7703; G01N 2201/0245; G01N 2201/0636; G01N 2201/0691; G01N 2223/04; G01N 2223/1013; G01N 2223/40; G01N 2223/401; G01N 2223/616; G01N 2291/015; G01N 2291/02827; G01N 2291/02854; G01N 2291/105; G01N 23/06; G01N 23/223; G01N 23/2251; G01N 2333/03; G01N 2333/13; G01N 2333/145; G01N 2333/205; G01N 2333/265; G01N 2333/28; G01N 2333/385; G01N 2333/405; G01N 2333/4713; G01N 2333/58; G01N 2333/605; G01N 2333/70535; G01N 2333/914; G01N 2333/98; G01N 2400/02; G01N 2405/08; G01N 2440/12; G01N 2440/20; G01N 27/123; G01N 27/3278; G01N 27/42; G01N 27/44786; G01N 27/49; G01N 27/9046; G01N 2800/06; G01N 2800/122; G01N 2800/2857; G01N 2800/2871; G01N 2800/321; G01N 2800/325; G01N 2800/38; G01N 29/036; G01N 29/04; G01N 29/045; G01N 29/0618; G01N 29/09; G01N 29/4427; G01N 29/4463; G01N 29/4472; G01N 29/449; G01N 31/002; G01N 31/164; G01N 33/0018; G01N 33/0026; G01N 33/0044; G01N 33/007; G01N 33/0096; G01N 33/1813; G01N 33/2888; G01N 33/34; G01N 33/445; G01N 33/46; G01N 33/4905; G01N 33/502; G01N 33/528; G01N 33/547; G01N 33/56977; G01N 33/5767; G01N 33/579; G01N 33/6863; G01N 33/6878; G01N 33/70; G01N 33/90; G01N 33/942; G01N 33/9433; G01N 33/9473; G01N 33/948; G01N 35/1072; G01N 5/02; G01N 7/00; G01N 9/32; G01N 1/20; G01N 1/32; G01N 15/04; G01N 15/042; G01N 15/065; G01N 15/088; G01N 15/10; G01N 15/1456; G01N 15/1459; G01N 17/00; G01N 2001/007; G01N 2001/027; G01N 2001/1418; G01N 2001/1436; G01N 2001/2057; G01N 2001/2244; G01N 2001/282; G01N 2001/386; G01N 2015/0092; G01N 2015/0294; G01N 2015/1493; G01N 2021/0307; G01N 2021/0328; G01N 2021/0382; G01N 2021/054; G01N 2021/152; G01N 2021/1738; G01N 2021/3155; G01N 2021/3159; G01N 2021/3572; G01N 2021/653; G01N 2021/775; G01N 2021/7793; G01N 2021/888; G01N 2030/0065; G01N 2030/382; G01N 2035/00148; G01N 2035/00178; G01N 2035/00247; G01N 2035/00376; G01N

2035/00465; G01N 2035/00534; G01N 2035/00544; G01N 2035/00633; G01N 2035/00673; G01N 2035/00891; G01N 2035/0405; G01N 2035/0451; G01N 2035/1018; G01N 21/253; G01N 21/3151; G01N 21/431; G01N 21/554; G01N 21/6404; G01N 21/6447; G01N 21/66; G01N 21/7746; G01N 21/783; G01N 21/896; G01N 21/94; G01N 21/95; G01N 22/02; G01N 2201/0225; G01N 2201/0624; G01N 2201/0633; G01N 2201/0638; G01N 2201/065; G01N 2201/066; G01N 2201/0695; G01N 2201/12; G01N 2201/121; G01N 2201/1296; G01N 2203/0682; G01N 2223/316; G01N 2223/3306; G01N 2291/011; G01N 2291/0215; G01N 2291/024; G01N 2291/02836; G01N 2291/0427; G01N 2291/048; G01N 2291/102; G01N 23/044; G01N 23/207; G01N 2333/085; G01N 2333/115; G01N 2333/175; G01N 2333/183; G01N 2333/25; G01N 2333/3156; G01N 2333/325; G01N 2333/44; G01N 2333/4613; G01N 2333/465; G01N 2333/4706; G01N 2333/4746; G01N 2333/54; G01N 2333/595; G01N 2333/62; G01N 2333/705; G01N 2333/7155; G01N 2333/7156; G01N 2333/775; G01N 2333/902; G01N 2333/904; G01N 2333/91085; G01N 2333/96413; G01N 2333/96416; G01N 2333/96466; G01N 2333/974; G01N 2333/978; G01N 2333/99; G01N 24/081; G01N 24/082; G01N 24/088; G01N 2400/18; G01N 2400/38; G01N 2400/50; G01N 2405/04; G01N 2410/00; G01N 2446/20; G01N 2446/40; G01N 2470/06; G01N 25/02; G01N 25/32; G01N 27/048; G01N 27/28; G01N 27/327; G01N 27/3273; G01N 27/3275; G01N 27/404; G01N 27/4074; G01N 27/4075; G01N 27/4145; G01N 27/4175; G01N 27/44708; G01N 27/44726; G01N 27/72; G01N 27/725; G01N 27/9026; G01N 2800/046; G01N 2800/125; G01N 2800/222; G01N 2800/2828; G01N 2800/2864; G01N 2800/32; G01N 2800/42; G01N 29/07; G01N 29/14; G01N 29/22; G01N 29/222; G01N 29/2418; G01N 29/32; G01N 29/46; G01N 33/0003; G01N 33/005; G01N 33/0054; G01N 33/0095; G01N 33/1806; G01N 33/1833; G01N 33/227; G01N 33/30; G01N 33/42; G01N 33/483; G01N 33/4833; G01N 33/492; G01N 33/4925; G01N 33/5073; G01N 33/5094; G01N 33/5375; G01N 33/555; G01N 33/56905; G01N 33/56922; G01N 33/56927; G01N 33/5753; G01N 33/57545; G01N 33/57555; G01N 33/5756; G01N 33/5757; G01N 33/64; G01N 33/6839; G01N 33/6875; G01N 33/728; G01N 35/1074; G01N 5/045; G01N 7/04; G01N 9/00; G01N 9/24; B01D 15/22; B01D 15/08; B01D 15/206; B01D 15/14; B01D 15/3809; B01D 15/3804; B01D 15/34; B01D 15/20; B01D 15/40; B01D 15/363; B01D 15/10; B01D 15/325; B01D 15/166; B01D 15/362; B01D 15/1871; B01D 15/361; B01D 15/1864; B01D 15/163; B01D 15/327; B01D 15/1885; B01D 15/426; B01D 15/424; B01D 53/025; B01D 15/36; B01D 15/12; B01D 15/1807; B01D 15/18; B01D 15/305; B01D 57/02; B01D 15/1821; B01D 15/203; B01D 15/00; B01D 15/247; B01D 15/3833; B01D 15/24; B01D 15/1892; B01D 15/1842; B01D 15/161; B01D 15/16; B01D 15/1878; B01D 15/3847; B01D 15/265; B01D 15/3828; B01D 53/02; B01D 69/02; B01D 15/38; B01D 11/0203; B01D 15/422; B01D 15/125; B01D 15/1828; B01D 61/18; B01D 61/00; B01D 15/366; B01D 15/3885; B01D 59/44; B01D 15/322; B01D 15/165; B01D 61/145; B01D 15/3823; B01D 15/367; B01D 15/26; B01D 11/0492; B01D 15/168; B01D 15/1814; B01D 61/44; B01D 11/0288; B01D 11/04; B01D 19/0031; B01D 15/42; B01D 15/3852; B01D 2253/102; B01D 11/02; B01D 11/0265; B01D 53/0423; B01D 67/00931; B01D 15/32; B01D 19/0042; B01D 19/0063; B01D 2257/504; B01D 53/04; B01D 53/30; B01D 53/0407; B01D 2253/106; B01D 15/30; B01D 2253/202; B01D 21/262; B01D 59/26; B01D 2253/308; B01D 59/30; B01D 69/144; B01D 63/087; B01D 61/28; B01D 19/00; B01D 15/3842; B01D 11/028; B01D 11/0403; B01D 15/185; B01D 15/02; B01D 15/3876; B01D 2257/708; B01D 2325/36; B01D 63/02; B01D 63/16; B01D 15/364; B01D 61/16; B01D 11/0407; B01D 2315/10; B01D 2253/306; B01D 15/102; B01D 19/0036; B01D 2323/30; B01D 2221/10; B01D 11/0415; B01D 2325/0283; B01D 67/0093; B01D 2325/38; B01D 61/14; B01D 61/147; B01D 61/20; B01D 61/58; B01D 69/08; B01D 15/1857; B01D 15/3857; B01D 35/02; B01D 2313/44; B01D 15/245; B01D 21/01; B01D 63/088; B01D 61/48; B01D 15/242; B01D 2256/24; B01D 67/0006; B01D 71/68; B01D 2325/12; B01D 9/0013; B01D 2311/04; B01D 11/0423; B01D 2311/18; B01D 67/0088; B01D 15/3819; B01D 21/0009; B01D 53/228; B01D 61/445; B01D 17/12; B01D 53/0446; B01D 61/243; B01D 69/107; B01D 71/56; B01D 2257/80; B01D 2325/42; B01D 2257/70; B01D 2325/04; B01D 3/00; B01D 35/00; B01D 61/38; B01D 11/0257; B01D 69/141; B01D 11/0207; B01D 19/0005; B01D 2257/7027; B01D 59/00; B01D 11/048; B01D 15/428; B01D 69/10; B01D 11/00; B01D 15/1894; B01D 3/10; B01D

63/082; B01D 2311/2697; B01D 36/00; B01D 45/16; B01D 53/0438; B01D 21/0087; B01D 2239/1216; B01D 2311/2626; B01D 11/0219; B01D 2311/2623; B01D 2325/02833; B01D 45/12; B01D 63/06; B01D 63/081; B01D 67/0062; B01D 69/1411; B01D 15/3861; B01D 63/08; B01D 19/0057; B01D 21/265; B01D 2257/2066; B01D 2313/08; B01D 43/00; B01D 53/22; B01D 65/10; B01D 71/36; B01D 9/0072; B01D 11/0292; B01D 2009/0086; B01D 2201/54; B01D 2253/31; B01D 2257/2064; B01D 61/52; B01D 1/14; B01D 17/0202; B01D 2251/304; B01D 2325/02; B01D 15/3866; B01D 2253/108; B01D 2313/60; B01D 2325/02834; B01D 29/56; B01D 11/043; B01D 21/283; B01D 2257/91; B01D 2323/38; B01D 53/1493; B01D 61/246; B01D 17/0217; B01D 2259/402; B01D 29/60; B01D 3/42; B01D 53/14; B01D 61/007; B01D 63/00; B01D 65/02; B01D 2311/08; B01D 45/08; B01D 67/0002; B01D 2258/02; B01D 2258/06; B01D 61/22; B01D 11/0484; B01D 15/1896; B01D 19/02; B01D 53/70; B01D 59/10; B01D 61/56; B01D 65/102; B01D 71/027; B01D 71/261; B01D 11/0284; B01D 2313/24; B01D 63/031; B01D 71/12; B01D 71/34; B01D 19/0078; B01D 2253/104; B01D 2257/304; B01D 2319/04; B01D 39/2017; B01D 65/109; B01D 69/14; B01D 19/0073; B01D 2239/0442; B01D 2253/311; B01D 2257/102; B01D 2311/12; B01D 2313/105; B01D 53/261; B01D 67/0034; B01D 71/76; B01D 71/82; B01D 8/00; B01D 9/005; B01D 11/0496; B01D 2253/1085; B01D 2253/1122; B01D 2253/342; B01D 2313/125; B01D 71/80; B01D 9/0063; B01D 11/0419; B01D 11/0488; B01D 2257/2062; B01D 2259/4009; B01D 2259/40094; B01D 2259/4533; B01D 2311/2653; B01D 2315/02; B01D 2325/24; B01D 61/025; B01D 63/107; B01D 69/108; B01D 2253/304; B01D 2257/204; B01D 29/01; B01D 45/04; B01D 46/2411; B01D 61/027; B01D 69/12; B01D 69/125; B01D 71/02231; B01D 71/024; B01D 2239/025; B01D 2239/0428; B01D 2259/40; B01D 2259/4148; B01D 2317/025; B01D 2323/34; B01D 53/1412; B01D 61/468; B01D 61/54; B01D 9/0036

See application file for complete search history.

(56) References Cited

U.S. PATENT DOCUMENTS

| | | | | |
|---|---|---|---|---|
| 2012/0272715 | A1 | 11/2012 | Kriel et al. | |
| 2020/0197859 | A1* | 6/2020 | Karode | B01D 69/02 |

FOREIGN PATENT DOCUMENTS

| | | | | | |
|---|---|---|---|---|---|
| CN | 201689079 | U | | 12/2010 | |
| CN | 102141557 | A | | 8/2011 | |
| CN | 203772811 | U | | 8/2014 | |
| CN | 203824974 | U | | 9/2014 | |
| CN | 104391059 | A | | 3/2015 | |
| CN | 104678034 | A | | 6/2015 | |
| CN | 107271597 | A | | 10/2017 | |
| CN | 107271597 | B | | 12/2018 | |
| CN | 109212046 | A | | 1/2019 | |
| CN | 110286165 | A | | 9/2019 | |
| CN | 120427765 | A | * | 8/2025 | |
| DE | 19808213 | A1 | | 9/1999 | |
| FR | 2860591 | A1 | | 4/2005 | |
| RU | 2589768 | C2 | | 7/2016 | |
| RU | 2677827 | C1 | * | 1/2019 | G01N 30/02 |
| RU | 2024118604 | A | * | 10/2024 | |
| RU | 2834929 | C2 | * | 2/2025 | |

OTHER PUBLICATIONS

Search Report mailed on Jun. 18, 2025, in Chinese Application No. 202111675665.9 and machine translation.

Chen et al., "Several Issues on Determination of Non-methane Hydrocarbons", Environmental Monitoring in China, vol. 29, No. 5 (2013). English abstract included.

Yang et al., "Analysis of Components in Coal-oil Co-processing Gas by Multi-gas Chromatograph", Guangzhou Chemical Industry, vol. 44, No. 16 (2016). English abstract included.

English Translation of International Search Report in Application No. PCT/CN2022/102440, mailed Sep. 16, 2022.

Zhang, Aiping et al. "Rapid Determination of Components of Imported Natural Gas by GC with Seven Columns and Five Valves" Physical Testing and Chemical Analysis Part B: Chemical Analysis, vol. 52, No. 8, Aug. 18, 2016 (Aug. 18, 2016).

Xue Qingsong et al., "Application of Multi-dimentional Gas Chromatography with Valve-Column Module in Refinery Gas Analysis", Chemical Engineering of Oil & Gas, vol. 44 No. 2, Apr. 25, 2015.

English Translation of Chinese Novelty Search Report in Application No., issued Jan. 12, 2022.

* cited by examiner

Profile of the concentration of ethyl sulfide component as function of a response value

Profile of the concentration of n-butyl mercaptan component as function of a response value

Profile of the concentration of dimethyl disulfide component as function of a response value

ANALYSIS DEVICE AND ANALYSIS METHOD FOR QUALITY INDEX OF NATURAL GAS PRODUCT AND APPLICATION

CROSS-REFERENCE TO RELATED APPLICATIONS

This application is a continuation of International Application No. PCT/CN2022/102440, filed on Jun. 29, 2022, which claims priority to Chinese Patent Application No. 202111675665.9, filed on Dec. 31, 2021, both of which are hereby incorporated by reference in their entireties.

TECHNICAL FIELD

The present invention relates to the technical field of natural gas tests, and in particular to a device and method for analyzing quality indicators of a natural gas product, and an application.

BACKGROUND

According to the Chinese mandatory national standard GB 17820-2018 "Natural Gas", the commercial natural gas obtained by pre-treating natural gas extracted from gas fields or oil fields and transported through pipelines shall be subject to the requirements of four quality indicators, i.e., high calorific value, total sulfur content (in terms of sulfur), hydrogen sulfide content and carbon dioxide content.

The conventional test methods commonly used for the quality indicators of the natural gas product are as follows. The high calorific value is typically obtained by detecting compositions by chromatography, and then calculating data of the compositions; the total sulfur content is typically measured by coulometry, ultraviolet fluorescence or hydrogenolysis and rateometric colorimetry; the hydrogen sulfide content is typically measured by iodometry, a methylene blue method, a laser method, chromatography or colorimetry; and carbon dioxide mole fraction is typically measured by chromatography. It can be seen that there are many principles for natural gas quality control indicator test methods, and multiple instruments and multiple sample loadings and analyses are needed to complete the tests, resulting in long testing cycles. Moreover, due to the need for multiple sample loadings, it is difficult to ensure the consistency of samples; and the above problems are technical problems urgent to be solved in the art.

SUMMARY OF THE INVENTION

An objective of the present invention is to provide an analysis device and an analysis method that facilitate the acquisition of quality indicators of a natural gas product.

In order to achieve the above objective, the present invention provides a device for analyzing quality indicators of a natural gas product. The device comprises a sample loading assembly, and first, second, third, fourth, and fifth chromatographic column analysis systems connected in parallel, wherein the first chromatographic column analysis system is configured for separating sulfides from natural gas; the second chromatographic column analysis system is configured for separating hydrocarbons having $C_3$ and higher from the natural gas; the third chromatographic column analysis system is configured for separating oxygen, nitrogen, methane, and carbon monoxide from the natural gas; the fourth chromatographic column analysis system is configured for separating carbon dioxide and ethane from the natural gas; and the fifth chromatographic column analysis system is configured for separating helium and hydrogen from the natural gas; wherein

- each chromatographic column analysis system is provided with a quantitative tube, a carrier gas tube, and a chromatographic column, the quantitative tube is configured for storing a natural gas sample, and the carrier gas tube is configured for delivering a carrier gas to the chromatographic column analysis system to drive components of the natural gas sample in the quantitative tube to be separated within the chromatographic column;
- the sample loading assembly is connected to the quantitative tubes of the first, second, third, fourth, and fifth chromatographic column analysis systems in a connection/disconnection controllable manner to provide a natural gas sample to the quantitative tubes of the first, second, third, fourth, and fifth chromatographic column analysis systems; and
- the chromatographic column analysis systems are connected to corresponding detectors, respectively.

The chromatographic column analysis systems are connected to the corresponding detectors such that the analysis of the contents of the components separated by the chromatographic column analysis systems can be achieved. The first chromatographic column analysis system is connected to the corresponding detector to analyze contents of the sulfides in the natural gas. The second chromatographic column analysis system is connected to the corresponding detector to analyze contents of the hydrocarbons having $C_3$ and higher in the natural gas. The third chromatographic column analysis system is connected to the corresponding detector to analyze contents of the oxygen, nitrogen, methane and carbon monoxide in the natural gas. The fourth chromatographic column analysis system is connected to the corresponding detector to analyze contents of the carbon dioxide and ethane in the natural gas. The fifth chromatographic column analysis system is connected to the corresponding detector to analyze contents of the helium and hydrogen in the natural gas.

With the device for analyzing quality indicators of a natural gas product provided in the present invention, the natural gas components are divided into five parts for component separation, target analytes in each component separation are separated by a chromatographic column, and then contents of the target analytes in that part are obtained by the corresponding detector. The device has the following beneficial effects.

On the one hand, the quality indicators of the natural gas product, including high calorific value, total sulfur content (by sulfur, $mg/m^3$), hydrogen sulfide content ($mg/m^3$), and carbon dioxide content (mole percent), can be easily determined based on the analytical results of the five parts.

On the other hand, this helps to realize a higher degree of peak separation of the target analytes in chromatograms obtained using the corresponding detectors and a more accurate result, and the accuracy of the obtained quality indicators of the natural gas product can thus be better guaranteed.

Still on the other hand, the device for analyzing quality indicators of a natural gas product provided in the present invention is an integrated device, in which the sample loading assembly is used to inject a sample into each system, and then the analysis systems are respectively used for analyzing various components, thus making the operation easy and facilitating the shortening of test cycle.

In the device for analyzing quality indicators of a natural gas product as described above, preferably, the first chromatographic column analysis system is configured for separating carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene from the natural gas.

In the device for analyzing quality indicators of a natural gas product as described above, preferably, the sample loading assembly is connected to the quantitative tubes of the first, second, third, fourth, and fifth chromatographic column analysis systems such that the quantitative tubes of the first, second, third, fourth, and fifth chromatographic column analysis systems are connected in series; wherein the sample loading assembly comprises a natural gas intake tube, a natural gas discharge tube, and first, second, third and fourth quantitative tube connecting tubes, the first, second, third and fourth quantitative tube connecting tubes are configured for connecting the quantitative tubes in series respectively, the natural gas intake tube is connected to an inlet end of the quantitative tubes connected in series, and the natural gas discharge tube is connected to an outlet end of the quantitative tubes connected in series.

In this preferred embodiment, the serial connection is more helpful for the analysis systems to carry out a single sample loading, and the consistency of samples can be better ensured. In addition, the systems can be used for analysis of various components through a single sample loading, further facilitating the shortening of the test cycle.

In a specific embodiment, the natural gas intake tube is connected to an inlet end of the quantitative tube of the first chromatographic column analysis system, and the first quantitative tube connecting tube is connected to an outlet end of the quantitative tube of the first chromatographic column analysis system, and an inlet end of the quantitative tube of the second chromatographic column analysis system, respectively; the second quantitative tube connecting tube is connected to an outlet end of the quantitative tube of the second chromatographic column analysis system, and an inlet end of the quantitative tube of the third chromatographic column analysis system, respectively; the third quantitative tube connecting tube is connected to an outlet end of the quantitative tube of the third chromatographic column analysis system, and an inlet end of the quantitative tube of the fourth chromatographic column analysis system, respectively; the fourth quantitative tube connecting tube is connected to an outlet end of the quantitative tube of the fourth chromatographic column analysis system, and an inlet end of the quantitative tube of the fifth chromatographic column analysis system, respectively; and the natural gas discharge tube is connected to an outlet end of the quantitative tube of the fifth chromatographic column analysis system.

In the device for analyzing quality indicators of a natural gas product as described above, preferably, the first chromatographic column analysis system is connected to a sulfur chemiluminescence detector (SCD), the second chromatographic column analysis system is connected to a flame ionization detector (FID), the third chromatographic column analysis system is connected to a thermal conductivity detector (TCD), the fourth chromatographic column analysis system is connected to the thermal conductivity detector (TCD), and/or the fifth chromatographic column analysis system is connected to a thermal conductivity detector (TCD).

More preferably, the device for analyzing quality indicators of a natural gas product further comprises a sulfur chemiluminescence detector, which is connected to the first chromatographic column analysis system.

More preferably, the device for analyzing quality indicators of a natural gas product further comprises a flame ionization detector, which is connected to the second chromatographic column analysis system.

More preferably, the device for analyzing quality indicators of a natural gas product further comprises a first thermal conductivity detector, which is connected to the third chromatographic column analysis system and the fourth chromatographic column analysis system, respectively.

More preferably, the device for analyzing quality indicators of a natural gas product further comprises a second thermal conductivity detector, which is connected to the fifth chromatographic column analysis system.

In the device for analyzing quality indicators of a natural gas product as described above, preferably, the chromatographic column of the first chromatographic column analysis system comprises a sulfur column; in the first chromatographic column analysis system, one end of the quantitative tube is connected to the carrier gas tube via a connection/disconnection controllable connecting tubing, the other end of the quantitative tube is connected to an inlet end of the sulfur column via a connection/disconnection controllable connecting tubing, and an outlet end of the sulfur column is connected to the sulfur chemiluminescence detector via a connection/disconnection controllable connecting tubing;

wherein the sulfur column enables separation of carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene.

More preferably, the sulfur column is selected from one of a methyl silicone-based chromatographic column, a phthalate-based chromatographic column, a bonded silica PLOT-based chromatographic column, a high-permeability PLOT-based chromatographic column, and an optimized non-polar stationary phase-based chromatographic column.

Further preferably, the sulfur column is selected from a GS-GasPro chromatographic column (belonging to the bonded silica PLOT-based chromatographic column) and a DB-Sulfur SCD chromatographic column (belonging to the optimized non-polar stationary phase-based chromatographic column).

Further preferably, the sulfur column is a DB-Sulfur SCD chromatographic column. The DB-Sulfur SCD chromatographic column has a length of 50 m to 60 m. In a specific embodiment, the DB-Sulfur SCD chromatographic column has dimensions of 60 m in length and 0.32 mm in diameter, with a liquid film thickness of 4.2 μm.

The DB-Sulfur SCD chromatographic column has more superior performance compared to other types of chromatographic columns, and can perform complete analysis of the sulfides within a suitable period of time. Although the GS-GasPro chromatographic column can perform complete analysis of the sulfides, a complete analysis takes about 45 minutes, which is not suitable for production needs. Moreover, the methyl silicone-based chromatographic column, the phthalate-based chromatographic column, and the bonded silica PLOT-based chromatographic column cannot perform complete analysis of sulfur compounds, and even have the tailing phenomenon.

In the device for analyzing quality indicators of a natural gas product as described above, preferably, the chromatographic column of the second chromatographic column analysis system comprises a first pre-separation column and a first chromatographic analytical column; in the second chromatographic column analysis system, one end of the quantitative tube is connected to the carrier gas tube via a connection/disconnection controllable connecting tubing, the other end of the quantitative tube is connected to an inlet end of the first pre-separation column via a connection/disconnection controllable connecting tubing, an outlet end of the first pre-separation column is connected to an inlet end of the first chromatographic analytical column via a connection/disconnection controllable connecting tubing, the carrier gas tube is connected to the outlet end of the first pre-separation column and the inlet end of the first chromatographic analytical column respectively via a connection/disconnection controllable connecting tubing, and the inlet end of the first pre-separation column and an outlet end of the first chromatographic analytical column are connected to the flame ionization detector respectively via a connection/disconnection controllable connecting tubing;

wherein the first pre-separation column enables separation of $C_6^+$ hydrocarbon components (hydrocarbon components having 6 or more carbons) from $C_5^-$ hydrocarbon components (hydrocarbon components having 5 or less carbons); and the first chromatographic analytical column enables separation of propane, isobutane, n-butane, neopentane, isopentane, and n-pentane.

More preferably, the first pre-separation column is selected from one of an OV-1 pre-separation column and a DB-1 capillary column. More preferably, the first pre-separation column is an OV-1 pre-separation column. More preferably, a packing material of the OV-1 pre-separation column comprises 80-100 mesh Celite 545 and silicone OV-1, where the content of silicone OV-1 is 10%-20% based on the mass of Celite 545 (Silicone OV-1 10% Celite 545 80/100 mesh). More preferably, the OV-1 pre-separation column has a length of 1.0 to 2.0 m. More preferably, the DB-1 capillary column has a length of 3.0 to 5.0 m. In a specific embodiment, the OV-1 pre-separation column has dimensions of 1.6 mm in outer diameter, 1.0 mm in inner diameter and 1.0 m in length. In a specific embodiment, the DB-1 capillary column has dimensions of 5.0 m in length and 0.55 mm in diameter, with a liquid film thickness of 20 μm.

More preferably, the first chromatographic analytical column is selected from one of an HP-Al/S chromatographic column, an HP-PLOT $Al_2O_3$ S capillary column, a PONA capillary column and a plot Q capillary column. More preferably, the first chromatographic analytical column is an HP-Al/S chromatographic column. More preferably, the HP-Al/S chromatographic column has a length of 30 m to 50 m. More preferably, the HP-PLOT $Al_2O_3$S capillary column has a length of 25 m to 50 m. More preferably, the PONA capillary column has a length of 50 m to 100 m. More preferably, the plot Q capillary column has a length of 25 m to 30 m. In a specific embodiment, the HP-Al/S chromatographic column has dimensions of 50 m in length and 0.53 mm in diameter, with a liquid film thickness of 15 μm.

In the device for analyzing quality indicators of a natural gas product as described above, preferably, the chromatographic column of the third chromatographic column analysis system comprises a second pre-separation column and a second chromatographic analytical column; in the third chromatographic column analysis system, one end of the quantitative tube is connected to the carrier gas tube via a connection/disconnection controllable connecting tubing, the other end of the quantitative tube is connected to an inlet end of the second pre-separation column via a connection/disconnection controllable connecting tubing, an outlet end of the second pre-separation column is connected to an inlet end of the second chromatographic analytical column via a connection/disconnection controllable connecting tubing, the carrier gas tube is connected to the outlet end of the second pre-separation column and the inlet end of the second chromatographic analytical column respectively via a connection/disconnection controllable connecting tubing, and an outlet end of the second chromatographic analytical column is connected to the thermal conductivity detector via a connection/disconnection controllable connecting tubing;

wherein the second pre-separation column enables separation of oxygen, nitrogen, methane, and carbon monoxide from the natural gas; and the second chromatographic analytical column enables separation of oxygen, nitrogen, methane, and carbon monoxide.

More preferably, the second pre-separation column is selected from one of a Porapak N column, a Porapak Q column and a Porapak QS column. More preferably, the second pre-separation column is a Porapak N column. More preferably, a packing material of the Porapak N column has a mesh number of 80 to 100. More preferably, the Porapak N column has a length of 3 m to 5 m. In a specific embodiment, the Porapak N-pillar has dimensions of 1.0 m in length, 3.2 mm in outer diameter and 2.1 mm in inner diameter.

More preferably, the second chromatographic analytical column is selected from one of a 13X molecular sieve column and a 5 A molecular sieve column. More preferably, the second chromatographic analytical column is an MS-13X molecular sieve column. More preferably, the MS-13X molecular sieve column has a length of 3.0 m to 5.0 m. In a specific embodiment, the MS-13X molecular sieve column has dimensions of 5.0 m in length, 3.2 mm in outer diameter and 2.1 mm in inner diameter.

In the device for analyzing quality indicators of a natural gas product as described above, preferably, the chromatographic column of the fourth chromatographic column analysis system comprises a third pre-separation column and a third chromatographic analytical column; in the fourth chromatographic column analysis system, one end of the quantitative tube is connected to the carrier gas tube via a connection/disconnection controllable connecting tubing, the other end of the quantitative tube is connected to an inlet end of the third pre-separation column via a connection/disconnection controllable connecting tubing, an outlet end of the third pre-separation column is connected to an inlet end of the third chromatographic analytical column via a connection/disconnection controllable connecting tubing, the carrier gas tube is connected to the outlet end of the third pre-separation column and the inlet end of the third chromatographic analytical column respectively via a connection/disconnection controllable connecting tubing, and an outlet end of the third chromatographic analytical column is connected to the thermal conductivity detector via a connection/disconnection controllable connecting tubing;

wherein the third pre-separation column enables separation of ethane and $CO_2$ from the natural gas; and the third chromatographic analytical column enables separation of ethane and $CO_2$.

More preferably, the third pre-separation column is selected from one of a Porapak N column, a Porapak Q column and a Porapak QS column. More preferably, the third pre-separation column is a Porapak N column. More preferably, a packing material of the Porapak N column has a mesh number of 80 to 100. More preferably, the Porapak N column has a length of 1 m to 2 m. In a specific embodiment, the Porapak N-pillar has dimensions of 1.0 m in length, 3.2 mm in outer diameter and 2.1 mm in inner diameter.

More preferably, the third chromatographic analytical column is selected from one of a Porapak N column, a Porapak Q column and a Porapak QS column. More preferably, the third chromatographic analytical column is a Porapak N column. More preferably, a packing material of the Porapak N column has a mesh number of 80 to 100. More preferably, the Porapak N column has a length of 2 m to 3 m. In a specific embodiment, the Porapak N column has dimensions of 2.0 m in length, 3.2 mm in outer diameter and 2.1 mm in inner diameter.

In the device for analyzing quality indicators of a natural gas product as described above, preferably, the chromatographic column of the fifth chromatographic column analysis system comprises a fourth pre-separation column and a fourth chromatographic analytical column; in the fifth chromatographic column analysis system, one end of the quantitative tube is connected to the carrier gas tube via a connection/disconnection controllable connecting tubing, the other end of the quantitative tube is connected to an inlet end of the fourth pre-separation column via a connection/disconnection controllable connecting tubing, an outlet end of the fourth pre-separation column is connected to an inlet end of the fourth chromatographic analytical column via a connection/disconnection controllable connecting tubing, the carrier gas tube is connected to the outlet end of the fourth pre-separation column and the inlet end of the fourth chromatographic analytical column respectively via a connection/disconnection controllable connecting tubing, and an outlet end of the fourth chromatographic analytical column is connected to the thermal conductivity detector via a connection/disconnection controllable connecting tubing;

wherein the fourth pre-separation column enables separation of helium and hydrogen from the natural gas; and the fourth chromatographic analytical column enables separation of helium and hydrogen.

More preferably, the fourth pre-separation column is selected from one of a Porapak N column, a Porapak Q column and a Porapak QS column. More preferably, the fourth pre-separation column is a Porapak N column. More preferably, a packing material of the Porapak N column has a mesh number of 80 to 100. More preferably, the Porapak N column has a length of 1 m to 2 m. In a specific embodiment, the Porapak N-pillar has dimensions of 1.0 m in length, 3.2 mm in outer diameter and 2.1 mm in inner diameter.

More preferably, the fourth chromatographic analytical column is selected from one of a 13X molecular sieve column and a 5 A molecular sieve column. More preferably, the fourth chromatographic analytical column is an MS-5 A molecular sieve column. More preferably, a packing material of the MS-5 A molecular sieve column has a mesh number of 60 to 80. More preferably, the MS-5 A molecular sieve column has a length of 3.0 m to 5.0 m. In a specific embodiment, the MS-5 A molecular sieve column has dimensions of 3.0 m in length, 3.2 mm in outer diameter, and 2.1 mm 3.2×2.1 mm×3.0 m in inner diameter.

In the device for analyzing quality indicators of a natural gas product as described above, preferably, the first chromatographic column analysis system comprises a first sample loading valve which is a multi-way valve having a first setting position and a second setting position; in the first chromatographic column analysis system, the first sample loading valve is connected to two ends of the quantitative tube, the carrier gas tube and the chromatographic column, and the first sample loading valve controls the connection/disconnection of the connecting tubing between the components of the first chromatographic column analysis system and the connection/disconnection of the connecting tubing between the sample loading assembly and the first chromatographic column analysis system;

when the first sample loading valve is switched to the first setting position, a gas in the sample loading assembly is enabled to be directly discharged from the first chromatographic column analysis system after passing through the quantitative tube; and when the first sample loading valve is switched to the second setting position, the gas in the carrier gas tube of the first chromatographic column analysis system is enabled to flow into the chromatographic column of the first chromatographic column analysis system through the quantitative tube of the first chromatographic column analysis system.

More preferably, the first sample loading valve is a six-way valve having a first setting position and a second setting position, the six-way valve being provided with a first valve port, a second valve port, a third valve port, a fourth valve port, a fifth valve port, and a sixth valve port in clockwise sequence; when the six-way valve is in the first setting position, the sixth valve port is connected to the first valve port, the second valve port is connected to the third valve port, and the fourth valve port is connected to the fifth valve port; when the six-way valve is in the second setting position, the first valve port is connected to the second valve port, the third valve port is connected to the fourth valve port, and the fifth valve port is connected to the sixth valve port; and the sixth valve port and the fifth valve port of the first sample loading valve are each connected to the sample loading assembly, the quantitative tube of the first chromatographic column analysis system has one end connected to the first valve port of the first sample loading valve and the other end connected to the fourth valve port of the first sample loading valve, the carrier gas tube of the first chromatographic column analysis system is connected to the second valve port of the first sample loading valve, and the sulfur column is connected to the third valve port of the first sample loading valve.

In the device for analyzing quality indicators of a natural gas product as described above, preferably, the second chromatographic column analysis system comprises a second sample loading valve which is a multi-way valve having a first setting position and a second setting position; in the second chromatographic column analysis system, the second sample loading valve is connected to two ends of the quantitative tube, the carrier gas tube and the chromatographic column, and the second sample loading valve controls the connection/disconnection of the connecting tubing between the components of the second chromatographic column analysis system and the connection/disconnection of the connecting tubing between the sample loading assembly and the second chromatographic column analysis system;

when the second sample loading valve is switched to the first setting position, a gas in the sample loading assembly is enabled to be directly discharged from the second chromatographic column analysis system after passing through the quantitative tube; and when the second sample loading valve is switched to the second setting position, the gas in the carrier gas tube of the second chromatographic column analysis system is enabled to flow into the chromatographic column of the second chromatographic column analysis system through the quantitative tube of the second chromatographic column analysis system.

More preferably, in the second chromatographic column analysis system, the second sample loading valve is connected to two ends of the quantitative tube, the carrier gas tube, two ends of the first pre-separation column, the inlet end of the first chromatographic analytical column, and the flame ionization detector, and the second sample loading valve controls the connection/disconnection of the connecting tubing between the components of the second chromatographic column analysis system and the connection/disconnection of the connecting tubing between the sample loading assembly and the second chromatographic column analysis system;

when the second sample loading valve is switched to the first setting position, the gas in the sample loading assembly is enabled to be directly discharged from the second chromatographic column analysis system after passing through the quantitative tube, the gas in the carrier gas tube of the second chromatographic column analysis system is enabled to enter from the outlet end of the first pre-separation column, flow out of the inlet end of the first pre-separation column and then flow into the flame ionization detector, and the gas in the carrier gas tube of the second chromatographic column analysis system is enabled to enter the first chromatographic analytical column through the inlet end of the first chromatographic analytical column; and when the second sample loading valve is switched to the second setting position, the gas in the carrier gas tube of the second chromatographic column analysis system is enabled to flow to the first pre-separation column through the quantitative tube of the second chromatographic column analysis system, enter through the inlet end of the first pre-separation column and flow out of the outlet end of the first pre-separation column, and then enter the first chromatographic analytical column through the inlet end of the first chromatographic analytical column.

Further preferably, the second sample loading valve is a ten-way valve having a first setting position and a second setting position, the second sample loading valve being provided with a first valve port, a second valve port, a third valve port, a fourth valve port, a fifth valve port, a sixth valve port, a seventh valve port, an eighth valve port, a ninth valve port, and a tenth valve port in clockwise sequence; when the second sample loading valve is in the first setting position, the tenth valve port is connected to the first valve port, the second valve port is connected to the third valve port, the fourth valve port is connected to the fifth valve port, the sixth valve port is connected to the seventh valve port, and the eighth valve port is connected to the ninth valve port; when the second sample loading valve is in the second setting position, the first valve port is connected to the second valve port, the third valve port is connected to the fourth valve port, the fifth valve port is connected to the sixth valve port, the seventh valve port is connected to the eighth valve port, and the ninth valve port is connected to the tenth valve port; and the tenth valve port and the ninth valve port of the second sample loading valve are each connected to the sample loading assembly, the quantitative tube of the second chromatographic column analysis system has one end connected to the first valve port of the second sample loading valve and the other end connected to the eighth valve port of the second sample loading valve, the carrier gas tube of the second chromatographic column analysis system is connected to each of the seventh valve port and the fourth valve port of the second sample loading valve, the first pre-separation column has the inlet end connected to the second valve port of the second sample loading valve and the outlet end connected to the sixth valve port of the second sample loading valve, the inlet end of the first chromatographic analytical column is connected to the fifth valve port of the second sample loading valve, and the third valve port of the second sample loading valve is connected to the flame ionization detector.

In the device for analyzing quality indicators of a natural gas product as described above, preferably, the third chromatographic column analysis system comprises a third sample loading valve which is a multi-way valve having a first setting position and a second setting position; in the third chromatographic column analysis system, the third sample loading valve is connected to two ends of the quantitative tube, the carrier gas tube and the chromatographic column, and the third sample loading valve controls the connection/disconnection of the connecting tubing between the components of the third chromatographic column analysis system and the connection/disconnection of the connecting tubing between the sample loading assembly and the third chromatographic column analysis system;

when the third sample loading valve is switched to the first setting position, a gas in the sample loading assembly is enabled to be directly discharged from the third chromatographic column analysis system after passing through the quantitative tube; and when the third sample loading valve is switched to the second setting position, the gas in the carrier gas tube of the third chromatographic column analysis system is enabled to flow into the chromatographic column of the third chromatographic column analysis system through the quantitative tube of the third chromatographic column analysis system.

More specifically, in the third chromatographic column analysis system, the third sample loading valve is connected to two ends of the quantitative tube, the carrier gas tube, two ends of the second pre-separation column, and the inlet end of the second chromatographic analytical column, and the third sample loading valve controls the connection/disconnection of the connecting tubing between the components of the third chromatographic column analysis system and the connection/disconnection of the connecting tubing between the sample loading assembly and the third chromatographic column analysis system;

when the third sample loading valve is switched to the first setting position, the gas in the sample loading assembly is enabled to be directly discharged from the third chromatographic column analysis system after passing through the quantitative tube, the gas in the carrier gas tube of the third chromatographic column analysis system is enabled to enter from the outlet end of the second pre-separation column and flow out of the inlet end of the second pre-separation column so as to be discharged from the three analysis systems, and the gas in the carrier gas tube of the third chromatographic column analysis system is enabled to enter the second chromatographic analytical column through the inlet end of the second chromatographic analytical column; and when the third sample loading valve is switched to the second setting position, the gas in the carrier gas tube of the third chromatographic column analysis system is enabled to flow to the second pre-separation column through the quantitative tube of the third chromatographic column analysis system, enter through the inlet end of the second pre-separation column and flow out of the outlet end of the second pre-separation column, and then enter the second chromatographic analytical column through the inlet end of the second chromatographic analytical column.

Further preferably, the third sample loading valve is a ten-way valve having a first setting position and a second setting position, the third sample loading valve being provided with a first valve port, a second valve port, a third valve port, a fourth valve port, a fifth valve port, a sixth valve port, a seventh valve port, an eighth valve port, a ninth valve port, and a tenth valve port in clockwise sequence; when the third sample loading valve is in the first setting position, the tenth valve port is connected to the first valve port, the second valve port is connected to the third valve port, the fourth valve port is connected to the fifth valve port, the sixth valve port is connected to the seventh valve port, and the eighth valve port is connected to the ninth valve port; when the third sample loading valve is in the second setting position, the first valve port is connected to the second valve port, the third valve port is connected to the fourth valve port, the fifth valve port is connected to the sixth valve port, the seventh valve port is connected to the eighth valve port, and the ninth valve port is connected to the tenth valve port; and the tenth valve port and the ninth valve port of the third sample loading valve are each connected to the sample loading assembly, the quantitative tube of the third chromatographic column analysis system has one end connected to the first valve port of the third sample loading valve and the other end connected to the eighth valve port of the third sample loading valve, the carrier gas tube of the third chromatographic column analysis system is connected to the seventh valve port and the fourth valve port of the third sample loading valve, the second pre-separation column has the inlet end connected to the second valve port of the third sample loading valve and the outlet end connected to the sixth valve port of the third sample loading valve, and the inlet end of the second chromatographic analytical column is connected to the fifth valve port of the third sample loading valve.

In the device for analyzing quality indicators of a natural gas product as described above, preferably, the fourth chromatographic column analysis system comprises a fourth sample loading valve which is a multi-way valve having a first setting position and a second setting position; in the fourth chromatographic column analysis system, the fourth sample loading valve is connected to two ends of the quantitative tube, the carrier gas tube, and the chromatographic column, and the fourth sample loading valve controls the connection/disconnection of the connecting tubing between the components of the fourth chromatographic column analysis system and the connection/disconnection of the connecting tubing between the sample loading assembly and the fourth chromatographic column analysis system;

when the fourth sample loading valve is switched to the first setting position, a gas in the sample loading assembly is enabled to be directly discharged from the fourth chromatographic column analysis system after passing through the quantitative tube; and when the fourth sample loading valve is switched to the second setting position, the gas in the carrier gas tube of the fourth chromatographic column analysis system is enabled to flow into the chromatographic column of the fourth chromatographic column analysis system through the quantitative tube of the fourth chromatographic column analysis system.

More preferably, in the fourth chromatographic column analysis system, the fourth sample loading valve is connected to two ends of the quantitative tube, the carrier gas tube, two ends of the third pre-separation column, and the inlet end of the third chromatographic analytical column, and the fourth sample loading valve controls the connection/disconnection of the connecting tubing between the components of the fourth chromatographic column analysis system and the connection/disconnection of the connecting tubing between the sample loading assembly and the fourth chromatographic column analysis system;

when the fourth sample loading valve is switched to the first setting position, the gas in the sample loading assembly is enabled to be directly discharged from the fourth chromatographic column analysis system after passing through the quantitative tube, the gas in the carrier gas tube of the fourth chromatographic column analysis system is enabled to enter from the outlet end of the third pre-separation column and flow out of the inlet end of the third pre-separation column so as to be discharged from the three analysis systems, and the gas in the carrier gas tube of the fourth chromatographic column analysis system is enabled to enter the third chromatographic analytical column through the inlet end of the third chromatographic analytical column; and when the fourth sample loading valve is switched to the second setting position, the gas in the carrier gas tube of the fourth chromatographic column analysis system is enabled to flow to the third pre-separation column through the quantitative tube of the fourth chromatographic column analysis system, enter through the inlet end of the third pre-separation column and flow out of the outlet end of the third pre-separation column, and then enter the third chromatographic analytical column through the inlet end of the third chromatographic analytical column.

Further preferably, the fourth sample loading valve is a ten-way valve having a first setting position and a second setting position, the fourth sample loading valve being provided with a first valve port, a second valve port, a third valve port, a fourth valve port, a fifth valve port, a sixth valve port, a seventh valve port, an eighth valve port, a ninth valve port, and a tenth valve port in clockwise sequence; when the fourth sample loading valve is in the first setting position, the tenth valve port is connected to the first valve port, the second valve port is connected to the third valve port, the fourth valve port is connected to the fifth valve port, the sixth valve port is connected to the seventh valve port, and the eighth valve port is connected to the ninth valve port; when the fourth sample loading valve is in the second setting position, the first valve port is connected to the second valve port, the third valve port is connected to the fourth valve port, the fifth valve port is connected to the sixth valve port, the seventh valve port is connected to the eighth valve port, and the ninth valve port is connected to the tenth valve port; and the tenth valve port and the ninth valve port of the fourth sample loading valve are each connected to the sample loading assembly, the quantitative tube of the fourth chromatographic column analysis system has one end connected to the first valve port of the fourth sample loading valve and the other end connected to the eighth valve port of the fourth sample loading valve, the carrier gas tube of the fourth chromatographic column analysis system is connected to the seventh valve port and the fourth valve port of the fourth sample loading valve, the third pre-separation column has the inlet end connected to the second valve port of the fourth sample loading valve and the outlet end connected to the sixth valve port of the fourth sample loading valve, and the inlet end of the third chromatographic analytical column is connected to the fifth valve port of the fourth sample loading valve.

In the device for analyzing quality indicators of a natural gas product as described above, preferably, the fifth chromatographic column analysis system comprises a fifth sample loading valve which is a multi-way valve comprising a first setting position and a second setting position; in the fifth chromatographic column analysis system, the fifth sample loading valve is connected to two ends of the quantitative tube, the carrier gas tube, and the chromatographic column, and the fifth sample loading valve controls the connection/disconnection of the connecting tubing between the components of the fifth chromatographic column analysis system and the connection/disconnection of the connecting tubing between the sample loading assembly and the fifth chromatographic column analysis system;

when the fifth sample loading valve is switched to the first setting position, a gas in the sample loading assembly is enabled to be directly discharged from the fifth chromatographic column analysis system after passing through the quantitative tube; and when the fifth sample loading valve is switched to the second setting position, the gas in the carrier gas tube of the fifth chromatographic column analysis system is enabled to flow into the chromatographic column of the fifth chromatographic column analysis system through the quantitative tube of the fifth chromatographic column analysis system.

More preferably, in the fifth chromatographic column analysis system, the fifth sample loading valve is connected to two ends of the quantitative tube, the carrier gas tube, two ends of the fourth pre-separation column, and the inlet end of the fourth chromatographic analytical column, and the fifth sample loading valve controls the connection/disconnection of the connecting tubing between the components of the fifth chromatographic column analysis system and the connection/disconnection of the connecting tubing between the sample loading assembly and the fifth chromatographic column analysis system;

when the fifth sample loading valve is switched to the first setting position, the gas in the sample loading assembly is enabled to be directly discharged from the fifth chromatographic column analysis system after passing through the quantitative tube, the gas in the carrier gas tube of the fifth chromatographic column analysis system is enabled to enter from the outlet end of the fourth pre-separation column and flow out of the inlet end of the fourth pre-separation column so as to be discharged from the three analysis systems, and the gas in the carrier gas tube of the fifth chromatographic column analysis system is enabled to enter the fourth chromatographic analytical column through the inlet end of the fourth chromatographic analytical column; and when the fifth sample loading valve is switched to the second setting position, the gas in the carrier gas tube of the fifth chromatographic column analysis system is enabled to flow to the fourth pre-separation column through the quantitative tube of the fifth chromatographic column analysis system, enter through the inlet end of the fourth pre-separation column and flow out of the outlet end of the fourth pre-separation column, and then enter the fourth chromatographic analytical column through the inlet end of the fourth chromatographic analytical column.

Further preferably, the fifth sample loading valve is a ten-way valve having a first setting position and a second setting position, the fifth sample loading valve being provided with a first valve port, a second valve port, a third valve port, a fourth valve port, a fifth valve port, a sixth valve port, a seventh valve port, an eighth valve port, a ninth valve port, and a tenth valve port in clockwise sequence; when the fifth sample loading valve is in the first setting position, the tenth valve port is connected to the first valve port, the second valve port is connected to the third valve port, the fourth valve port is connected to the fifth valve port, the sixth valve port is connected to the seventh valve port, and the eighth valve port is connected to the ninth valve port; when the fifth sample loading valve is in the second setting position, the first valve port is connected to the second valve port, the third valve port is connected to the fourth valve port, the fifth valve port is connected to the sixth valve port, the seventh valve port is connected to the eighth valve port, and the ninth valve port is connected to the tenth valve port; and the tenth valve port and the ninth valve port of the fifth sample loading valve are each connected to the sample loading assembly, the quantitative tube of the fifth chromatographic column analysis system has one end connected to the first valve port of the fifth sample loading valve and the other end connected to the eighth valve port of the fifth sample loading valve, the carrier gas tube of the fifth chromatographic column analysis system is connected to the seventh valve port and the fourth valve port of the fifth sample loading valve, the fourth pre-separation column has the inlet end connected to the second valve port of the fifth sample loading valve and the outlet end connected to the sixth valve port of the fifth sample loading valve, and the inlet end of the fourth chromatographic analytical column is connected to the fifth valve port of the fifth sample loading valve.

In a specific embodiment, the sample loading assembly comprises a natural gas intake tube, a natural gas discharge tube, and first, second, third and fourth quantitative tube connecting tubes, the first, second, third and fourth quantitative tube connecting tubes are configured for connecting the quantitative tubes in series respectively, the natural gas intake tube is connected to an inlet end of the quantitative tubes connected in series, and the natural gas discharge tube is connected to an outlet end of the quantitative tubes connected in series.

In this case, the first, second, third, fourth and fifth sample loading valves are connected in series via the first, second, third and fourth quantitative tube connecting tubes, and the natural gas intake tube and the natural gas discharge tube are respectively connected to the first and last sample loading valves of the first, second, third, fourth and fifth sample loading valves that are connected in series.

In the device for analyzing quality indicators of a natural gas product as described above, preferably, the device further comprises a programmed temperature ramp apparatus in which the sulfur column of the first chromatographic column analysis system and/or the first chromatographic analytical column of the second chromatographic column analysis system are disposed.

In the device for analyzing quality indicators of a natural gas product as described above, preferably, the device further comprises a thermostat in which the second chromatographic analytical column of the third chromatographic column analysis system, the third chromatographic analytical column of the fourth chromatographic column analysis system, and/or, the fourth chromatographic analytical column of the fifth chromatographic column analysis system are disposed.

In the device for analyzing quality indicators of a natural gas product as described above, preferably, the volume of the quantitative tube of the first chromatographic column analysis system is 1 mL.

In the device for analyzing quality indicators of a natural gas product as described above, preferably, the volume of the quantitative tube of the second chromatographic column analysis system is 100 μL.

In the device for analyzing quality indicators of a natural gas product as described above, preferably, the volume of the quantitative tube of the third chromatographic column analysis system is 1 mL.

In the device for analyzing quality indicators of a natural gas product as described above, preferably, the volume of the quantitative tube of the fourth chromatographic column analysis system is 1 mL.

In the device for analyzing quality indicators of a natural gas product as described above, preferably, the volume of the quantitative tube of the fifth chromatographic column analysis system is 5 mL.

The present invention further provides a method for analyzing quality indicators of a natural gas product. The method is implemented using a device for analyzing quality indicators of a natural gas product as described above. The method comprises:

- injecting a sample into the quantitative tubes of the first chromatographic column analysis system, the second chromatographic column analysis system, the third chromatographic column analysis system, the fourth chromatographic column analysis system, and the fifth chromatographic column analysis system such that each of the quantitative tubes is filled with a natural gas sample;
- in the first chromatographic column analysis system, using the carrier gas tube to deliver a carrier gas, using the chromatographic column to separate sulfides from the natural gas sample in the quantitative tube under the driving of the carrier gas, and delivering the separated components to a detector for detection to obtain a first detection chromatogram; determining contents of the sulfides in the natural gas sample based on the obtained first detection chromatogram;
- in the second chromatographic column analysis system, using the carrier gas tube to deliver a carrier gas, using the chromatographic column to separate hydrocarbons having $C_3$ and higher from the natural gas sample in the quantitative tube under the driving of the carrier gas, and delivering the separated components to a detector for detection to obtain a second detection chromatogram; determining contents of the hydrocarbons having $C_3$ and higher in the natural gas sample based on the obtained second detection chromatogram;
- in the third chromatographic column analysis system, using the carrier gas tube to deliver a carrier gas, using the chromatographic column to separate oxygen, nitrogen, methane, and carbon monoxide from the natural gas sample in the quantitative tube under the driving of the carrier gas, and delivering the separated components to a detector for detection to obtain a third detection chromatogram; determining contents of the oxygen, nitrogen, methane and carbon monoxide in the natural gas sample based on the obtained third detection chromatogram;
- in the fourth chromatographic column analysis system, using the carrier gas tube to deliver a carrier gas, using the chromatographic column to separate carbon dioxide and ethane from the natural gas sample in the quantitative tube under the driving of the carrier gas, and delivering the separated components to a detector for detection to obtain a fourth detection chromatogram; determining contents of the carbon dioxide and ethane in the natural gas sample based on the obtained fourth detection chromatogram;
- in the fifth chromatographic column analysis system, using the carrier gas tube to deliver a carrier gas, using the chromatographic column to separate helium and hydrogen from the natural gas sample in the quantitative tube under the driving of the carrier gas, and delivering the separated components to a detector for detection to obtain a fifth detection chromatogram; determining contents of the helium and hydrogen in the natural gas sample based on the obtained fifth detection chromatogram; and
- based on the obtained contents of the sulfides in the natural gas sample, the hydrocarbons having $C_3$ and higher in the natural gas sample, the oxygen, nitrogen, methane and carbon monoxide in the natural gas sample, the carbon dioxide and ethane in the natural gas sample, and the helium and hydrogen in the natural gas sample, determining the natural gas high calorific value, the total sulfur content (in terms of sulfur, in $mg/m^3$), the hydrogen sulfide content (in $mg/m^3$), and/or the carbon dioxide content (in mole percent).

By using the integrated device for analyzing quality indicators of a natural gas product disclosed in the present invention, together with the SCD, FID, and TCDs, 13 types of sulfur compounds and 15 types of conventional components in the natural gas product can be analyzed in a single sample loading, and the analysis cycle for detecting all components in a single sample loading is less than 20 minutes.

In the method for analyzing quality indicators of a natural gas product as described above, based on the obtained first detection chromatogram, the contents of the sulfides in the natural gas sample can be determined in a conventional manner in the art, for example, in a manner of comparing the first detection chromatogram with standard curves of the contents of the sulfides. Specifically, response peak area data is obtained according to the first detection chromatogram, and the contents of the sulfides in the natural gas sample are then determined according to the response peak data using the standard curves of the contents of the sulfides. The standard curves of the contents of the sulfides may be obtained by performing a standard sample gas test.

In the method for analyzing quality indicators of a natural gas product as described above, based on the obtained second detection chromatogram, the contents of the hydrocarbons having $C_3$ and higher in the natural gas sample can be determined in a conventional manner in the art, for example, in a manner of comparing the second detection chromatogram with standard curves of the contents of the hydrocarbons having $C_3$ and higher. Specifically, response peak area data is obtained according to the second detection chromatogram, and the contents of the hydrocarbons having $C_3$ and higher in the natural gas sample are then determined according to the response peak data using the standard curves of the contents of the hydrocarbons having $C_3$ and higher. The standard curves of the contents of the hydrocarbons having $C_3$ and higher may be obtained by performing a standard sample gas test.

In the method for analyzing quality indicators of a natural gas product as described above, based on the obtained third detection chromatogram, the contents of the oxygen, nitrogen, methane and carbon monoxide in the natural gas sample can be determined in a conventional manner in the art, for example, in a manner of comparing the third detection chromatogram with standard curves of the contents of the oxygen, nitrogen, methane and carbon monoxide. Specifically, response peak area data is obtained according to the third detection chromatogram, and the contents of the oxygen, nitrogen, methane and carbon monoxide in the natural gas sample are then determined according to the response peak data using the standard curves of the contents of the oxygen, nitrogen, methane and carbon monoxide. The standard curves of the contents of the oxygen, nitrogen, methane and carbon monoxide may be obtained by performing a standard sample gas test.

In the method for analyzing quality indicators of a natural gas product as described above, based on the obtained fourth detection chromatogram, the contents of the carbon dioxide and ethane in the natural gas sample can be determined in a conventional manner in the art, for example, in a manner of comparing the fourth detection chromatogram with standard curves of the contents of the carbon dioxide and ethane. Specifically, response peak area data is obtained according to the fourth detection chromatogram, and the contents of the carbon dioxide and ethane in the natural gas sample are then determined according to the response peak data using the standard curves of the contents of the carbon dioxide and ethane. The standard curves of the contents of the carbon dioxide and ethane may be obtained by performing a standard sample gas test.

In the method for analyzing quality indicators of a natural gas product as described above, based on the obtained fifth detection chromatogram, the contents of the helium and hydrogen in the natural gas sample can be determined in a conventional manner in the art, for example, in a manner of comparing the fifth detection chromatogram with standard curves of the contents of the helium and hydrogen. Specifically, response peak area data is obtained according to the fifth detection chromatogram, and the contents of the helium and hydrogen in the natural gas sample are then determined according to the response peak data using the standard curves of the contents of the helium and hydrogen. The standard curves of the contents of the helium and hydrogen may be obtained by performing a standard sample gas test.

In the method for analyzing quality indicators of a natural gas product as described above, the high calorific value of the natural gas may be determined using a conventional manner in the art, for example, in a manner of obtaining the mole percent of sulfur compounds and the mole percents of hydrocarbons and non-hydrocarbons based on the contents of the sulfides in the natural gas sample, the contents of the hydrocarbons having $C_3$ and higher in the natural gas sample, the contents of the oxygen, nitrogen, methane and carbon monoxide in the natural gas sample, the contents of the carbon dioxide and ethane in the natural gas sample, and the contents of the helium and hydrogen in the natural gas sample, with a total percent of 100%, and then determining the high calorific value of the natural gas by using a high calorific value calculation model.

In the method for analyzing quality indicators of a natural gas product as described above, the total sulfur content of the natural gas may be determined in a conventional manner in the art, for example, in the manner of obtaining the sum of the contents of the sulfides, i.e., the total sulfur content of the natural gas, based on the contents of the sulfides in the natural gas sample.

In the method for analyzing quality indicators of a natural gas product as described above, the hydrogen sulfide content of the natural gas may be determined in a conventional manner in the art. For example, the content of hydrogen sulfide in the natural gas sample is the hydrogen sulfide content of the natural gas.

In the method for analyzing quality indicators of a natural gas product as described above, the carbon dioxide content of the natural gas may be determined in a conventional manner in the art, for example, in a manner of obtaining the sum of the contents of the components based on the contents of the hydrocarbons having $C_3$ and higher in the natural gas sample, the contents of the oxygen, nitrogen, methane and carbon monoxide in the natural gas sample, the contents of the carbon dioxide and ethane in the natural gas sample, and the contents of the helium and hydrogen in the natural gas sample, and then determining the proportion of the carbon dioxide content based on the sum of the contents of the components as the carbon dioxide content of the natural gas.

In the method for analyzing quality indicators of a natural gas product as described above, preferably, the step of, in the first chromatographic column analysis system, using the carrier gas tube to deliver a carrier gas, using the chromatographic column to separate sulfides from the natural gas sample in the quantitative tube under the driving of the carrier gas, and delivering the separated components to a detector for detection to obtain a first detection chromatogram comprises:

in the first chromatographic column analysis system, using the carrier gas tube to deliver the carrier gas, delivering the natural gas sample in the quantitative tube to the sulfur column under the driving of the carrier gas to separate the sulfides, and delivering the separated components to a sulfur chemiluminescence detector such that the sulfides in the natural gas sample are detected so as to obtain the first detection chromatogram.

In this preferred technical solution, the natural gas sample is separated by the sulfur column under the driving of the carrier gas, and carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene of the sulfides are sequentially discharged from the sulfur column into the sulfur chemiluminescence detector for detection.

More preferably, the sulfur column is maintained at 30-50° C. until carbonyl sulfur exits the sulfur column, and the sulfur column is then heated at a rate of 10-20° C./min to, and maintained at, 130° C.-150° C.

In a specific embodiment, the flow rate of the carrier gas is 3 mL/min.

In a specific embodiment, the sulfur chemiluminescence detector has a sample loading temperature of 200° C., and a reaction temperature of 850° C., and flow rates of reaction gases in the sulfur chemiluminescence detector are 80 mL/min of hydrogen ($H_2$), 40 mL/min of nitrogen ($N_2$), 10 mL/min of oxygen ($O_2$), and 25 mL/min of ozone ($O_3$).

In the method for analyzing quality indicators of a natural gas product as described above, preferably, the step of, in the second chromatographic column analysis system, using the carrier gas tube to deliver a carrier gas, using the chromatographic column to separate hydrocarbons having $C_3$ and higher from the natural gas sample in the quantitative tube under the driving of the carrier gas, and delivering the separated components to a detector for detection to obtain a second detection chromatogram comprises:

in the second chromatographic column analysis system, using the carrier gas tube to deliver the carrier gas, and using the first pre-separation column and the first chromatographic analytical column in sequence to perform separation on the natural gas sample in the quantitative tube under the driving of the carrier gas; when $C_5^-$ components in the natural gas sample exit the first pre-separation column and enter the first chromatographic analytical column, transferring the carrier gas to the outlet end of the first pre-separation column, connecting the inlet end of the first pre-separation column to the flame ionization detector, and under the driving of the carrier gas, back flushing $C_6^+$ hydrocarbon components from the first pre-separation column to a flame ionization detector for detection; and after the back flushing is completed, transferring the carrier gas to the inlet end of the first chromatographic analytical column, and under the driving of the carrier gas, sequentially introducing $C_3^-$ hydrocarbon components separated by the first chromatographic analytical column into the flame ionization detector for detection, so as to obtain the second detection chromatogram.

In this preferred technical solution, the first pre-separation column and the first chromatographic analytical column are used in sequence to separate the natural gas sample under the driving of the carrier gas, and propane, isobutane, n-butane, neopentane, isopentane, and n-pentane in the natural gas sample are discharged from the first pre-separation column into the first chromatographic analytical column for separation, so that the time difference in separation of the components is increased. When the $C_5^-$ components exit the first pre-separation column and enter the first chromatographic analytical column, the carrier gas is transferred to the outlet end of the first pre-separation column, the inlet end of the first pre-separation column is connected to the flame ionization detector, the $C_6^+$ hydrocarbon components in the first pre-separation column first pass, in the form of hexane combined peak, through the flame ionization detector for detection by reversing the flow of the carrier gas. The carrier gas is then transferred to the inlet end of the first chromatographic analytical column, and under the driving of the carrier gas, propane, isobutane, n-butane, neopentane, isopentane, and n-pentane are sequentially discharged from the first chromatographic analytical column into the flame ionization detector for detection.

More preferably, the first chromatographic analytical column is maintained at 30-50° C. until the flame ionization detector monitors peaks of the $C_6^+$ hydrocarbon components, and the first chromatographic analytical column is then heated at a rate of 10-20° C./min to, and maintained at, 130° C.-150° C.

In a specific embodiment, the carrier gas is injected at a pressure of 500 kPa.

In a specific embodiment, the temperature of the flame ionization detector is 200° C., and flow rates of reaction gases of the flame ionization detector are 32 mL/min of hydrogen ($H_2$), 200 mL/min of air, and 20 mL/min of make-up gas (Make-up).

In the method for analyzing quality indicators of a natural gas product as described above, preferably, the step of, in the third chromatographic column analysis system, using the carrier gas tube to deliver a carrier gas, using the chromatographic column to separate oxygen, nitrogen, methane, and carbon monoxide from the natural gas sample in the quantitative tube under the driving of the carrier gas, and delivering the separated components to a detector for detection to obtain a third detection chromatogram comprises:

in the third chromatographic column analysis system, using the carrier gas tube to deliver the carrier gas, and using the second pre-separation column and the second chromatographic analytical column in sequence to perform separation on the natural gas sample in the quantitative tube under the driving of the carrier gas; after the oxygen, nitrogen, methane and carbon monoxide components in the natural gas sample exit the second pre-separation column and enter the second chromatographic analytical column, transferring the carrier gas to the outlet end of the second pre-separation column, and back flushing the remaining components in the second pre-separation column out of the third chromatographic column analysis system under the driving of the carrier gas; and after the back flushing is completed, transferring the carrier gas to the inlet end of the second chromatographic analytical column, and under the driving force of the carrier gas, sequentially introducing the oxygen, nitrogen, methane and carbon monoxide components separated by the second chromatographic analytical column into the thermal conductivity detector for detection, so as to obtain the third detection chromatogram.

In this preferred technical solution, the second pre-separation column and the second chromatographic analytical column are used in sequence to separate the natural gas sample under the driving of the carrier gas, and the oxygen, nitrogen, methane and carbon monoxide in the natural gas sample are discharged from the second pre-separation column into the second chromatographic analytical column for separation, so that the time difference in separation of the components is increased. After the oxygen, nitrogen, methane and carbon monoxide components exit the second pre-separation column and enter the second chromatographic analytical column, the carrier gas is transferred to the outlet end of the second pre-separation column, and the remaining components in the second pre-separation column are flushed out and removed by reversing the flow of the carrier gas. The carrier gas is then transferred to the inlet end of the second chromatographic analytical column, and under the driving of the carrier gas, the oxygen, nitrogen, methane and carbon monoxide are sequentially discharged from the second chromatographic analytical column into the thermal conductivity detector for detection.

More preferably, the column temperature of the second chromatographic analytical column is 50-70° C.

In a specific embodiment, the carrier gas is injected at a pressure of 295-500 kPa.

In a specific embodiment, the temperature of the thermal conductivity detector is 150° C., and the thermal conductivity detector has an operating current of 120 mA, and is cathodic in polarity.

In the method for analyzing quality indicators of a natural gas product as described above, preferably, the step of, in the fourth chromatographic column analysis system, using the carrier gas tube to deliver a carrier gas, using the chromatographic column to separate carbon dioxide and ethane from the natural gas sample in the quantitative tube under the driving of the carrier gas, and delivering the separated components to a detector for detection to obtain a fourth detection chromatogram comprises:

in the fourth chromatographic column analysis system, using the carrier gas tube to deliver the carrier gas, and using the third pre-separation column and the third chromatographic analytical column in sequence to perform separation on the natural gas sample in the quantitative tube under the driving of the carrier gas; after the carbon dioxide and ethane components in the natural gas sample exit the third pre-separation column and enter the third chromatographic analytical column, transferring the carrier gas to the outlet end of the third pre-separation column, and back flushing the remaining components in the third pre-separation column out of the fourth chromatographic column analysis system under the driving of the carrier gas; and after the back flushing is completed, transferring the carrier gas to the inlet end of the third chromatographic analytical column, and under the driving of the carrier gas, sequentially introducing the carbon dioxide and ethane components separated by the third chromatographic analytical column into the thermal conductivity detector for detection, so as to obtain the fourth detection chromatogram.

In this preferred technical solution, the third pre-separation column and the third chromatographic analytical column are used in sequence to separate the natural gas sample under the driving of the carrier gas, and the carbon dioxide and ethane in the natural gas sample are discharged from the third pre-separation column into the third chromatographic analytical column for separation, so that the time difference in separation of the components is increased. After the carbon dioxide and ethane components exit the third pre-separation column and enter the third chromatographic analytical column, the carrier gas is transferred to the outlet end of the third pre-separation column, and the remaining components in the third pre-separation column are flushed out and removed by reversing the flow of the carrier gas. The carrier gas is then transferred to the inlet end of the third chromatographic analytical column, and under the driving of the carrier gas, the carbon dioxide and ethane are sequentially discharged from the third chromatographic analytical column into the thermal conductivity detector for detection.

More preferably, the column temperature of the third chromatographic analytical column is 50-70° C.

In a specific embodiment, the carrier gas is injected at a pressure of 278-350 kPa.

In a specific embodiment, the temperature of the thermal conductivity detector is 150° C., and the thermal conductivity detector has an operating current of 120 mA, and is cathodic in polarity.

In the method for analyzing quality indicators of a natural gas product as described above, preferably, the step of, in the fifth chromatographic column analysis system, using the carrier gas tube to deliver a carrier gas, using the chromatographic column to separate helium and hydrogen from the natural gas sample in the quantitative tube under the driving of the carrier gas, and delivering the separated components to a detector for detection to obtain a fifth detection chromatogram comprises:

in the fifth chromatographic column analysis system, using the carrier gas tube to deliver the carrier gas, and using the fourth pre-separation column and the fourth chromatographic analytical column in sequence to perform separation on the natural gas sample in the quantitative tube under the driving of the carrier gas; after the helium and hydrogen components in the natural gas sample exit the fourth pre-separation column and enter the fourth chromatographic analytical column, transferring the carrier gas to the outlet end of the fourth pre-separation column, and back flushing the remaining components in the fourth pre-separation column out of the fifth chromatographic column analysis system under the driving of the carrier gas; and after the back flushing is completed, transferring the carrier gas to the inlet end of the fourth chromatographic analytical column, and under the driving of the carrier gas, sequentially introducing the helium and hydrogen components separated by the fourth chromatographic analytical column into the thermal conductivity detector for detection, so as to obtain the fifth detection chromatogram.

In this preferred technical solution, the fourth pre-separation column and the fourth chromatographic analytical column are used in sequence to separate the natural gas sample under the driving of the carrier gas, and the helium and hydrogen in the natural gas sample are discharged from the fourth pre-separation column into the fourth chromatographic analytical column for separation, so that the time difference in separation of the components is increased. After the helium and hydrogen components exit the fourth pre-separation column and enter the fourth chromatographic analytical column, the carrier gas is transferred to the outlet end of the fourth pre-separation column, and the remaining components in the fourth pre-separation column are flushed out and removed by reversing the flow of the carrier gas. The carrier gas is then transferred to the inlet end of the fourth chromatographic analytical column, and under the driving of the carrier gas, the helium and hydrogen are sequentially discharged from the fourth chromatographic analytical column into the thermal conductivity detector for detection.

More preferably, the column temperature of the fourth chromatographic analytical column is 50-70° C.

In a specific embodiment, the carrier gas is injected at a pressure of 250 kPa.

In a specific embodiment, the temperature of the thermal conductivity detector is 150° C., and the thermal conductivity detector has an operating current of 70 mA, and is anodic in polarity.

In the method for analyzing quality indicators of a natural gas product as described above, preferably, the carrier gas used in the first chromatographic column analysis system is helium.

In the method for analyzing quality indicators of a natural gas product as described above, preferably, the carrier gas used in the second chromatographic column analysis system is helium.

In the method for analyzing quality indicators of a natural gas product as described above, preferably, the carrier gas used in the third chromatographic column analysis system is helium.

In the method for analyzing quality indicators of a natural gas product as described above, preferably, the carrier gas used in the fourth chromatographic column analysis system is helium.

In the method for analyzing quality indicators of a natural gas product as described above, preferably, the carrier gas used in the fifth chromatographic column analysis system is nitrogen.

The present invention further provides an application of a device for analyzing quality indicators of a natural gas product in natural gas product analysis.

DESCRIPTION OF MAIN REFERENCE SIGNS

Figure 1:
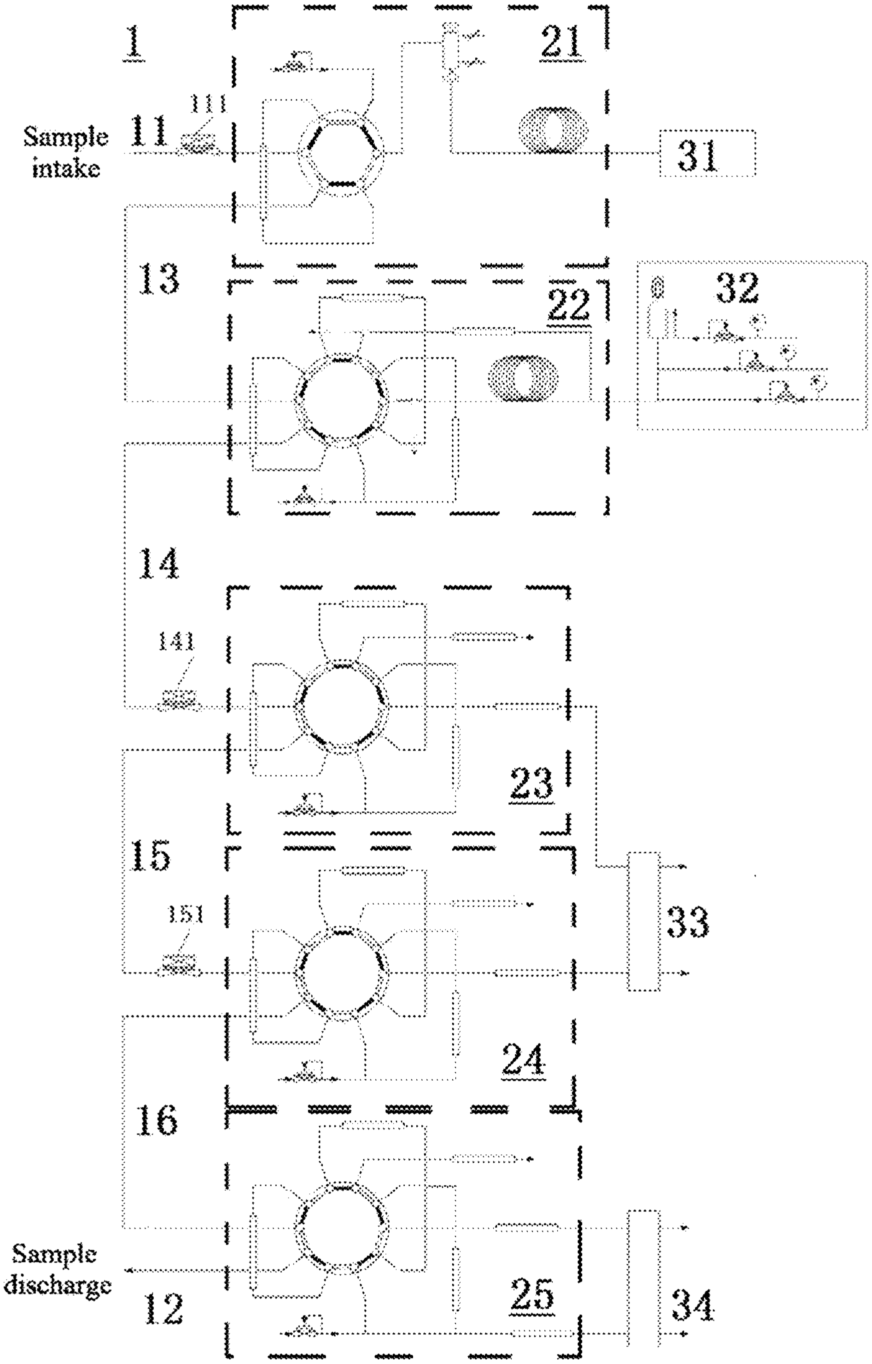
FIG. 1 shows a schematic structural diagram of a device for analyzing quality indicators of a natural gas product in Example 1 of the present invention.
Figure 2:
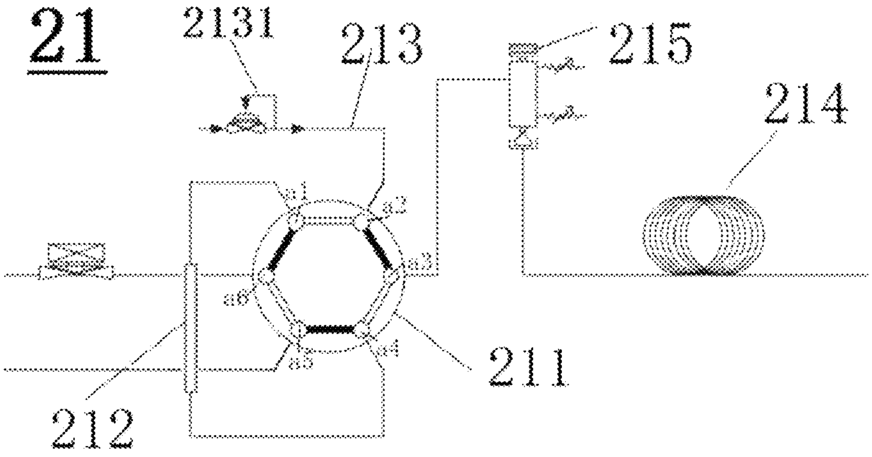
FIG. 2 shows a schematic structural diagram of a first chromatographic column analysis system in Example 1 of the present invention.
Figure 3:
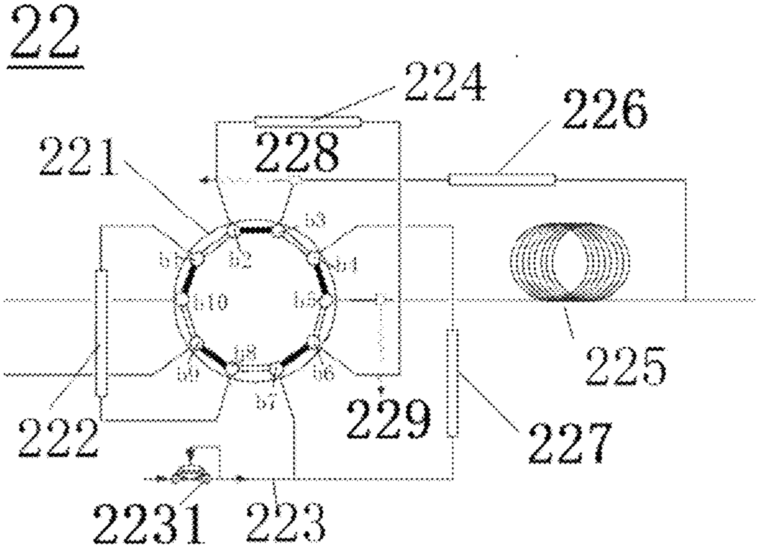
FIG. 3 shows a schematic structural diagram of a second chromatographic column analysis system in Example 1 of the present invention.
Figure 4:
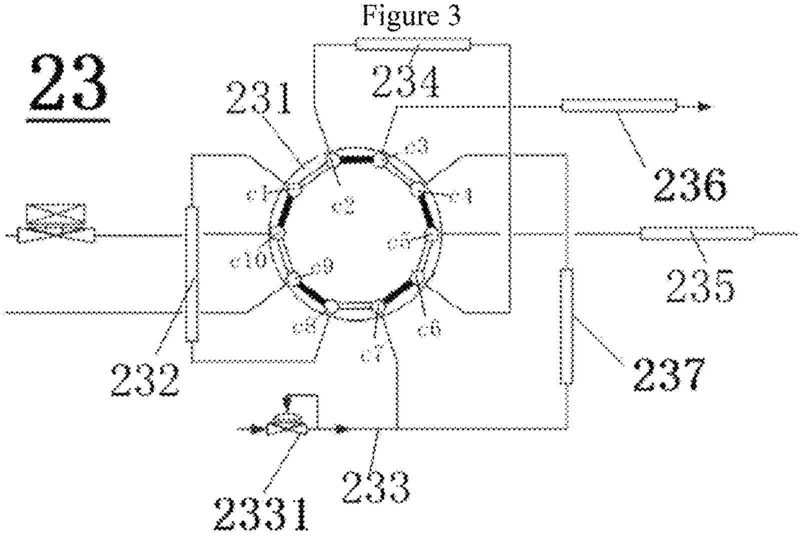
FIG. 4 shows a schematic structural diagram of a third chromatographic column analysis system in Example 1 of the present invention.
Figure 5:
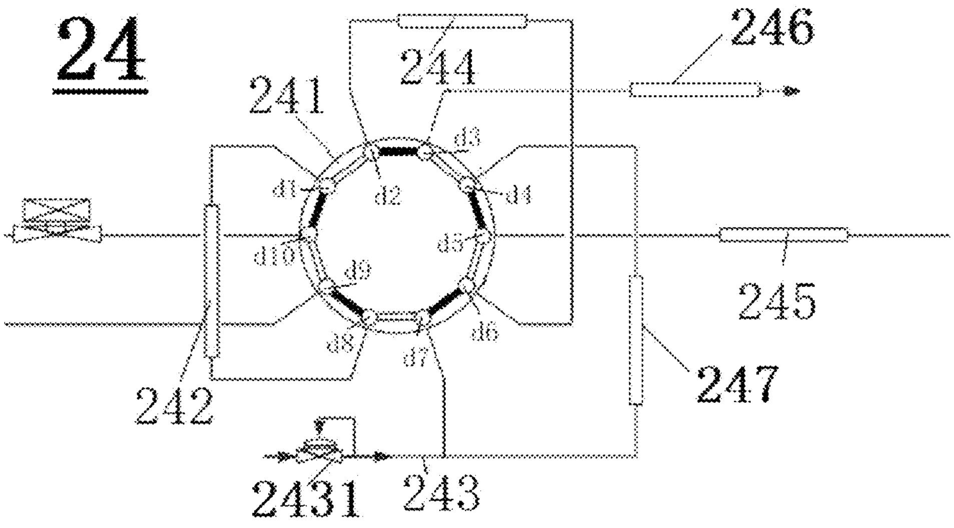
FIG. 5 shows a schematic structural diagram of a fourth chromatographic column analysis system in Example 1 of the present invention.
Figure 6:
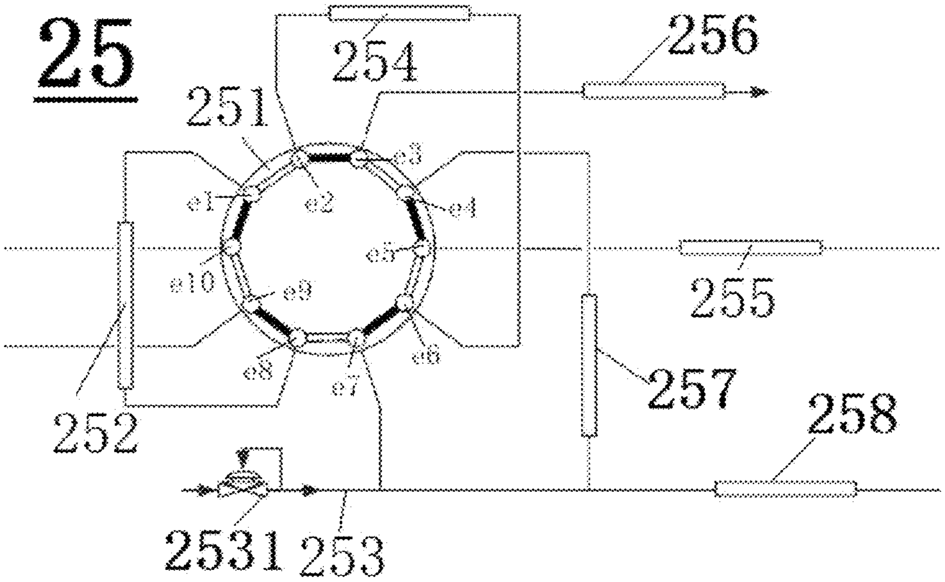
FIG. 6 shows a schematic structural diagram of a fifth chromatographic column analysis system in Example 1 of the present invention.

1 sample loading assembly; 11 natural gas intake tube; 12 natural gas discharge tube; 13 first quantitative tube connecting tube; 14 second quantitative tube connecting tube; 15 third quantitative tube connecting tube; 16 fourth quantitative tube connecting tube;

21 first chromatographic column analysis system; 211 first sample loading valve; 212 first quantitative tube; 213 first carrier gas tube; 214 sulfur column; 215 split/splitless inlet;

22 second chromatographic column analysis system; 221 second sample loading valve; 222 second quantitative tube; 223 second carrier gas tube; 224 first pre-separation column; 225 first chromatographic analytical column;

23 third chromatographic column analysis system; 231 third sample loading valve; 232 third quantitative tube; 233 third carrier gas tube; 234 second pre-separation column; 235 second chromatographic analytical column;

24 fourth chromatographic column analysis system; 241 fourth sample loading valve; 242 fourth quantitative tube; 243 fourth carrier gas tube; 244 third pre-separation column; 245 third chromatographic analytical column;

25 fifth chromatographic column analysis system; 251 fifth sample loading valve; 252 fifth quantitative tube; 253 fifth carrier gas tube; 254 fourth pre-separation column; 255 fourth chromatographic analytical column;

31 sulfur chemiluminescence detector; 32 flame ionization detector; 33 first thermal conductivity detector; 34 second thermal conductivity detector.

DESCRIPTION OF PREFERRED EMBODIMENTS

In order to make the objects, technical solutions and advantages of embodiments of the present invention clearer, the technical solutions in the embodiments of the present invention will be clearly and completely described below with reference to the drawings of the embodiments of the present invention. Apparently, the described examples are some rather than all of the examples of the present invention. Any other embodiments obtained by those of ordinary skill in the art based on the embodiments of the present invention without any creative effort shall fall within the scope of protection of the present invention. The principles and spirits of the present invention will be described in detail below with reference to several representative embodiments.

Example 1

As shown in FIGS. 1 to 6, this example provides a device for analyzing quality indicators of a natural gas product. The system comprises: a sample loading assembly 1, a first chromatographic column analysis system 21, a second chromatographic column analysis system 22, a third chromatographic column analysis system 23, a fourth chromatographic column analysis system 24, a fifth chromatographic column analysis system 25, a sulfur chemiluminescence detector 31, a flame ionization detector 32, a first thermal conductivity detector 33, and a second thermal conductivity detector 34.

The sample loading assembly 1 comprises a natural gas intake tube 11, a natural gas discharge tube 12, a first quantitative tube connecting tube 13, a second quantitative tube connecting tube 14, a third quantitative tube connecting tube 15, and a fourth quantitative tube connecting tube 16.

Each chromatographic column analysis system comprises a sample loading valve, and a quantitative tube, a carrier gas tube and a chromatographic column that are connected to the sample loading valve. Specifically, the first chromatographic column analysis system 21 comprises a first sample loading valve 211, a first quantitative tube 212, a first carrier gas tube 213, a sulfur column 214, and a split/splitless inlet 215. The first sample loading valve 211 is a six-way valve having a first setting position and a second setting position, and is provided with a first valve port a1, a second valve port a2, a third valve port a3, a fourth valve port a4, a fifth valve port a5, and a sixth valve port a6 in clockwise sequence; when the first sample loading valve 211 is in the first setting position, the sixth valve port a6 is connected to the first valve port a1, the second valve port a2 is connected to the third valve port a3, and the fourth valve port a4 is connected to the fifth valve port a5; when the first sample loading valve 211 is in the second setting position, the first valve port a1 is connected to the second valve port a2, the third valve port a3 is connected to the fourth valve port a4, and the fifth valve port a5 is connected to the sixth valve port a6; the first quantitative tube 212 has one end connected to the first valve port a1 and the other end connected to the fourth valve port a4, the first carrier gas tube 213 is connected to the second valve port a2, and the sulfur column 214 is connected to the third valve port a3; and the split/splitless inlet 215 is disposed in a connecting tubing between the sulfur column 214 and the third valve port a3. The sulfur column 214 enables separation of carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene. The first carrier gas tube 213 is provided with a flow control meter 2131.

The second chromatographic column analysis system 22 comprises a second sample loading valve 221, a second quantitative tube 222, a second carrier gas tube 223, a first pre-separation column 224, and a first chromatographic analytical column 225. The second sample loading valve 222 is a ten-way valve having a first setting position and a second setting position, and is provided with a first valve port b1, a second valve port b2, a third valve port b3, a fourth valve port b4, a fifth valve port b5, a sixth valve port b6, a seventh valve port b7, an eighth valve port b8, a ninth valve port b9 and a tenth valve port b10 in clockwise sequence; when the second sample loading valve 221 is in the first setting position, the tenth valve port b10 is connected to the first valve port b1, the second valve port b2 is connected to the third valve port b3, the fourth valve port b4 is connected to the fifth valve port b5, the sixth valve port b6 is connected to the seventh valve port b7, and the eighth valve port b8 is connected to the ninth valve port b9; when the second sample loading valve 221 is in the second setting position, the first valve port b1 is connected to the second valve port b2, the third valve port b3 is connected to the fourth valve port b4, the fifth valve port b5 is connected to the sixth valve port b6, the seventh valve port b7 is connected to the eighth valve port b8, and the ninth valve port b9 is connected to the tenth valve port b10; and the second quantitative tube 222 has one end connected to the first valve port b1 and the other end connected to the eighth valve port b8, the second carrier gas tube 223 is connected to each of the seventh valve port b7 and the fourth valve port b4, the first pre-separation column 224 has an inlet end connected to the second valve port b2 and an outlet end connected to the sixth valve port b6, and an inlet end of the first chromatographic analytical column 225 is connected to the fifth valve port b5. The first pre-separation column 224 enables separation of $C_6^+$ hydrocarbon components (including hydrocarbon components having 6 or more carbons) from $C_5^-$ hydrocarbon components (including hydrocarbon components having 5 or less carbons); and the first chromatographic analytical column 225 enables separation of propane, isobutane, n-butane, neopentane, isopentane, n-pentane. The second carrier gas tube 223 is provided with a flow control meter 2231; a damping tube 227 is disposed in a connecting tubing between the second carrier gas tube 223 and the fourth valve port b4; and a diverter valve 229 is disposed in a connecting tubing between the inlet end of the first chromatographic analytical column 225 and the fifth valve port b5.

The third chromatographic column analysis system 23 comprises a third sample loading valve 231, a third quantitative tube 232, a third carrier gas tube 233, a second pre-separation column 234, and a second chromatographic analytical column 235. The third sample loading valve 231 is a ten-way valve having a first setting position and a second setting position, and is provided with a first valve port c1, a second valve port c2, a third valve port c3, a fourth valve port c4, a fifth valve port c5, a sixth valve port c6, a seventh valve port c7, an eighth valve port c8, a ninth valve port c9 and a tenth valve port c10 in clockwise sequence; when the third sample loading valve 231 is in the first setting position, the tenth valve port c10 is connected to the first valve port c1, the second valve port c2 is connected to the third valve port c3, the fourth valve port c4 is connected to the fifth valve port c5, the sixth valve port c6 is connected to the seventh valve port c7, and the eighth valve port c8 is connected to the ninth valve port c9; when the third sample loading valve 231 is in the second setting position, the first valve port c1 is connected to the second valve port c2, the third valve port c3 is connected to the fourth valve port c4, the fifth valve port c5 is connected to the sixth valve port c6, the seventh valve port c7 is connected to the eighth valve port c8, and the ninth valve port c9 is connected to the tenth valve port c10; the third quantitative tube 232 has one end connected to the first valve port c1 and the other end connected to the eighth valve port c8, the third carrier gas tube 233 is connected to each of the seventh valve port c7 and the fourth valve port c4, the second pre-separation column 234 has an inlet end connected to the second valve port c2 and an outlet end connected to the sixth valve port c6, and an inlet end of the second chromatographic analytical column 235 is connected to the fifth valve port c5; and the third valve port c3 is used as a back-flushing exhaust port of the second pre-separation column 234. The second pre-separation column 234 enables separation of oxygen, nitrogen, methane and carbon monoxide from the natural gas (other hydrocarbon components in the natural gas can be back flushed out), and the second chromatographic analytical column 235 enables separation of oxygen, nitrogen, methane and carbon monoxide; the third carrier gas tube 233 is provided with a flow control meter 2331, and a damping tube 237 is disposed on a connecting tubing between the third carrier gas tube 233 and the fourth valve port c4; and a damping tube 236 is disposed on an external exhaust tubing connected to the third valve port c3.

The fourth chromatographic column analysis system 24 comprises a fourth sample loading valve 241, a fourth quantitative tube 242, a fourth carrier gas tube 243, a third pre-separation column 244, and a third chromatographic analytical column 245. The fourth sample loading valve 241 is a ten-way valve having a first setting position and a second setting position, and is provided with a first valve port d1, a second valve port d2, a third valve port d3, a fourth valve port d4, a fifth valve port d5, a sixth valve port d6, a seventh valve port d7, an eighth valve port d8, a ninth valve port d9, and a tenth valve port d10 in clockwise sequence; when the fourth sample loading valve 241 is in the first setting position, the tenth valve port d10 is connected to the first valve port d1, the second valve port d2 is connected to the third valve port d3, the fourth valve port d4 is connected to the fifth valve port d5, the sixth valve port d6 is connected to the seventh valve port d7, and the eighth valve port d8 is connected to the ninth valve port d9; when the fourth sample loading valve 241 is in the second setting position, the first valve port d1 is connected to the second valve port d2, the third valve port d3 is connected to the fourth valve port d4, the fifth valve port d5 is connected to the sixth valve port d6, the seventh valve port d7 is connected to the eighth valve port d8, and the ninth valve port d9 is connected to the tenth valve port d10; the fourth quantitative tube 242 has one end connected to the first valve port d1 and the other end connected to the eighth valve port d8, the fourth carrier gas tube 243 is connected to each of the seventh valve port d7 and the fourth valve port d4, the third pre-separation column 244 has an inlet end connected to the second valve port d2 and an outlet end connected to the sixth valve port d6, and an inlet end of the third chromatographic analytical column 245 is connected to the fifth valve port d5; and the third valve port d3 is used as a back-flushing exhaust port of the third pre-separation column 244. The third pre-separation column 244 enables separation of ethane and $CO_2$ from the natural gas, and the third chromatographic analytical column 245 enables separation of ethane and $CO_2$; the fourth carrier gas tube 243 is provided with a flow control meter 2431; a damping tube 247 is disposed on a connecting tubing between the fourth carrier gas tube 243 and the fourth valve port d4; and a damping tube 246 is disposed on an external exhaust tubing connected to the third valve port d3.

The fifth chromatographic column analysis system 25 comprises a fifth sample loading valve 251, a fifth quantitative tube 252, a fifth carrier gas tube 253, a fourth pre-separation column 254, and a fourth chromatographic analytical column 255. The fifth sample loading valve 251 is a ten-way valve having a first setting position and a second setting position, and is provided with a first valve port e1, a second valve port e2, a third valve port e3, a fourth valve port e4, a fifth valve port e5, a sixth valve port e6, a seventh valve port e7, an eighth valve port e8, a ninth valve port e9 and a tenth valve port e10 in clockwise sequence; when the fifth sample loading valve 251 is in the first setting position, the tenth valve port e10 is connected to the first valve port e1, the second valve port e2 is connected to the third valve port e3, the fourth valve port e4 is connected to the fifth valve port e5, the sixth valve port e6 is connected to the seventh valve port e7, and the eighth valve port e8 is connected to the ninth valve port e9; when the fifth sample loading valve 251 is in the second setting position, the first valve port e1 is connected to the second valve port e2, the third valve port e3 is connected to the fourth valve port e4, the fifth valve port e5 is connected to the sixth valve port e6, the seventh valve port e7 is connected to the eighth valve port e8, and the ninth valve port e9 is connected to the tenth valve port e10; the fifth quantitative tube 252 has one end connected to the first valve port e1 and the other end connected to the eighth valve port e8, the fifth carrier gas tube 253 is connected to each of the seventh valve port e7 and the fourth valve port e4, the fourth pre-separation column 254 has an inlet end connected to the second valve port e2 and an outlet end connected to the sixth valve port e6, and an inlet end of the fourth chromatographic analytical column 255 is connected to the fifth valve port e5; and the third valve port e3 is used as a back-flushing exhaust port of the fourth pre-separation column 254. The fourth pre-separation column 254 enables separation of helium and hydrogen from the natural gas (other hydrocarbon components in the natural gas can be back flushed out), and the fourth chromatographic analytical column 255 enables separation of helium and hydrogen; the fifth carrier gas tube 253 is provided with a flow control meter 2531; a damping tube 257 is disposed on a connecting tubing between the fifth carrier gas tube 253 and the fourth valve port e4; and a damping tube 256 is disposed on an external exhaust tubing connected to the third valve port e3. The first sample loading valve 211, the second sample loading valve 221, the third sample loading valve 231, the fourth sample loading valve 241, and the fifth sample loading valve 251 are connected in series via the first quantitative tube connection tube 13, the second quantitative tube connection tube 14, the third quantitative tube connection tube 15, and the fourth quantitative tube connection tube 16, and the natural gas intake tube 11 and the natural gas discharge tube 12 are connected to the first and last sample loading valves of the first sample loading valve 211, the second sample loading valve 221, the third sample loading valve 231, the fourth sample loading valve 241, and the fifth sample loading valve 251 that are connected in series, thereby connecting the quantitative tubes in series. Specifically, the sixth valve port a6 of the first sample loading valve 211 is connected to the natural gas intake tube 11, the fifth valve port a5 of the first sample loading valve 211 is connected to the first quantitative tube connecting tube 13, the tenth valve port b10 of the second sample loading valve 221 is connected to the first quantitative tube connecting tube 13, the ninth valve port b9 of the second sample loading valve 221 is connected to the second quantitative tube connecting tube 14, the tenth valve port c10 of the third sample loading valve 231 is connected to the second quantitative tube connection tube 14, the ninth valve port c9 of the third sample loading valve 231 is connected to the third quantitative tube connection tube 15, the tenth valve port d10 of the fourth sample loading valve 241 is connected to the third quantitative tube connection tube 15, the ninth valve port d9 of the fourth sample loading valve 241 is connected to the fourth quantitative tube connection tube 16, the tenth valve port e10 of the fifth sample loading valve 251 is connected to the fourth quantitative tube connection tube 16, and the ninth valve port e9 of the fifth sample loading valve 251 is connected to the natural gas discharge tube 12. The natural gas intake tube 11 is provided with a control valve 111; the second quantitative tube connecting tube 14 is provided with a control valve 141; the third quantitative tube connection tube 15 is provided with a control valve 151; and the chromatographic column analysis systems are connected to corresponding detectors, respectively. Specifically, the sulfur chemiluminescence detector 31 is connected to an outlet end of the sulfur column 214, the third valve port b3 of the second sample loading valve 221 and the first chromatographic analytical column 225 are each connected to the flame ionization detector 32, the second chromatographic analytical column 235 is connected to the first thermal conductivity detector 33, the third chromatographic analytical column 245 is connected to the first thermal conductivity detector 33, and the fourth chromatographic analytical column 255 and the fifth carrier gas tube 253 are each connected to the second thermal conductivity detector 34. A diverter valve 228 and a damping tube 226 are disposed in a connecting tubing between the third valve port b3 of the second sample loading valve 221 and the flame ionization detector 32; and a damping tube 258 is disposed in a connecting tubing between the fifth carrier gas tube 253 and the second thermal conductivity detector 34.

The first chromatographic column analysis system 21 is configured for separating carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene from the natural gas, and the first chromatographic column analysis system 21 is connected to the sulfur chemiluminescence detector 31 to analyze contents of the carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene in the natural gas.

The second chromatographic column analysis system 22 is configured for separating the hydrocarbons having $C_3$ and higher from the natural gas, and the second chromatographic column analysis system 22 is connected to the flame ionization detector 32 to analyze contents of the hydrocarbons having $C_3$ and higher in the natural gas.

The third chromatographic column analysis system 23 is configured for separating oxygen, nitrogen, methane and carbon monoxide from the natural gas, and the third chromatographic column analysis system 23 is connected to the first thermal conductivity detector 33 to analyze contents of the oxygen, nitrogen, methane and carbon monoxide in the natural gas.

The fourth chromatographic column analysis system 24 is configured for separating carbon dioxide and ethane from the natural gas, and the fourth chromatographic column analysis system 24 is connected to the first thermal conductivity detector 33 to analyze contents of the carbon dioxide and ethane in the natural gas.

The fifth chromatographic column analysis system 25 is configured for separating helium and hydrogen from the natural gas, and the fifth chromatographic column analysis system 25 is connected to the second thermal conductivity detector 34 to analyze contents of the helium and hydrogen content in the natural gas.

Specifically, the sulfur column 214 is a DB-Sulfur SCD chromatographic column. The sulfur column 214 has dimensions of 60 m in length and 0.32 mm in diameter, with a capillary column liquid film thickness of 4.2 μm.

The volume of the first quantitative tube 212 is 1 mL.

Specifically, the first pre-separation column 224 is an OV-1 pre-separation column; a packing material of the first pre-separation column 224 comprises 80-100 mesh Celite 545 and silicone OV-1, where the content of silicone OV-1 is 10% based on the mass of Celite 545 (Silicone OV-1 10% Celite 545 80/100 mesh); and the first pre-separation column 224 has dimensions of 1.6 mm in outer diameter, 1.0 mm in inner diameter, and 1.0 m in length.

The first chromatographic analytical column 225 is an HP-Al/S chromatographic column. The first chromatographic analytical column 225 has dimensions of 50 m in length and 0.53 mm in diameter, with a liquid film thickness of 15 μm.

The volume of the second quantitative tube 222 is 0.1 mL.

Specifically, the second pre-separation column 234 is a Porapak N column; a packing material of the second pre-separation column 234 has a mesh number of 80-100; and the second pre-separation column 234 has dimensions of 3.2 mm in outer diameter, 2.1 mm in inner diameter, and 1.0 m in length.

The second chromatographic analytical column 235 is an MS-13X molecular sieve column. The second chromatographic analytical column 235 has dimensions of 3.2 mm in outer diameter, 2.1 mm in inner diameter, and 5.0 m in length.

The volume of the third quantitative tube 232 is 1 mL.

Specifically, the third pre-separation column 244 is a Porapak N column; a packing material of the third pre-separation column 244 has a mesh number of 80-100; and the third pre-separation column 244 has dimensions of 3.2 mm in outer diameter, 2.1 mm in inner diameter, and 1.0 m in length.

The third chromatographic analytical column 245 is a Porapak N column; a packing material of the third chromatographic analytical column 245 has a mesh number of 80-100; and the third chromatographic analytical column 245 has dimensions of 3.2 mm in outer diameter, 2.1 mm in inner diameter, and 2.0 m in length.

The volume of the fourth quantitative tube 242 is 1 mL.

Specifically, the fourth pre-separation column 254 is a Porapak N column; a packing material of the fourth pre-separation column 254 has a mesh number of 80-100; and the fourth pre-separation column 254 has dimensions of 3.2 mm in outer diameter, 2.1 mm in inner diameter, and 1.0 m in length.

The fourth chromatographic analytical column 255 is an MS-5 A molecular sieve column, and a packing material of the fourth chromatographic analytical column 255 has a mesh number of 60-80. The fourth chromatographic analytical column 255 has dimensions of 3.2 mm in outer diameter, 2.1 mm in inner diameter, and 3.0 m in length.

The volume of the fifth quantitative tube 252 is 5 mL.

Specifically, the device further comprises a programmed temperature ramp apparatus in which the sulfur column 214 and the first chromatographic analytical column 225 are disposed.

Specifically, the device further comprises a thermostat in which the second chromatographic analytical column 235, the third chromatographic analytical column 245, and the fourth chromatographic analytical column 255 are disposed.

Example 2

Further provided in this example is a method for analyzing quality indicators of a natural gas product. The method is implemented using the device for analyzing quality indicators of a natural gas product according to Example 1. The method comprises the following steps.

In step S1, a sample is injected into the quantitative tubes of the first chromatographic column analysis system 21, the second chromatographic column analysis system 22, the third chromatographic column analysis system 23, the fourth chromatographic column analysis system 24, and the fifth chromatographic column analysis system 25 such that each of the quantitative tubes is filled with a natural gas sample. Specifically, the first sample loading valve 211, the second sample loading valve 221, the third sample loading valve 231, the fourth sample loading valve 241 and the fifth sample loading valve 251 are each switched to the first setting position, a natural gas product is introduced from the natural gas intake tube 11 to the first sample loading valve 211, and the natural gas product passes through the first quantitative tube 212, the second quantitative tube 232, the third quantitative tube 232, the fourth quantitative tube 242 and the fifth quantitative tube 252 in sequence, and is then discharged from the natural gas discharge tube 12; and the first quantitative tube 212, the second quantitative tube 232, the third quantitative tube 232, the fourth quantitative tube 242, and the fifth quantitative tube 252 entrap part of the natural gas product as a natural gas sample.

Figure 7:
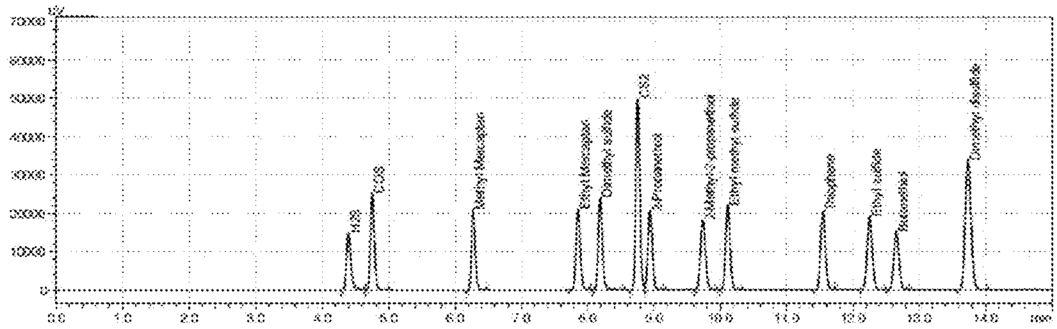
FIG. 7 shows a first detection chromatogram in Example 2 of the present invention.

In step S2, in the first chromatographic column analysis system 21, the first carrier gas tube 213 is used to deliver the carrier gas, the natural gas sample in the first quantitative tube 212 is delivered to the sulfur column 214 under the driving of the carrier gas to separate the sulfides, and the separated components are delivered to a sulfur chemiluminescence detector 31 such that the sulfides in the natural gas sample are detected so as to obtain a first detection chromatogram. Specifically, the first sample loading valve 211 in the first chromatographic column analysis system 21 is switched to the second setting position, a carrier gas is introduced into the first chromatographic column analysis system 21 from the first carrier gas tube 213 at a flow rate of 3 mL/min, enters the first quantitative tube 212 through the second valve port a2 and the first valve port a1 in sequence, and drives the natural gas sample in the first quantitative tube 212 to flow into the sulfur column 214 after passing through the fourth valve port a4, the third valve port a3 and the split/splitless inlet 215 in sequence, so as to be separated in the sulfur column 214; and carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene are sequentially discharged from the sulfur column 214 into the sulfur chemiluminescence detector 31 for detection, so as to obtain the first detection chromatogram. See FIG. 7 for the first detection chromatogram.

The carrier gas is helium.

The sulfur column 214 is maintained (for 3 min in this example) at 40° C. until carbonyl sulfur exits the sulfur column, and the sulfur column is then heated at a rate of 15° C./min to, and maintained (for 6 min in this example) at, 130° C. until the first detection chromatogram is obtained.

The sulfur chemiluminescence detector 31 has a sample loading temperature of 200° C. and a reaction temperature of 850° C., the sulfur chemiluminescence detector 31 has a split ratio of 10:1, and flow rates of reaction gases in the sulfur chemiluminescence detector 31 are 80 mL/min of hydrogen ($H_2$), 40 mL/min of nitrogen ($N_2$), 10 mL/min of oxygen ($O_2$), and 25 mL/min of ozone ($O_3$).

Figure 8:
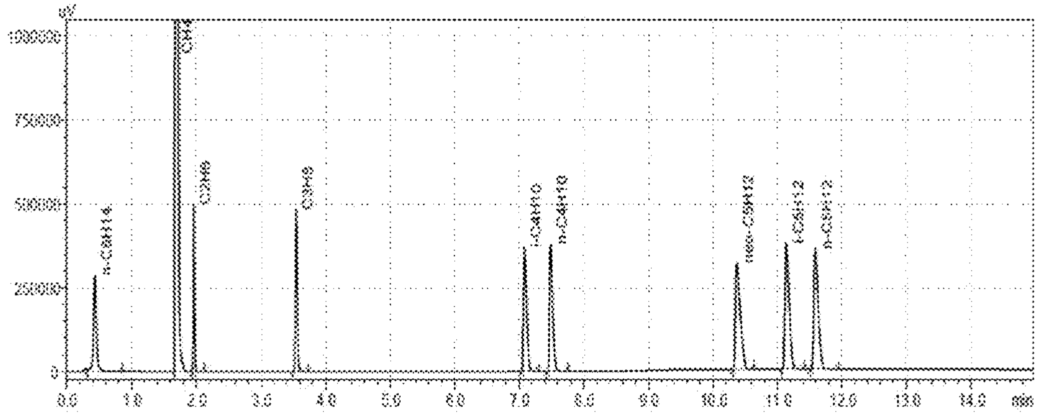
FIG. 8 shows a second detection chromatogram in Example 2 of the present invention.

In step S3, in the second chromatographic column analysis system 22, the second carrier gas tube 223 is used to deliver the carrier gas, and the first pre-separation column 224 and the first chromatographic analytical column 225 are used in sequence to perform separation on the natural gas sample in the second quantitative tube 222 under the driving of the carrier gas; when $C_5^-$ components in the natural gas sample exit the first pre-separation column 224 and enter the first chromatographic analytical column 225, the carrier gas is transferred to the outlet end of the first pre-separation column 224, the inlet end of the first pre-separation column 225 is connected to the flame ionization detector 32, and under the driving of the carrier gas, $C_6^+$ hydrocarbon components in the first pre-separation column 224 are back flushed to the flame ionization detector 32 for detection; after the back flushing is completed, the carrier gas is transferred to the inlet end of the first chromatographic analytical column 224, and under the driving of the carrier gas, $C_3^-$ hydrocarbon components separated by the first chromatographic analytical column 225 sequentially enter the flame ionization detector 32 for detection, so as to obtain the second detection chromatogram. Specifically, the second sample loading valve 221 in the second chromatographic column analysis system 22 is switched to the second setting position, the carrier gas is introduced into the second chromatographic column analysis system 22 from the second carrier gas tube 223 at a pressure of 500 kPa, enters the second quantitative tube 222 through the seventh valve port b7 and the eighth valve port b8 in sequence, and drives the natural gas sample in the second quantitative tube 222 to flow into the first pre-separation column 224 after passing through the first valve port b1 and the second valve port b2 in sequence, so as to be pre-separated in the first pre-separation column 224; and propane, isobutane, n-butane, neopentane, isopentane, and n-pentane are sequentially discharged from the first pre-separation column 224, and then enter the first chromatographic analytical column 225 for further separation after passing through the sixth valve port b6 and the fifth valve port b5 in sequence under the driving of the carrier gas, so that the time difference in separation of the components is increased. After the $C_5^-$ components exit the first pre-separation column 224 and enter the first chromatographic analytical column 225, the second sample loading valve 221 of the second chromatographic column analysis system 22 is switched to the first setting position. The carrier gas is introduced from the second carrier gas tube 223 at a pressure of 500 kPa, and enters the first pre-separation column 224 from the outlet end of the first pre-separation column 224 through the seventh valve port b7 and the sixth valve port b6 in sequence, and the $C_6^+$ hydrocarbon components in the first pre-separation column 224 are flushed out of the first pre-separation column 224, and enter the flame ionization detector 32 through the second valve port b2 and the third valve port b3 for detection. After the flame ionization detector 32 monitors a hexane combined peak, a flow direction of the carrier gas is adjusted. The carrier gas is introduced from the second carrier gas tube 223 at a pressure of 500 kPa, and enters the first chromatographic analytical column 225 after passing through the fourth valve port b4 and the fifth valve port b5 in sequence. Under the driving of the carrier gas, the propane, isobutane, n-butane, neopentane, isopentane, and n-pentane sequentially exit the first chromatographic analytical column 225 and enter the flame ionization detector 32 for detection so as to obtain the second detection chromatogram. See FIG. 8 for the second detection chromatogram.

The carrier gas is helium.

The first chromatographic analytical column 225 is maintained (for 3 min in this example) at 40° C. until the hexane combined peak is monitored, and the first chromatographic analytical column is then heated at a rate of 15° C./min to, and maintained (for 6 min in this example) at, 130° C. until the second detection chromatogram is obtained.

The temperature of the flame ionization detector 32 is 200° C., and flow rates of reaction gases of the flame ionization detector 32 are 32 mL/min of hydrogen ($H_2$), 200 mL/min of air, and 20 mL/min of make-up gas (Make-up).

Figure 9:
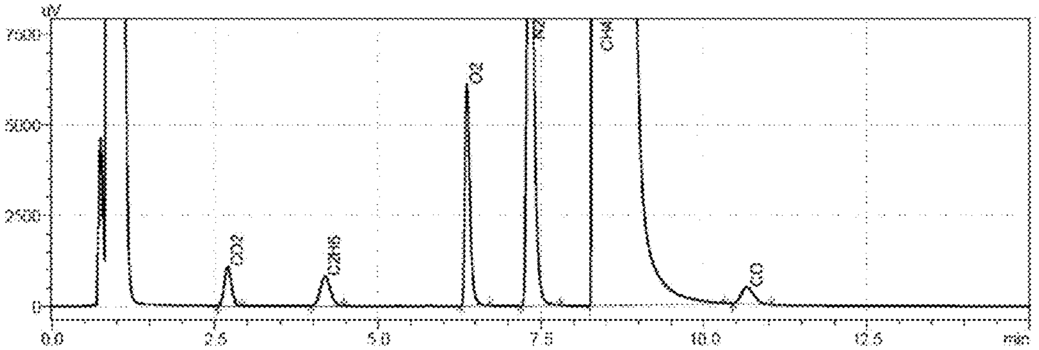
FIG. 9 shows third and fourth detection chromatograms in Example 2 of the present invention.

In step S4, in the third chromatographic column analysis system 23, the third carrier gas tube 233 is used to deliver the carrier gas, and the second pre-separation column 234 and the second chromatographic analytical column 235 are used to perform separation on the natural gas sample in the third quantitative tube 232 under the driving of the carrier gas; after the oxygen, nitrogen, methane and carbon monoxide components in the natural gas sample exit the second pre-separation column 234 and enter the second chromatographic analytical column 235, transferring the carrier gas to the outlet end of the second pre-separation column 234, and the remaining components in the second pre-separation column 235 are back flushed out of the third chromatographic column analysis system 23 under the driving of the carrier gas; and after the back flushing is completed, the carrier gas is transferred to the inlet end of the second chromatographic analytical column 235, and under the driving force of the carrier gas, the oxygen, nitrogen, methane and carbon monoxide components separated by the second chromatographic analytical column 235 sequentially enter the first thermal conductivity detector 33 for detection, so as to obtain the third detection chromatogram. Specifically, the third sample loading valve 231 in the third chromatographic column analysis system 23 is switched to the second setting position, the carrier gas is introduced into the third chromatographic column analysis system 23 from the third carrier gas tube 233 at a pressure of 500 kPa, enters the third quantitative tube 232 through the seventh valve port c7 and the eighth valve port c8 in sequence, and drives the natural gas sample in the third quantitative tube 232 to flow into the second pre-separation column 234 after passing through the first valve port c1 and the second valve port c2 in sequence, so as to be pre-separated in the second pre-separation column 234; and oxygen, nitrogen, methane and carbon monoxide are sequentially discharged from the second pre-separation column 234, and then enter the second chromatographic analytical column 235 for further separation after passing through the sixth valve port c6 and the fifth valve port c5 in sequence under the driving of the carrier gas, so that the time difference in separation of the components is increased. After the oxygen, nitrogen, methane and carbon monoxide components exit the second pre-separation column 234 and enter the second chromatographic analytical column 235, the third sample loading valve 231 of the third chromatographic column analysis system 23 is switched to the first setting position. The carrier gas is introduced from the third carrier gas tube 233 at a pressure of 500 kPa, and enters the second pre-separation column 234 from the outlet end of the second pre-separation column 234 through the seventh valve port c7 and the sixth valve port c6 in sequence, and the remaining components in the second pre-separation column 234 are flushed out of the third chromatographic column analysis system 23. A flow direction of the carrier gas is then adjusted. The carrier gas is introduced from the third carrier gas tube 233 at a pressure of 500 kPa, and enters the second chromatographic analytical column 235 after passing through the fourth valve port c4 and the fifth valve port c5 in sequence, and the oxygen, nitrogen, methane and carbon monoxide sequentially exit the second chromatographic analytical column 235 under the driving of the carrier gas and enter the first thermal conductivity detector 33 for detection so as to obtain the third detection chromatogram. See FIG. 9 for the third detection chromatogram (the third detection chromatogram and the fourth detection chromatogram being combined into one detection chromatogram).

The carrier gas is helium.

The column temperature of the second chromatographic analytical column is 60° C.

The temperature of the first thermal conductivity detector 33 is 150° C., and the first thermal conductivity detector 33 has an operating current of 120 mA, and is cathodic in polarity.

In step S5, in the fourth chromatographic column analysis system 24, the fourth carrier gas tube 243 is used to deliver the carrier gas, and the third pre-separation column 244 and the third chromatographic analytical column 245 are used to perform separation on the natural gas sample in the fourth quantitative tube 242 under the driving of the carrier gas; after carbon dioxide and ethane components in the natural gas sample exit the third pre-separation column 244 and enter the third chromatographic analytical column 245, the carrier gas is transferred to the outlet end of the third pre-separation column 244, and the remaining components in the third pre-separation column 245 are back flushed out of the fourth chromatographic column analysis system 24 under the driving of the carrier gas; and after the back flushing is completed, the carrier gas is transferred to the inlet end of the third chromatographic analytical column 245, and under the driving of the carrier gas, the carbon dioxide and ethane components separated by the third chromatographic analytical column 245 sequentially enter the first thermal conductivity detector 33 for detection, so as to obtain a fourth detection chromatogram. Specifically, the fourth sample loading valve 241 in the fourth chromatographic column analysis system 24 is switched to the second setting position, the carrier gas is introduced into the fourth chromatographic column analysis system 24 from the fourth carrier gas tube 243 at a pressure of 350 kPa, enters the fourth quantitative tube 242 through the seventh valve port d7 and the eighth valve port d8 in sequence, and drives the natural gas sample in the fourth quantitative tube 242 to flow into the third pre-separation column 244 after passing through the first valve port d1 and the second valve port d2 in sequence, so as to be pre-separated in the third pre-separation column 244; and carbon dioxide and ethane are sequentially discharged from the third pre-separation column 244, and then enter the third chromatographic analytical column 245 for further separation after passing through the sixth valve port d6 and the fifth valve port d5 in sequence under the driving of the carrier gas, so that the time difference in separation of the components is increased. After the carbon dioxide and ethane components exit the third pre-separation column 244 and enter the third chromatographic analytical column 245, the fourth sample loading valve 241 of the third chromatographic column analysis system 23 is switched to the first setting position. The carrier gas is introduced from the fourth carrier gas tube 243 at a pressure of 350 kPa, and enters the third pre-separation column 244 from the outlet end of the third pre-separation column 244 through the seventh valve port d7 and the sixth valve port d6 in sequence, and the remaining components in the third pre-separation column 244 are flushed out of the third chromatographic column analysis system 23. A flow direction of the carrier gas is then adjusted. The carrier gas is introduced from the fourth carrier gas tube 243 at a pressure of 350 kPa, and enters the third chromatographic analytical column 245 after passing through the fourth valve port d4 and the fifth valve port d5 in sequence, and the carbon dioxide and ethane sequentially exit the third chromatographic analytical column 245 under the driving of the carrier gas and enter the first thermal conductivity detector 33 for detection so as to obtain the fourth detection chromatogram. See FIG. 9 for the fourth detection chromatogram (the third detection chromatogram and the fourth detection chromatogram being combined into one detection chromatogram)

The carrier gas is helium.

The column temperature of the second chromatographic analytical column is 60° C.

The temperature of the first thermal conductivity detector 33 is 150° C., and the first thermal conductivity detector 33 has an operating current of 120 mA, and is cathodic in polarity.

Figure 10:
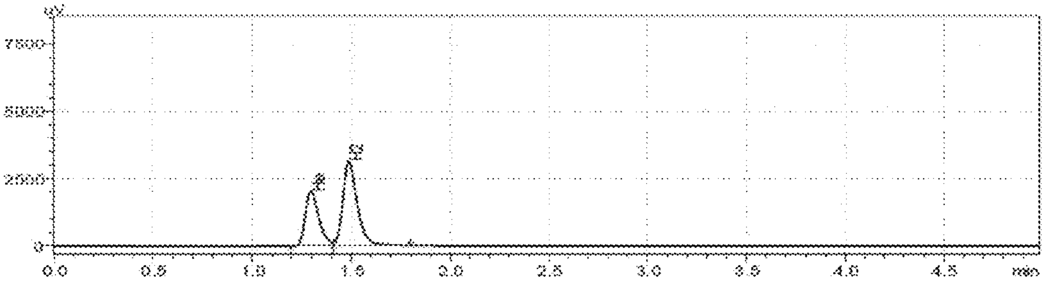
FIG. 10 shows a fifth detection chromatogram in Example 2 of the present invention.
Figure 11:
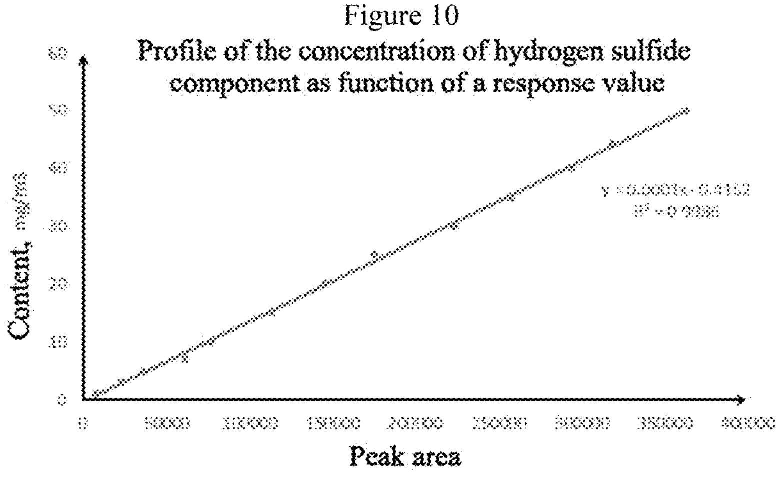
FIG. 11 shows a standard curve of hydrogen sulfide content.
Figure 12:
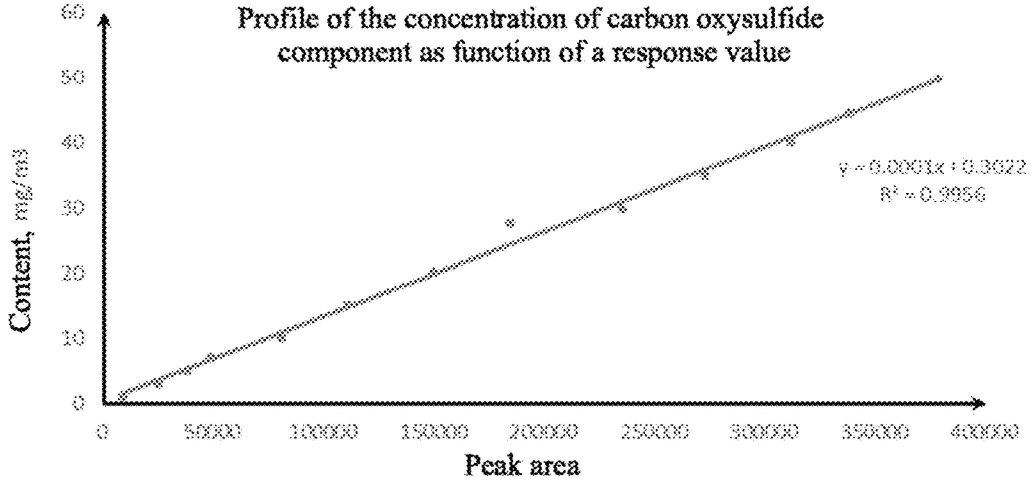
FIG. 12 shows a standard curve of carbon oxysulfide content.
Figure 13:
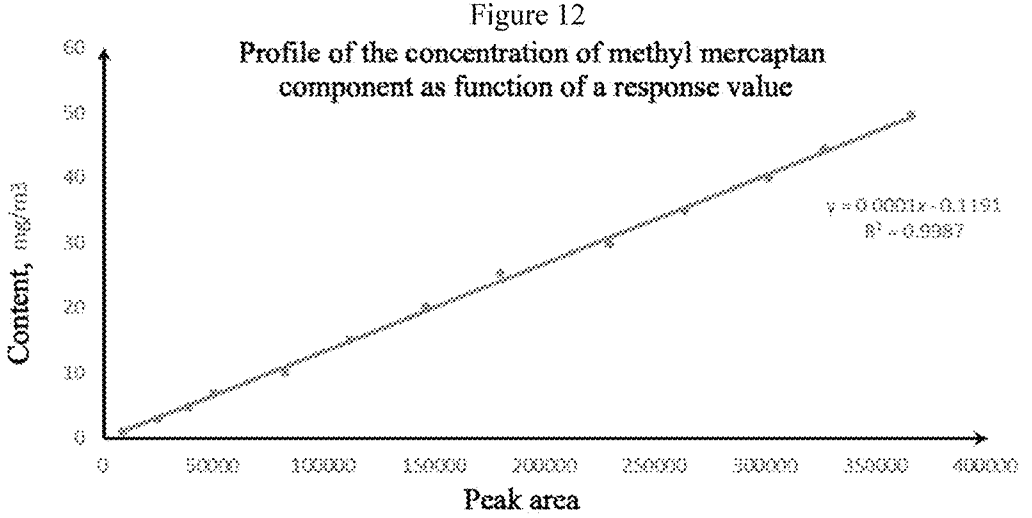
FIG. 13 shows a standard curve of methyl mercaptan content.
Figure 14:
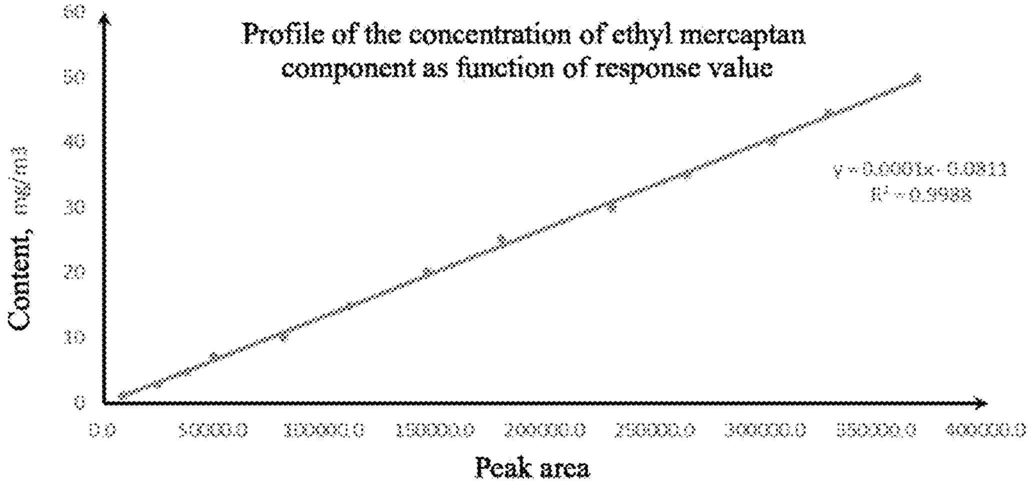
FIG. 14 shows a standard curve of ethyl mercaptan content.
Figure 15:
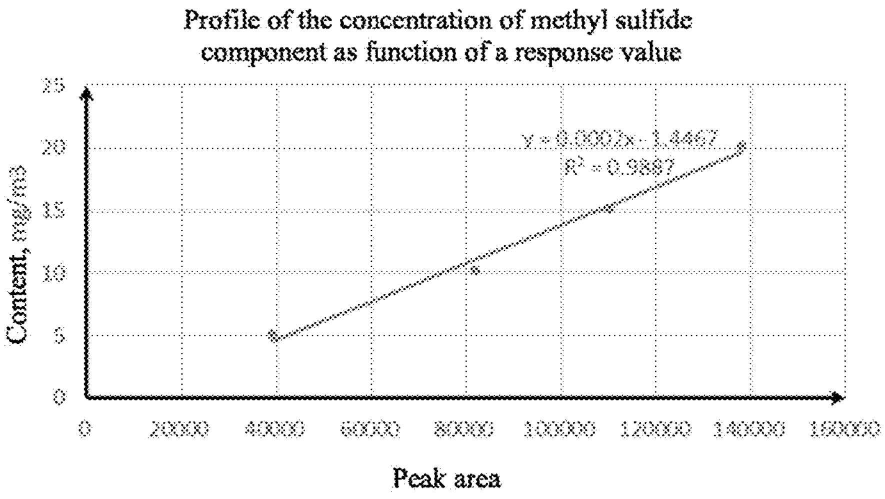
FIG. 15 shows a standard curve of methyl sulfide content.
Figure 16:
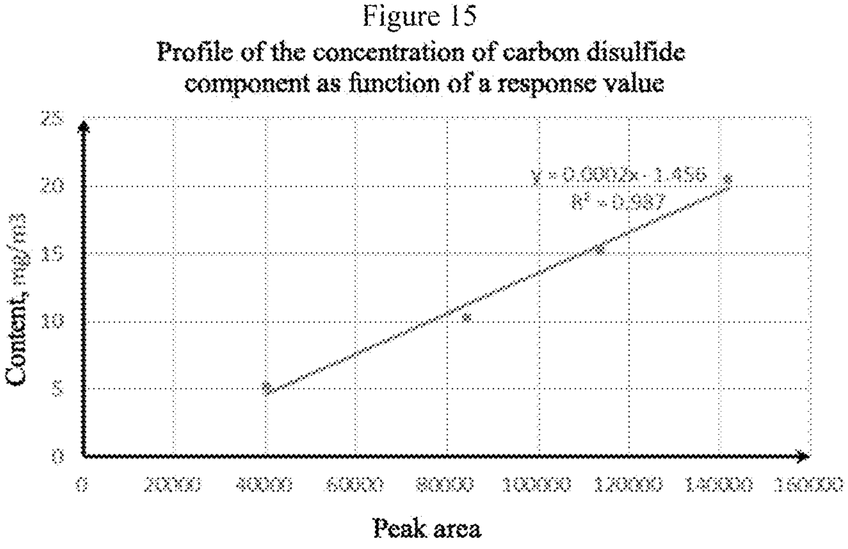
FIG. 16 shows a standard curve of carbon disulfide content.
Figure 17:
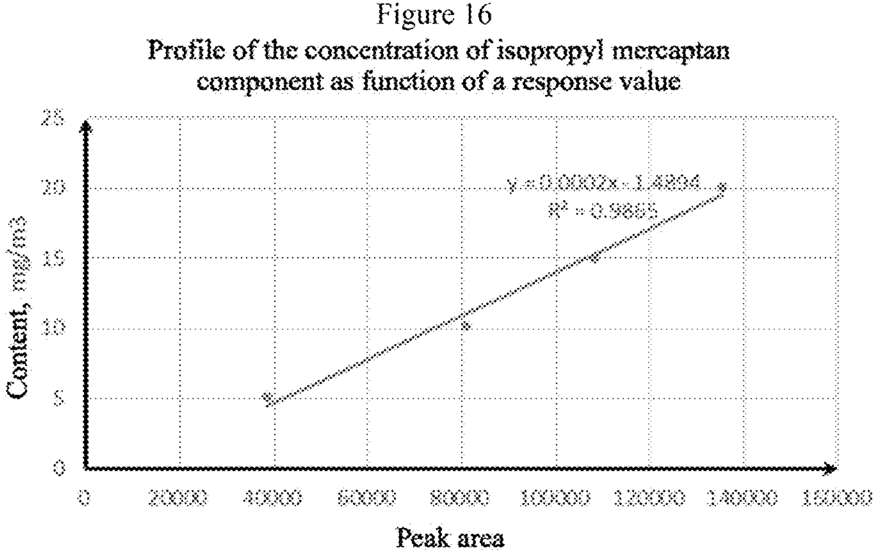
FIG. 17 shows a standard curve of isopropyl mercaptan content.
Figure 18:
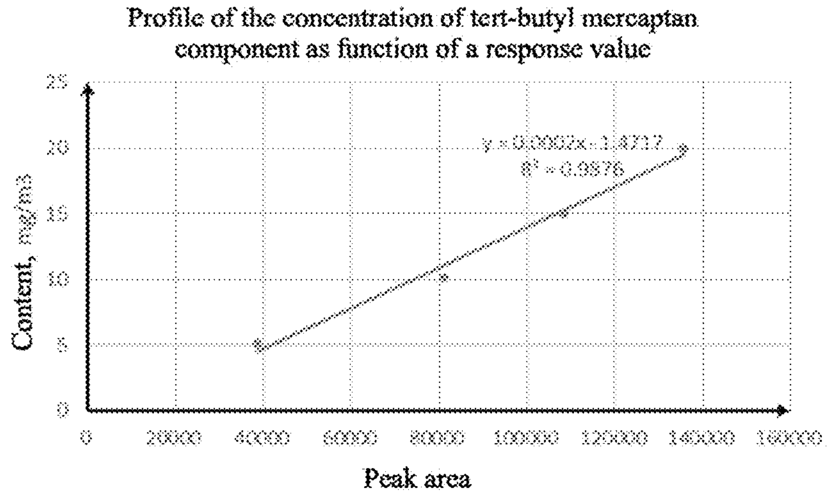
FIG. 18 shows a standard curve of tert-butyl mercaptan content.
Figure 19:
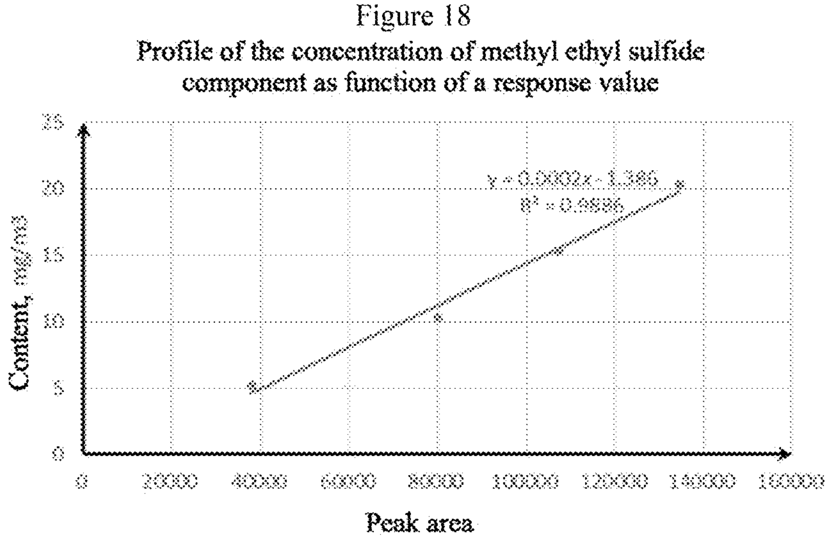
FIG. 19 shows a standard curve of methyl ethyl sulfide content.
Figure 20:
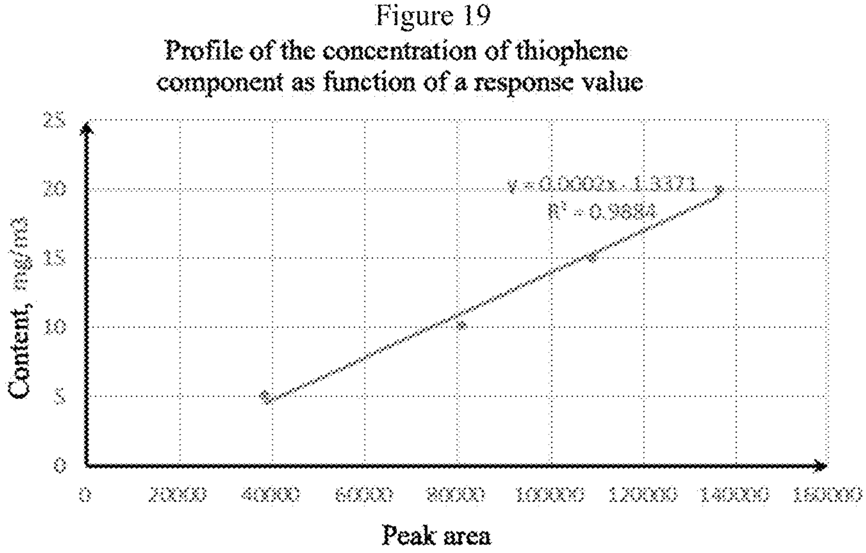
FIG. 20 shows a standard curve of thiophene content.
Figure 21:
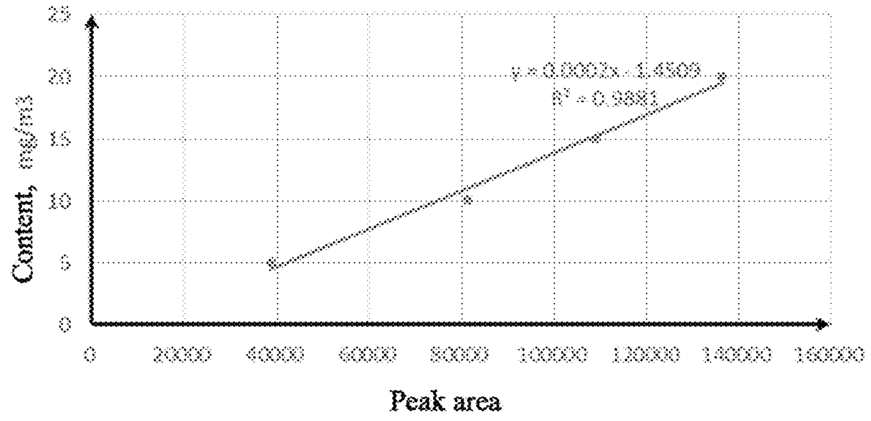
FIG. 21 shows a standard curve of ethyl sulfide content.
Figure 22:
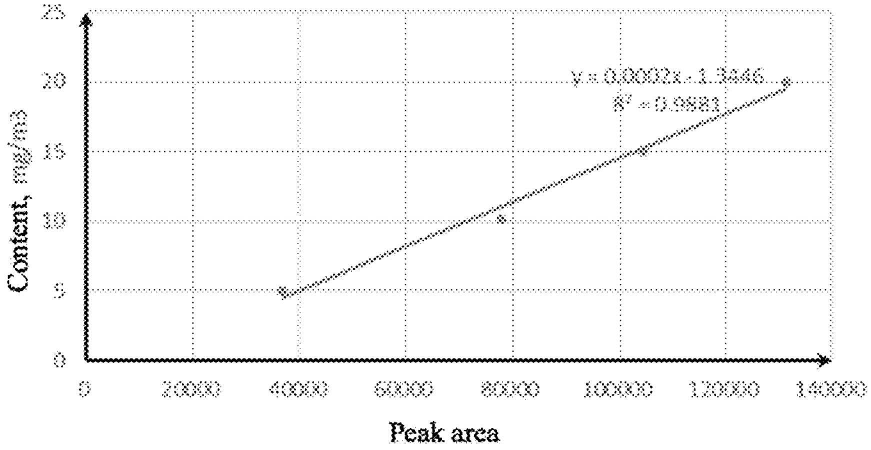
FIG. 22 shows a standard curve of n-butyl mercaptan content.
Figure 23:
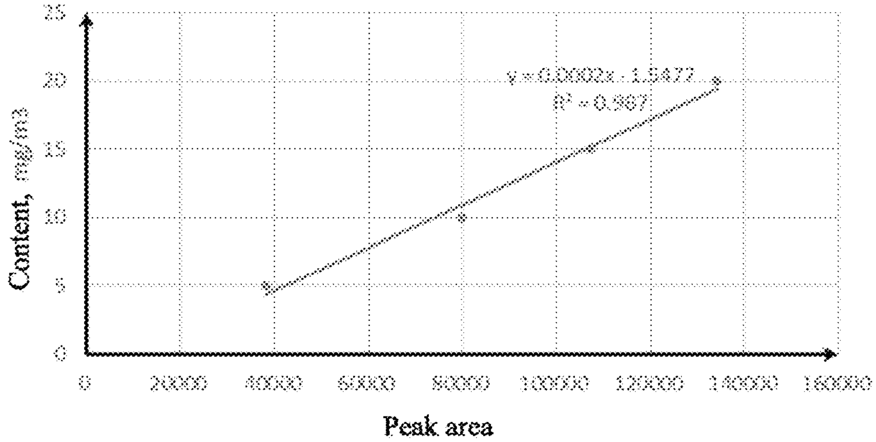
FIG. 23 shows a standard curve of dimethyl disulfide content.
Figure 24:
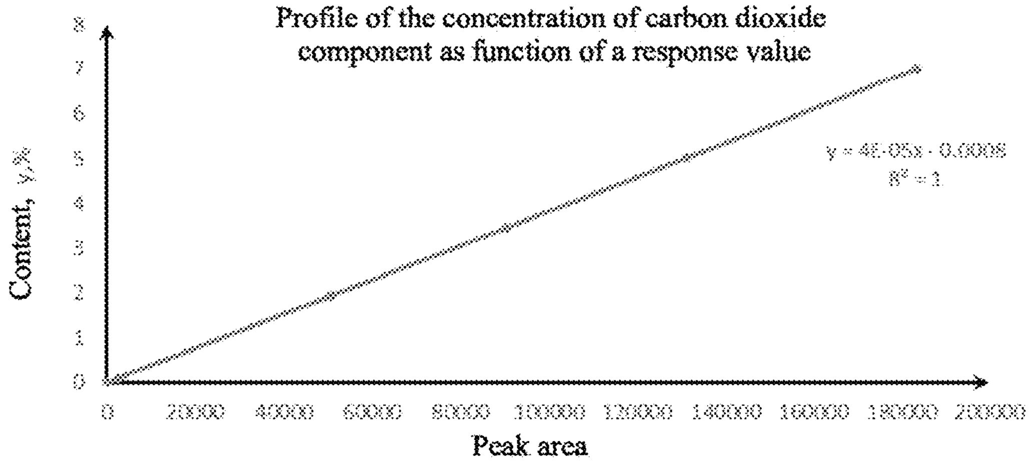
FIG. 24 shows a standard curve of carbon dioxide content.
Figure 25:
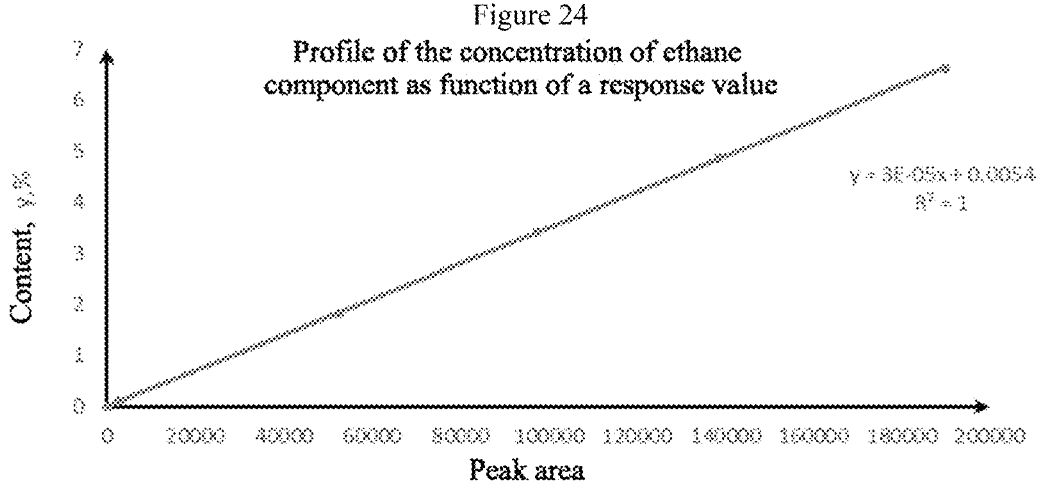
FIG. 25 shows a standard curve of ethane content.
Figure 26:
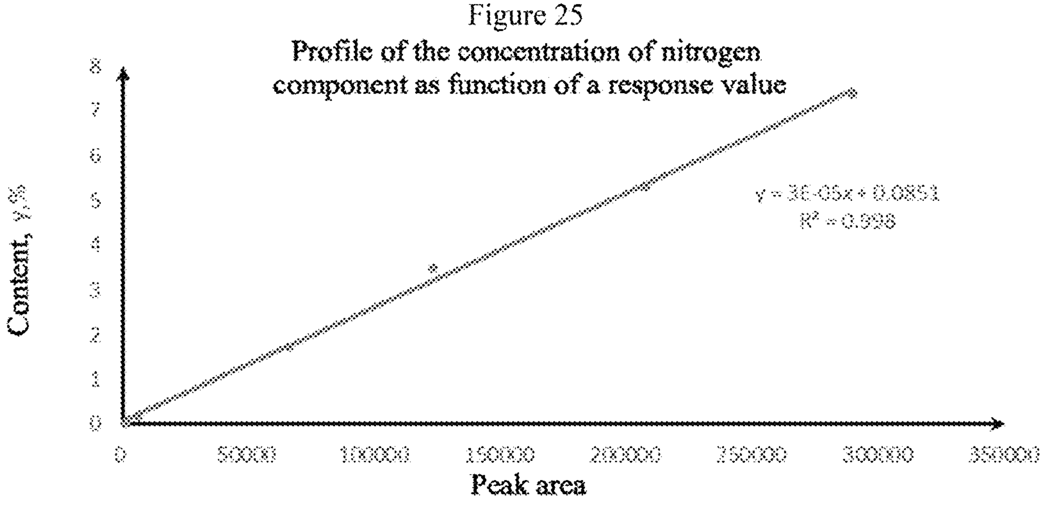
FIG. 26 shows a standard curve of nitrogen content.
Figure 27:
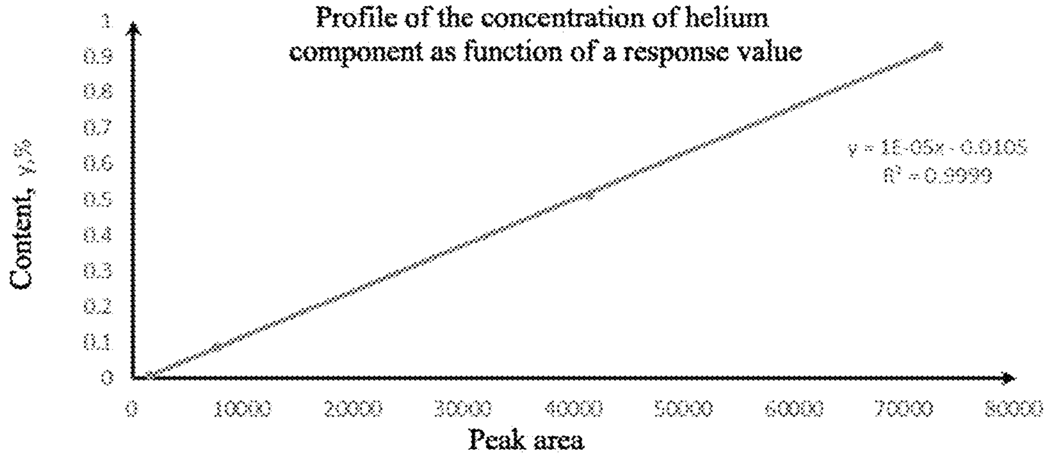
FIG. 27 shows a standard curve of helium content.
Figure 28:
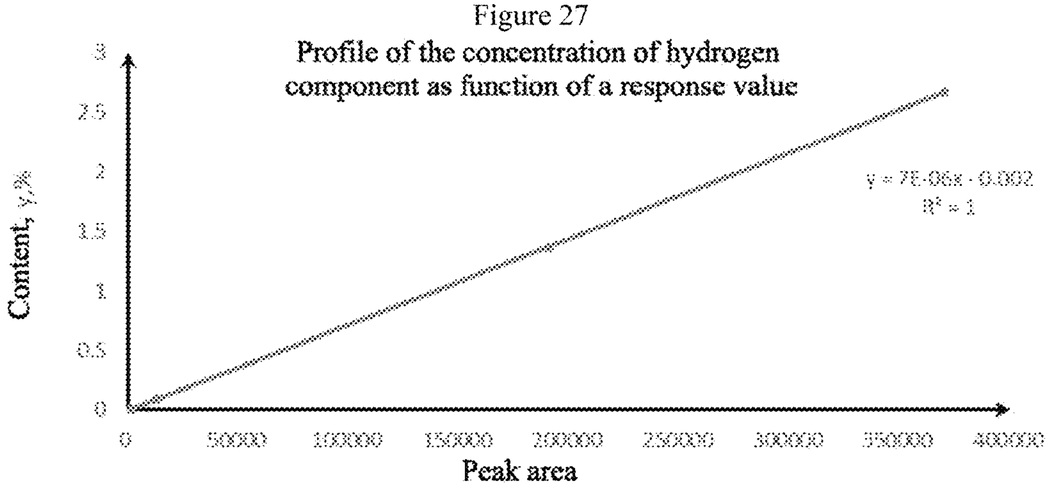
FIG. 28 shows a standard curve of hydrogen content.
Figure 29:
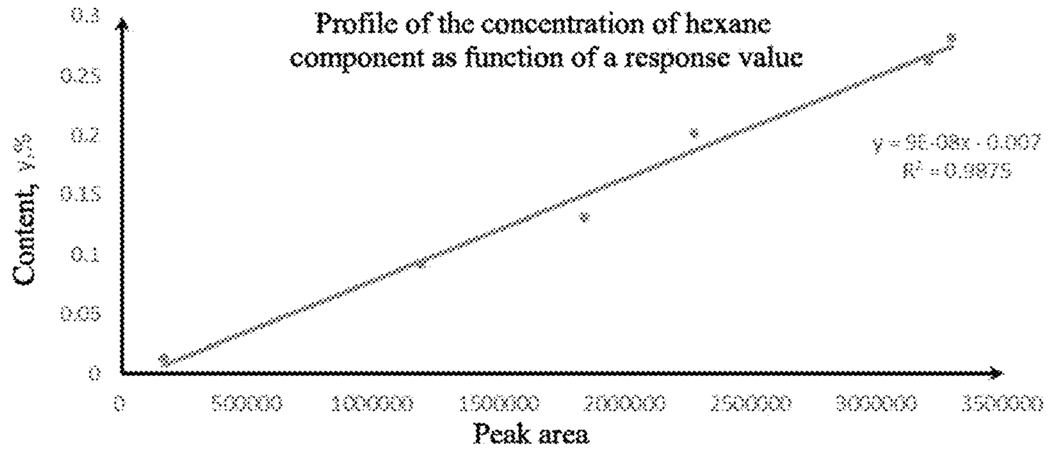
FIG. 29 shows a standard curve of hexane content.
Figure 30:
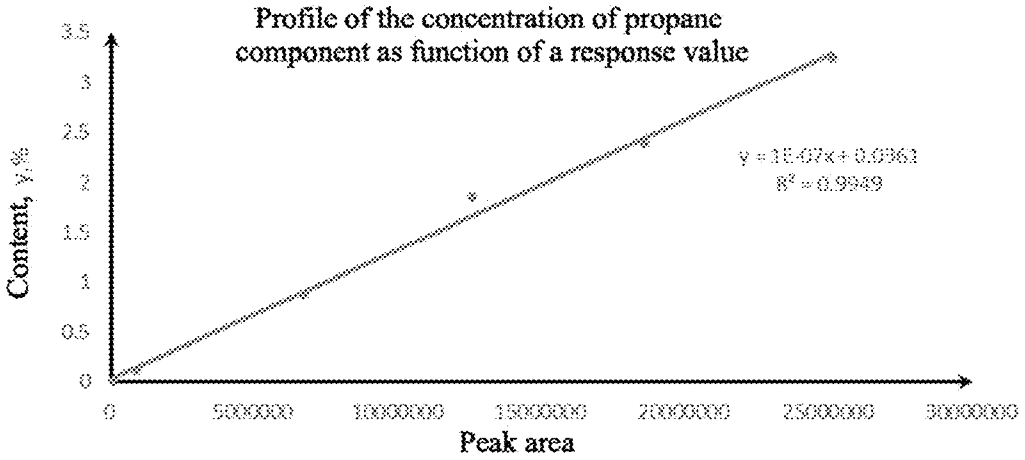
FIG. 30 shows a standard curve of propane content.
Figure 31:
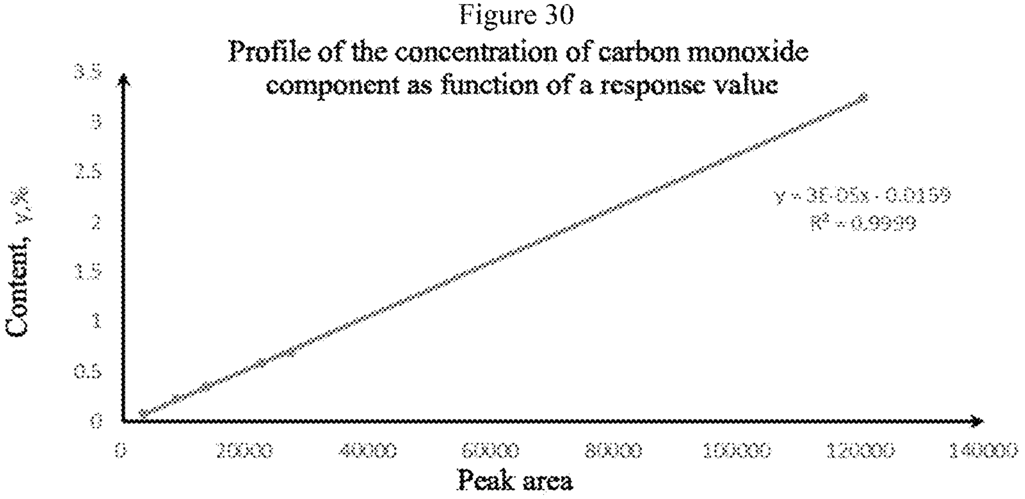
FIG. 31 shows a standard curve of carbon monoxide content.
Figure 32:
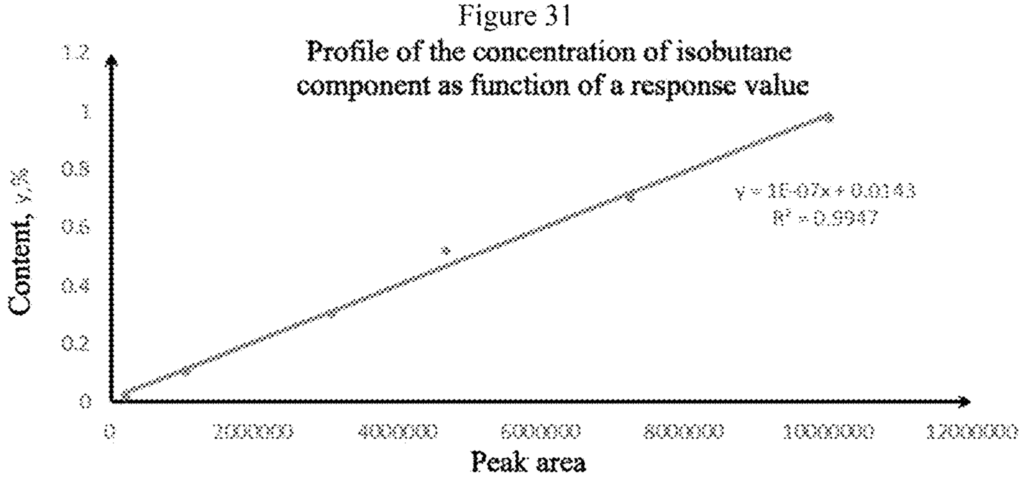
FIG. 32 shows a standard curve of isobutane content.
Figure 33:
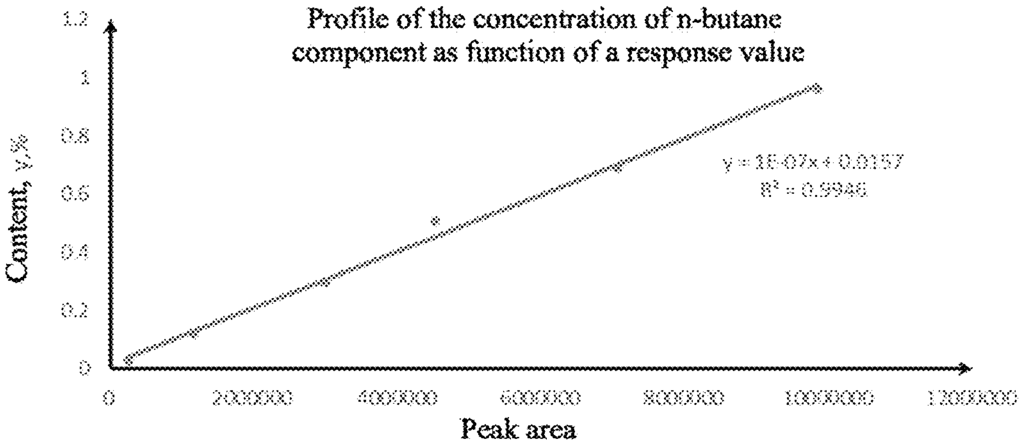
FIG. 33 shows a standard curve of n-butane content.
Figure 34:
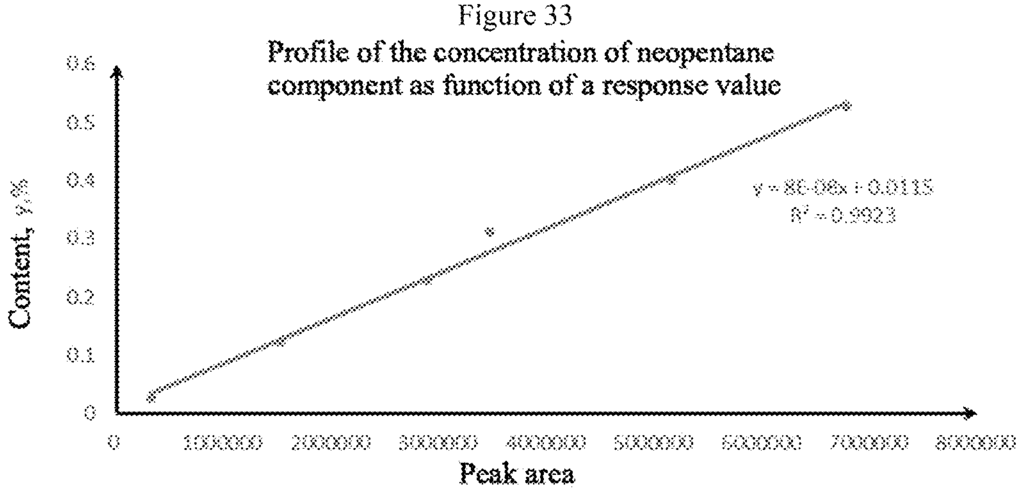
FIG. 34 shows a standard curve of neopentane content.
Figure 35:
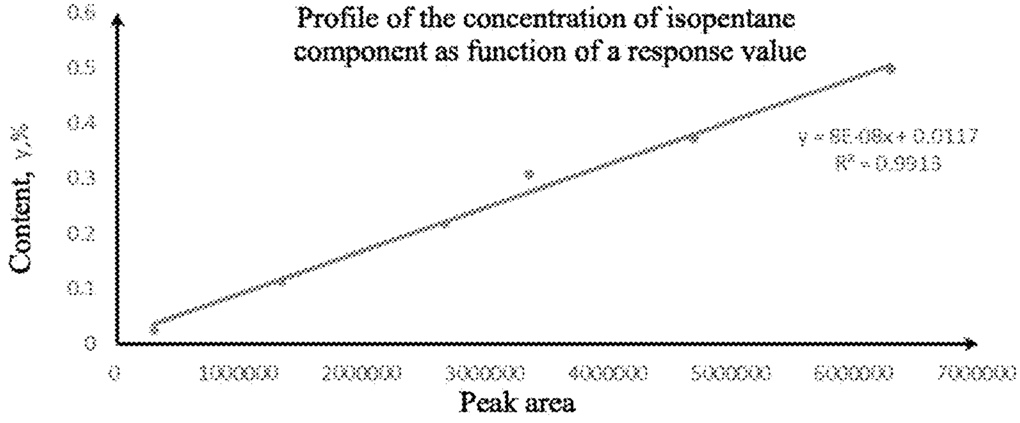
FIG. 35 shows a standard curve of isopentane content.
Figure 36:
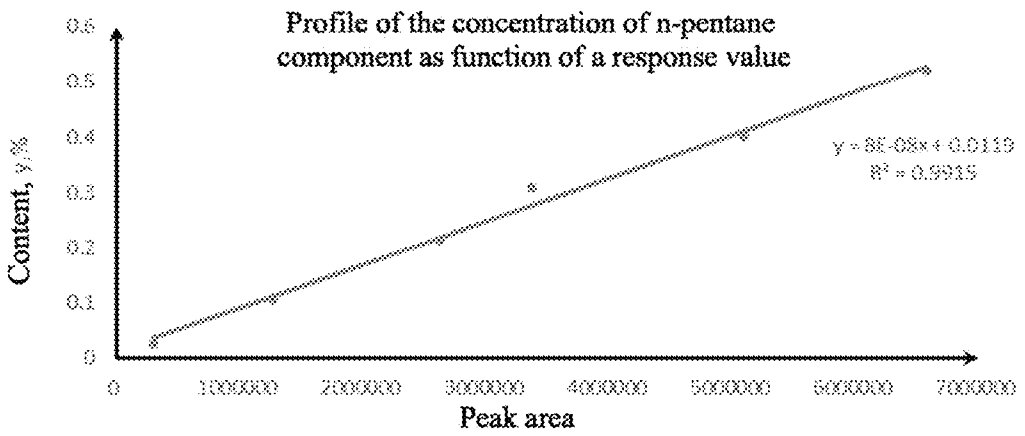
FIG. 36 shows a standard curve of n-pentane content.

In step S6, in the fifth chromatographic column analysis system 25, the fifth carrier gas tube 253 is used to deliver the carrier gas, and the fourth pre-separation column 254 and the fourth chromatographic analytical column 255 are used to perform separation on the natural gas sample in the fifth quantitative tube 252 under the driving of the carrier gas; after carbon dioxide and ethane components in the natural gas sample exit the fourth pre-separation column 254 and enter the fourth chromatographic analytical column 255, the carrier gas is transferred to the outlet end of the fourth pre-separation column 254, and the remaining components in the third pre-separation column 245 are back flushed out of the fifth chromatographic column analysis system 25 under the driving of the carrier gas; and after the back flushing is completed, the carrier gas is transferred to the inlet end of the fourth chromatographic analytical column 255, and under the driving of the carrier gas, the carbon dioxide and ethane components separated by the fourth chromatographic analytical column 255 sequentially enter the second thermal conductivity detector 34 for detection, so as to obtain a fifth detection chromatogram. Specifically, the fifth sample loading valve 251 in the fifth chromatographic column analysis system 25 is switched to the second setting position, the carrier gas is introduced into the fifth chromatographic column analysis system 25 from the fifth carrier gas tube 253 at a pressure of 250 kPa, enters the fifth quantitative tube 252 through the seventh valve port e7 and the eighth valve port e8 in sequence, and drives the natural gas sample in the fifth quantitative tube 252 to flow into the fourth pre-separation column 254 after passing through the first valve port e1 and the second valve port e2 in sequence, so as to be pre-separated in the fourth pre-separation column 254; and carbon dioxide and ethane are sequentially discharged from the fourth pre-separation column 254, and then enter the fourth chromatographic analytical column 255 for further separation after passing through the sixth valve port e6 and the fifth valve port e5 in sequence under the driving of the carrier gas, so that the time difference in separation of the components is increased. After the carbon dioxide and ethane components exist the fourth pre-separation column 254 and enter the fourth chromatographic analytical column 255, the fifth sample loading valve 251 of the third chromatographic column analysis system 23 is switched to the first setting position. The carrier gas is introduced from the fifth carrier gas tube 253 at a pressure of 250 kPa, and enters the fourth pre-separation column 254 from the outlet end of the fourth pre-separation column 254 through the seventh valve port e7 and the sixth valve port e6 in sequence, and the remaining components in the fourth pre-separation column 254 are flushed out of the third chromatographic column analysis system 23. A flow direction of the carrier gas is then adjusted. The carrier gas is introduced from the fifth carrier gas tube 253 at a pressure of 250 kPa, and enters the fourth chromatographic analytical column 255 after passing through the fourth valve port e4 and the fifth valve port e5 in sequence, and the carbon dioxide and ethane sequentially exit the fourth chromatographic analytical column 255 under the driving of the carrier gas and enter the second thermal conductivity detector 34 for detection so as to obtain the fifth detection chromatogram. See FIG. 10 for the fifth detection chromatogram.

The carrier gas is nitrogen.

The column temperature of the second chromatographic analytical column is 60° C.

The temperature of the second thermal conductivity detector 34 is 150° C., and the second thermal conductivity detector 34 has an operating current of 70 mA, and is anodic in polarity.

In step S7, contents of the sulfides in the natural gas sample are determined based on the obtained first detection chromatogram. Specifically, based on the obtained first detection chromatogram, the contents of carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene in the natural gas sample are determined using standard curves of the contents of the sulfides, and the results are shown in Table 1.

Contents of the hydrocarbons having $C_3$ and higher in the natural gas sample are determined based on the obtained second detection chromatogram. Specifically, based on the obtained second detection chromatogram, the contents of propane, isobutane, n-butane, neopentane, isopentane, n-pentane, and $C_6^+$ hydrocarbon components in the natural gas sample are determined using standard curves of the contents of the hydrocarbons having $C_3$ and higher, and the results are shown in Table 2.

Contents of the oxygen, nitrogen, methane and carbon monoxide in the natural gas sample are determined based on the obtained third detection chromatogram. Specifically, based on the obtained third detection chromatogram, the contents of the oxygen, nitrogen, methane and carbon monoxide in the natural gas sample are determined using standard curves of the contents of the oxygen, nitrogen, methane and carbon monoxide, and the results are shown in Table 3.

Contents of the carbon dioxide and ethane in the natural gas sample are determined based on the obtained fourth detection chromatogram. Specifically, based on the obtained fourth detection chromatogram, the contents of the carbon dioxide and ethane in the natural gas samples are determined using standard curves of the contents of the carbon dioxide and ethane, and the results are shown in Table 3.

Contents of the helium and hydrogen in the natural gas sample are determined based on the obtained fifth detection chromatogram. Specifically, based on the obtained fifth detection chromatogram, the contents of the helium and hydrogen in the natural gas sample are determined using standard curves of the contents of the helium and hydrogen, and the results are shown in Table 4.

The standard curves of the contents of the sulfides is obtained in such a way that 7 bottles of standard substances of 4 types of sulfur compounds and 13 types of sulfur compounds at different concentration points are introduced into an instrument for analysis, each bottle of standard substance is repeatedly analyzed for 11 or more times, effective 11-injection component peak area data is collected, the average value of component peak areas during 11 injections is plotted against the corresponding content, and a profile of the concentration of each component as function of a response value is inspected. Calibration curves of 13 types of sulfur compounds are shown in the following Tables 5-17 and FIGS. 11-23.

The standard curves of the contents of the hydrocarbons having $C_3$ and higher, the standard curves of the contents of the oxygen, nitrogen, methane and carbon monoxide, and the standard curves of the contents of the helium and hydrogen are obtained by the same method, and the results are shown in Tables 18-30 and FIGS. 24-36.

TABLE 1

| | Content (ppm) | S/N | LOD (S/N = 3) (ppm) |
|---|---|---|---|
| $H_2S$ | 5.03 | 4167.315329 | 0.004107 |
| COS | 5.02 | 6224.611520 | 0.002739 |
| Methyl mercaptan | 5.01 | 6566.940805 | 0.002607 |
| Ethyl mercaptan | 5.02 | 5970.898393 | 0.002854 |
| Methyl sulfide | 4.98 | 6374.534079 | 0.002667 |
| $CS_2$ | 4.99 | 14033.098416 | 0.001214 |
| Isopropyl mercaptan | 4.97 | 5456.459935 | 0.003098 |
| Tert-butyl mercaptan | 4.98 | 4907.412677 | 0.003449 |
| Methyl ethyl sulfide | 5.09 | 6540.707642 | 0.002655 |
| Thiophene | 5.12 | 7051.172391 | 0.002478 |
| Ethyl sulfide | 4.98 | 6265.610865 | 0.002668 |
| n-butyl mercaptan | 5.01 | 5403.188018 | 0.003151 |
| Dimethyl disulfide | 5.04 | 10803.035573 | 0.001581 |

TABLE 2

| | Content (%) | S/N | LOD (S/N = 3) (%) |
|---|---|---|---|
| n-$C_6H_{14}$ | 0.201 | 17658.493960 | 0.000038 |
| $CH_4$ | 97.207 | 2272939.090391 | 0.000141 |
| $C_2H_6$ | 0.197 | 10094.716574 | 0.000064 |
| $C_3H_8$ | 0.199 | 10645.721892 | 0.000062 |
| i-$C_4H_{10}$ | 0.2 | 10281.417050 | 0.000064 |
| n-$C_4H_{10}$ | 0.2 | 10644.095409 | 0.000062 |
| neo-$C_5H_{12}$ | 0.197 | 8484.621906 | 0.000077 |
| i-$C_5H_{12}$ | 0.2 | 9580.508528 | 0.000069 |
| n-$C_5H_{12}$ | 0.202 | 9284.511168 | 0.000072 |

TABLE 3

| | Content (%) | S/N | LOD (S/N = 3) (%) |
|---|---|---|---|
| $CO_2$ | 0.199 | 3808.073 | 0.000172 |
| $C_2H_6$ | 0.197 | 2833.088 | 0.000229 |
| $O_2$ | 0.2 | 4977.471 | 0.000133 |
| $N_2$ | 0.2 | 3799.549 | 0.000174 |
| $CH_4$ | 97.207 | 411381.3 | 0.000780 |
| CO | 0.199 | 1504.117 | 0.000437 |

TABLE 4

| | Content (%) | S/N | LOD (S/N = 3) (%) |
|---|---|---|---|
| He | 0.199 | 11306.401497 | 0.000058 |
| $H_2$ | 0.2 | 17661.056323 | 0.000037 |

TABLE 5

Corresponding value table of concentration of hydrogen sulfide component and response value

| No. | Peak area | Content, mg/$m^3$ |
|---|---|---|
| 1 | 7755 | 0.995 |
| 2 | 23123 | 3.01 |
| 3 | 35894 | 4.93 |
| 4 | 61473 | 7.05 |
| 5 | 77139 | 10.1 |
| 6 | 113568 | 15 |
| 7 | 145374 | 20.1 |
| 8 | 175204 | 25.2 |
| 9 | 223374 | 29.9 |
| 10 | 257488 | 35 |
| 11 | 293867 | 40.1 |

TABLE 5-continued

Corresponding value table of concentration of hydrogen sulfide component and response value

| No. | Peak area | Content, mg/$m^3$ |
|---|---|---|
| 12 | 318306 | 44.5 |
| 13 | 362401 | 49.9 |

TABLE 6

Corresponding value table of concentration of carbon oxysulfide component and response value

| No. | Peak area | Content, mg/$m^3$ |
|---|---|---|
| 1 | 8603 | 0.996 |
| 2 | 24695 | 3.01 |
| 3 | 37690 | 4.92 |
| 4 | 48431 | 7.06 |
| 5 | 80341 | 10.1 |
| 6 | 109724 | 15 |
| 7 | 148874 | 20.1 |
| 8 | 184133 | 27.7 |
| 9 | 234731 | 29.9 |
| 10 | 271912 | 35.1 |
| 11 | 311048 | 40.2 |
| 12 | 337337 | 44.5 |
| 13 | 378141 | 49.9 |

TABLE 7

Corresponding value table of concentration of methyl mercaptan component and response value

| No. | Peak area | Content, mg/$m^3$ |
|---|---|---|
| 1 | 8364 | 0.992 |
| 2 | 24219 | 3 |
| 3 | 38070 | 4.92 |
| 4 | 49528 | 7.03 |
| 5 | 81729 | 10.1 |
| 6 | 110957 | 15.1 |
| 7 | 144832 | 20.1 |
| 8 | 179477 | 25.3 |
| 9 | 228265 | 29.8 |
| 10 | 262857 | 34.9 |
| 11 | 300462 | 40 |
| 12 | 325956 | 44.4 |
| 13 | 365652 | 49.7 |

TABLE 8

Corresponding value table of concentration of ethyl mercaptan component and response value

| No. | Peak area | Content, mg/$m^3$ |
|---|---|---|
| 1 | 8539 | 0.994 |
| 2 | 24343 | 3 |
| 3 | 37681 | 4.92 |
| 4 | 49182 | 7.04 |
| 5 | 80886 | 10.1 |
| 6 | 111031 | 15 |
| 7 | 145870 | 20.1 |
| 8 | 180016 | 25.2 |
| 9 | 229900 | 29.8 |
| 10 | 263783 | 35 |
| 11 | 302057 | 40.1 |
| 12 | 327803 | 44.4 |
| 13 | 368402 | 49.8 |

TABLE 9

Corresponding value table of concentration of methyl sulfide component and response value

| No. | 1 | 2 | 3 | 4 |
|---|---|---|---|---|
| Peak area | 39105 | 81791 | 110268 | 137852 |
| Content, mg/m$^3$ | 5.1 | 10.2 | 15.2 | 20.2 |

TABLE 10

Corresponding value table of concentration of carbon disulfide component and response value

| No. | 1 | 2 | 3 | 4 |
|---|---|---|---|---|
| Peak area | 40022 | 84178 | 113526 | 141749 |
| Content, mg/m$^3$ | 5.17 | 10.3 | 15.3 | 20.5 |

TABLE 11

Corresponding value table of concentration of isopropyl mercaptan component and response value

| No. | 1 | 2 | 3 | 4 |
|---|---|---|---|---|
| Peak area | 38399 | 80736 | 108164 | 135258 |
| Content, mg/m$^3$ | 5.07 | 10.1 | 15 | 20.1 |

TABLE 12

Corresponding value table of concentration of tert-butyl mercaptan component and response value

| No. | 1 | 2 | 3 | 4 |
|---|---|---|---|---|
| Peak area | 38543 | 80962 | 108250 | 135598 |
| Content, mg/m$^3$ | 5.05 | 10.1 | 15.0 | 20.0 |

TABLE 13

Corresponding value table of concentration of methyl ethyl sulfide component and response value

| No. | 1 | 2 | 3 | 4 |
|---|---|---|---|---|
| Peak area | 37895 | 79999 | 107262 | 134436 |
| Content, mg/m$^3$ | 5.14 | 10.3 | 15.3 | 20.3 |

TABLE 14

Corresponding value table of concentration of thiophene component and response value

| No. | 1 | 2 | 3 | 4 |
|---|---|---|---|---|
| Peak area | 38278 | 80734 | 108777 | 136348 |
| Content, mg/m$^3$ | 5.06 | 10.1 | 15.0 | 20.0 |

TABLE 15

Corresponding value table of concentration of ethyl sulfide component and response value

| No. | 1 | 2 | 3 | 4 |
|---|---|---|---|---|
| Peak area | 38654 | 81228 | 108819 | 136410 |
| Content, mg/m$^3$ | 5.04 | 10.1 | 15.0 | 20.0 |

TABLE 16

Corresponding value table of concentration of n-butyl mercaptan component and response value

| No. | 1 | 2 | 3 | 4 |
|---|---|---|---|---|
| Peak area | 36725 | 77902 | 104555 | 131298 |
| Content, mg/m$^3$ | 5.04 | 10.1 | 15.0 | 20.0 |

TABLE 17

Corresponding value table of concentration of dimethyl disulfide component and response value

| No. | 1 | 2 | 3 | 4 |
|---|---|---|---|---|
| Peak area | 37989 | 79919 | 107123 | 134151 |
| Content, mg/m$^3$ | 4.99 | 10.0 | 15.0 | 20.0 |

TABLE 18

Corresponding value table of concentration of carbon dioxide component and response value

| | No. | | | | | |
|---|---|---|---|---|---|---|
| | 1 | 2 | 3 | 4 | 5 | 6 |
| Peak area | 276 | 2688 | 50784 | 90583 | 131274 | 183647 |
| Reference value of standard substance, y, % | 0.0105 | 0.105 | 1.93 | 3.46 | 5.02 | 7.01 |

TABLE 19

Corresponding value table of concentration of ethane component and response value

| | No. | | | | | |
|---|---|---|---|---|---|---|
| | 1 | 2 | 3 | 4 | 5 | 6 |
| Peak area | 277 | 2688 | 52359 | 97512 | 138525 | 189990 |
| Reference value of standard substance, y, % | 0.0105 | 0.106 | 1.83 | 3.4 | 4.85 | 6.63 |

TABLE 20

Corresponding value table of concentration of nitrogen component and response value

| | No. | | | | | |
|---|---|---|---|---|---|---|
| | 1 | 2 | 3 | 4 | 5 | 6 |
| Peak area | 867 | 5710 | 65424 | 122862 | 207039 | 288884 |
| Reference value of standard substance, y, % | 0.0281 | 0.189 | 1.73 | 3.49 | 5.32 | 7.39 |

TABLE 21

Corresponding value table of concentration of helium component and response value

| No. | 1 | 2 | 3 | 4 |
|---|---|---|---|---|
| Peak area | 1517 | 7540 | 41303 | 72947 |
| Content, $mg/m^3$ | 0.0105 | 0.088 | 0.513 | 0.93 |

TABLE 22

Corresponding value table of concentration of hydrogen component and response value

| No. | 1 | 2 | 3 | 4 |
|---|---|---|---|---|
| Peak area | 1424 | 12544 | 190478 | 370350 |
| Content, $mg/m^3$ | 0.0114 | 0.09 | 1.36 | 2.67 |

TABLE 23

Corresponding value table of concentration of hexane component and response value

| | No. | | | | | |
|---|---|---|---|---|---|---|
| | 1 | 2 | 3 | 4 | 5 | 6 |
| Peak area | 162737 | 1181843 | 1834728 | 2267348 | 3199737 | 3292007 |
| Reference value of standard substance, y, % | 0.013 | 0.0923 | 0.131 | 0.201 | 0.262 | 0.282 |

TABLE 24

Corresponding value table of concentration of propane component and response value

| | No. | | | | | |
|---|---|---|---|---|---|---|
| | 1 | 2 | 3 | 4 | 5 | 6 |
| Peak area | 74514 | 840546 | 6689402 | 12540797 | 18536241 | 25084340 |
| Reference value of standard substance, y, % | 0.0105 | 0.114 | 0.883 | 1.85 | 2.39 | 3.24 |

TABLE 25

Corresponding value table of concentration of carbon monoxide component and response value

| | No. | | | | | |
|---|---|---|---|---|---|---|
| | 1 | 2 | 3 | 4 | 5 | 6 |
| Peak area | 3242 | 8645 | 13585 | 22539 | 27093 | 120340 |
| Reference value of standard substance, y, % | 0.084 | 0.224 | 0.352 | 0.584 | 0.702 | 3.24 |

TABLE 26

Corresponding value table of concentration of isobutane component and response value

| | No. | | | | | |
|---|---|---|---|---|---|---|
| | 1 | 2 | 3 | 4 | 5 | 6 |
| Peak area | 197855 | 1022004 | 3058375 | 4649287 | 7216474 | 9990056 |
| Reference value of standard substance, y, % | 0.0209 | 0.105 | 0.306 | 0.522 | 0.704 | 0.977 |

TABLE 27

Corresponding value table of concentration of n-butane component and response value

| | No. | | | | | |
|---|---|---|---|---|---|---|
| | 1 | 2 | 3 | 4 | 5 | 6 |
| Peak area | 247785 | 1151669 | 2974204 | 4510332 | 7051530 | 9831076 |
| Reference value of standard substance, y, % | 0.0264 | 0.119 | 0.299 | 0.507 | 0.688 | 0.960 |

TABLE 28

Corresponding value table of concentration of neopentane component and response value

| | No. | | | | | |
|---|---|---|---|---|---|---|
| | 1 | 2 | 3 | 4 | 5 | 6 |
| Peak area | 315140 | 1512452 | 2875956 | 3466614 | 5151799 | 6773936 |
| Reference value of standard substance, y, % | 0.0265 | 0.124 | 0.23 | 0.311 | 0.4 | 0.526 |

TABLE 29

Corresponding value table of concentration of isopentane component and response value

| | No. | | | | | |
|---|---|---|---|---|---|---|
| | 1 | 2 | 3 | 4 | 5 | 6 |
| Peak area | 299733 | 1332670 | 2654538 | 3339374 | 4684940 | 6288516 |
| Reference value of standard substance, y, % | 0.0261 | 0.113 | 0.218 | 0.307 | 0.372 | 0.498 |

TABLE 30

Corresponding value table of concentration of n-pentane component and response value

| | No. | | | | | |
|---|---|---|---|---|---|---|
| | 1 | 2 | 3 | 4 | 5 | 6 |
| Peak area | 303535 | 1270585 | 2616985 | 3370006 | 5092523 | 6586821 |
| Reference value of standard substance, y, % | 0.0264 | 0.107 | 0.213 | 0.31 | 0.401 | 0.52 |

In step S8, based on the obtained contents of the sulfides in the natural gas sample, the hydrocarbons having $C_3$ and higher in the natural gas sample, the oxygen, nitrogen, methane and carbon monoxide in the natural gas sample, the carbon dioxide and ethane in the natural gas sample, and the helium and hydrogen in the natural gas sample, determining the natural gas high calorific value, the total sulfur content (in terms of sulfur, in mg/m$^3$), the hydrogen sulfide content (in mg/m$^3$), and the carbon dioxide content (in mole percent).

In the analysis method, as can be seen from FIGS. 7 to 10, the degree of separation of each target component is high, with LOD (S/N=3)<50 ppm. The degrees of separation are all greater than 1, where the degrees of separation of i-$C_4H_1$ and n-$C_4H_{10}$ can reach 4.45, the degrees of separation of $CH_4$ and CO can reach 5.245, and the degrees of separation of $H_2S$ and COS can reach 2.701.

Although the principle and implementations of the present invention are described in the present invention by using specific embodiments, the above description of the embodiments is merely intended to help understand the methods and core concept of the present invention. In addition, for those of ordinary skill in the art, changes may be made to the specific implementations and the scope of application according to the concept of the present invention. In conclusion, the content of the description should not be construed as a limitation to the present invention.

What is claimed is:

1. A device for analyzing quality indicators of a natural gas product, the device comprising a sample loading assembly, and first, second, third, fourth, and fifth chromatographic column analysis systems connected in parallel, wherein the first chromatographic column analysis system is configured for separating sulfides from the natural gas; the second chromatographic column analysis system is configured for separating hydrocarbons having $C_3$ and higher from the natural gas; the third chromatographic column analysis system is configured for separating oxygen, nitrogen, methane, and carbon monoxide from the natural gas; the fourth chromatographic column analysis system is configured for separating carbon dioxide and ethane from the natural gas; and the fifth chromatographic column analysis system is configured for separating helium and hydrogen from the natural gas; wherein each chromatographic column analysis system is provided with a quantitative tube, a carrier gas tube, and a chromatographic column, the quantitative tube is configured for storing a natural gas sample, and the carrier gas tube is configured for delivering a carrier gas to the chromatographic column analysis system to subject the natural gas sample in the quantitative tube to a component separation within the chromatographic column;

the sample loading assembly is connected to the quantitative tubes of the first, second, third, fourth, and fifth chromatographic column analysis systems in a connection/disconnection controllable manner to provide the natural gas sample to the quantitative tubes of the first, second, third, fourth, and fifth chromatographic column analysis systems; and each chromatographic column analysis system is connected to a corresponding detector, respectively.

2. The device according to claim 1, wherein the sample loading assembly is connected to the quantitative tubes of the first, second, third, fourth, and fifth chromatographic column analysis systems such that the quantitative tubes of the first, second, third, fourth, and fifth chromatographic column analysis systems are connected in series;

wherein the sample loading assembly comprises a natural gas intake tube, a natural gas discharge tube, and first, second, third and fourth quantitative tube connecting tubes, the first, second, third and fourth quantitative tube connecting tubes are configured for connecting the quantitative tubes in series respectively, the natural gas intake tube is connected to an inlet end of the quantitative tubes connected in series, and the natural gas discharge tube is connected to an outlet end of the quantitative tubes connected in series.

3. The device according to claim 1, wherein the chromatographic column of the first chromatographic column analysis system comprises a sulfur column; in the first chromatographic column analysis system, one end of the quantitative tube is connected to the carrier gas tube via a connection/disconnection controllable connecting tubing, the other end of the quantitative tube is connected to an inlet end of the sulfur column via a connection/disconnection controllable connecting tubing, and an outlet end of the sulfur column is connected to the sulfur chemiluminescence detector via a connection/disconnection controllable connecting tubing; wherein the sulfur column enables separation of carbon oxysulfide, hydrogen sulfide, methyl mercaptan, ethyl mercaptan, methyl sulfide, methyl ethyl sulfide, dimethyl disulfide, ethyl sulfide, carbon disulfide, n-butyl mercaptan, tert-butyl mercaptan, isopropyl mercaptan, and thiophene;

the chromatographic column of the second chromatographic column analysis system comprises a first pre-separation column and a first chromatographic analytical column; in the second chromatographic column analysis system, one end of the quantitative tube is connected to the carrier gas tube via a connection/disconnection controllable connecting tubing, the other end of the quantitative tube is connected to an inlet end of the first pre-separation column via a connection/disconnection controllable connecting tubing, an outlet end of the first pre-separation column is connected to an inlet end of the first chromatographic analytical column via a connection/disconnection controllable connecting tubing, the carrier gas tube is connected to the outlet end of the first pre-separation column and the inlet end of the first chromatographic analytical column respectively via a connection/disconnection controllable connecting tubing, and the inlet end of the first pre-separation column and an outlet end of the first chromatographic analytical column are connected to the hydrogen flame ionization detector respectively via a connection/disconnection controllable connecting tubing; wherein the first pre-separation column enables separation of $C_6^+$ hydrocarbon components from $C_5^-$ hydrocarbon components; and the first chromatographic analytical column enables separation of propane, isobutane, n-butane, neopentane, isopentane, and n-pentane;

the chromatographic column of the third chromatographic column analysis system comprises a second pre-separation column and a second chromatographic analytical column; in the third chromatographic column analysis system, one end of the quantitative tube is connected to the carrier gas tube via a connection/disconnection controllable connecting tubing, the other end of the quantitative tube is connected to an inlet end of the second pre-separation column via a connection/disconnection controllable connecting tubing, an outlet end of the second pre-separation column is connected to an inlet end of the second chromatographic analytical column via a connection/disconnection controllable connecting tubing, the carrier gas tube is connected to the outlet end of the second pre-separation column and the inlet end of the second chromatographic analytical column respectively via a connection/disconnection controllable connecting tubing, and an outlet end of the second chromatographic analytical column is connected to the thermal conductivity cell detector via a connection/disconnection controllable connecting tubing; wherein the second pre-separation column enables separation of oxygen, nitrogen, methane, and carbon monoxide from the natural gas; and the second chromatographic analytical column enables separation of oxygen, nitrogen, methane, and carbon monoxide;

the chromatographic column of the fourth chromatographic column analysis system comprises a third pre-separation column and a third chromatographic analytical column; in the fourth chromatographic column analysis system, one end of the quantitative tube is connected to the carrier gas tube via a connection/disconnection controllable connecting tubing, the other end of the quantitative tube is connected to an inlet end of the third pre-separation column via a connection/disconnection controllable connecting tubing, an outlet end of the third pre-separation column is connected to an inlet end of the third chromatographic analytical column via a connection/disconnection controllable connecting tubing, the carrier gas tube is connected to the outlet end of the third pre-separation column and the inlet end of the third chromatographic analytical column respectively via a connection/disconnection controllable connecting tubing, and an outlet end of the third chromatographic analytical column is connected to the thermal conductivity cell detector via a connection/disconnection controllable connecting tubing; wherein the third pre-separation column enables separation of ethane and carbon dioxide from the natural gas; and the third chromatographic analytical column enables separation of ethane and carbon dioxide;

the chromatographic column of the fifth chromatographic column analysis system comprises a fourth pre-separation column and a fourth chromatographic analytical column; in the fifth chromatographic column analysis system, one end of the quantitative tube is connected to the carrier gas tube via a connection/disconnection controllable connecting tubing, the other end of the quantitative tube is connected to an inlet end of the fourth pre-separation column via a connection/disconnection controllable connecting tubing, an outlet end of the fourth pre-separation column is connected to an inlet end of the fourth chromatographic analytical column via a connection/disconnection controllable connecting tubing, the carrier gas tube is connected to the outlet end of the fourth pre-separation column and the inlet end of the fourth chromatographic analytical column respectively via a connection/disconnection controllable connecting tubing, and an outlet end of the fourth chromatographic analytical column is connected to the thermal conductivity cell detector via a connection/disconnection controllable connecting tubing; wherein the fourth pre-separation column enables separation of helium and hydrogen from the natural gas; and the fourth chromatographic analytical column enables separation of helium and hydrogen.

4. The device according to claim 3, wherein the sulfur column is a DB-Sulfur SCD chromatographic column; the DB-Sulfur SCD chromatographic column has a length of 50 m to 60 m;

the first pre-separation column is selected from one of an OV-1 pre-separation column and a DB-1 capillary column; the OV-1 pre-separation column has a length of 1.0 to 2.0 m; the DB-1 capillary column has a length of 3.0 to 5.0 m;

the first chromatographic analytical column is selected from one of an HP-AI/S chromatographic column, an HP-PLOT $Al_2O_3S$ capillary column, a PONA capillary column and a plot Q capillary column; the HP-Al/S chromatographic column has a length of 30 m to 50 m; the HP-PLOT $Al_2O_3$ S capillary column has a length of 25 m to 50 m; he PONA capillary column has a length of 50 m to 100 m; the plot Q capillary column has a length of 25 m to 30 m;

the second pre-separation column is selected from one of a Porapak N column, a Porapak Q column and a Porapak QS column; the Porapak N column has a length of 3 m to 5 m;

the second chromatographic analytical column is an MS-13X molecular sieve column; the MS-13X molecular sieve column has a length of 3.0 m to 5.0 m;

the third pre-separation column is selected from one of a Porapak N column, a Porapak Q column and a Porapak QS column; the Porapak N column has a length of 1 m to 2 m;

the third chromatographic analytical column is selected from one of a Porapak N column, a Porapak Q column and a Porapak QS column; the Porapak N column has a length of 2 m to 3 m;

the fourth pre-separation column is selected from one of a Porapak N column, a Porapak Q column and a Porapak QS column; the Porapak N column has a length of 1 m to 2 m;

the fourth chromatographic analytical column is an MS-5 A molecular sieve column; the MS-5 A molecular sieve column has a length of 3.0 m to 5.0 m.

5. The device according to claim 3, wherein the first chromatographic column analysis system comprises a first sample loading valve which is a multi-way valve having a first setting position and a second setting position; in the first chromatographic column analysis system, the first sample loading valve is connected to two ends of the quantitative tube, the carrier gas tube and the chromatographic column, respectively, and the first sample loading valve is used to control the connection/disconnection of the connecting tubing between the parts of the first chromatographic column analysis system and the connection/disconnection of the connecting tubing between the sample loading assembly and the first chromatographic column analysis system;

when the first sample loading valve is switched to the first setting position, a gas in the sample loading assembly is enabled to be directly discharged from the first chromatographic column analysis system after passing through the quantitative tube; and when the first sample loading valve is switched to the second setting position, a gas in the carrier gas tube of the first chromatographic column analysis system is enabled to flow into the chromatographic column of the first chromatographic column analysis system through the quantitative tube of the first chromatographic column analysis system.

6. The device according to claim 5, wherein the first sample loading valve is a six-way valve having a first setting position and a second setting position, the six-way valve being provided with a first valve port, a second valve port, a third valve port, a fourth valve port, a fifth valve port, and a sixth valve port in clockwise sequence; when the six-way valve is in the first setting position, the sixth valve port is connected to the first valve port, the second valve port is connected to the third valve port, and the fourth valve port is connected to the fifth valve port; when the six-way valve is in the second setting position, the first valve port is connected to the second valve port, the third valve port is connected to the fourth valve port, and the fifth valve port is connected to the sixth valve port; and the sixth valve port and the fifth valve port of the first sample loading valve are each connected to the sample loading assembly, the quantitative tube of the first chromatographic column analysis system has one end connected to the first valve port of the first sample loading valve and the other end connected to the fourth valve port of the first sample loading valve, the carrier gas tube of the first chromatographic column analysis system is connected to the second valve port of the first sample loading valve, and the sulfur column is connected to the third valve port of the first sample loading valve.

7. The device according to claim 3, wherein the second chromatographic column analysis system comprises a second sample loading valve which is a multi-way valve having a first setting position and a second setting position; in the second chromatographic column analysis system, the second sample loading valve is connected to two ends of the quantitative tube, the carrier gas tube, two ends of the first pre-separation column, the inlet end of the first chromatographic analytical column, and the hydrogen flame ionization detector, respectively, and the second sample loading valve is used to control the connection/disconnection of the connecting tubing between the parts of the second chromatographic column analysis system and the connection/disconnection of the connecting tubing between the sample loading assembly and the second chromatographic column analysis system;

when the second sample loading valve is switched to the first setting position, a gas in the sample loading assembly is enabled to be directly discharged from the second chromatographic column analysis system after passing through the quantitative tube, a gas in the carrier gas tube of the second chromatographic column analysis system is enabled to enter the outlet end of the first pre-separation column, flow out from the inlet end of the first pre-separation column and then flow into the hydrogen flame ionization detector, and the gas in the carrier gas tube of the second chromatographic column analysis system is enabled to enter the first chromatographic analytical column through the inlet end of the first chromatographic analytical column; and when the second sample loading valve is switched to the second setting position, the gas in the carrier gas tube of the second chromatographic column analysis system is enabled to flow to the first pre-separation column through the quantitative tube of the second chromatographic column analysis system, enter into the inlet end of the first pre-separation column and flow out from the outlet end of the first pre-separation column, and then enter the first chromatographic analytical column through the inlet end of the first chromatographic analytical column.

8. The device according to claim 7, wherein the second sample loading valve is a ten-way valve having a first setting position and a second setting position, the second sample loading valve being provided with a first valve port, a second valve port, a third valve port, a fourth valve port, a fifth valve port, a sixth valve port, a seventh valve port, an eighth valve port, a ninth valve port, and a tenth valve port in clockwise sequence; when the second sample loading valve is in the first setting position, the tenth valve port is connected to the first valve port, the second valve port is connected to the third valve port, the fourth valve port is connected to the fifth valve port, the sixth valve port is connected to the seventh valve port, and the eighth valve port is connected to the ninth valve port; when the second sample loading valve is in the second setting position, the first valve port is connected to the second valve port, the third valve port is connected to the fourth valve port, the fifth valve port is connected to the sixth valve port, the seventh valve port is connected to the eighth valve port, and the ninth valve port is connected to the tenth valve port; and the tenth valve port and the ninth valve port of the second sample loading valve are each connected to the sample loading assembly, the quantitative tube of the second chromatographic column analysis system has one end connected to the first valve port of the second sample loading valve and the other end connected to the eighth valve port of the second sample loading valve, the carrier gas tube of the second chromatographic column analysis system is connected to each of the seventh valve port and the fourth valve port of the second sample loading valve, the first pre-separation column has the inlet end connected to the second valve port of the second sample loading valve and the outlet end connected to the sixth valve port of the second sample loading valve, the inlet end of the first chromatographic analytical column is connected to the fifth valve port of the second sample loading valve, and the third valve port of the second sample loading valve is connected to the hydrogen flame detector.

9. The device according to claim 3, wherein the third chromatographic column analysis system comprises a third sample loading valve which is a multi-way valve having a first setting position and a second setting position; in the third chromatographic column analysis system, the third sample loading valve is connected to two ends of the quantitative tube, the carrier gas tube, two ends of the second pre-separation column, and the inlet end of the second chromatographic analytical column, respectively, and the third sample loading valve is used to control the connection/disconnection of the connecting tubing between the parts of the third chromatographic column analysis system and the connection/disconnection of the connecting tubing between the sample loading assembly and the third chromatographic column analysis system;

when the third sample loading valve is switched to the first setting position, a gas in the sample loading assembly is enabled to be directly discharged from the third chromatographic column analysis system after passing through the quantitative tube, a gas in the carrier gas tube of the third chromatographic column analysis system is enabled to enter into the outlet end of the second pre-separation column and flow out from the inlet end of the second pre-separation column so as to be discharged from the three analysis systems, and the gas in the carrier gas tube of the third chromatographic column analysis system is enabled to enter the second chromatographic analytical column through the inlet end of the second chromatographic analytical column; and when the third sample loading valve is switched to the second setting position, the gas in the carrier gas tube of the third chromatographic column analysis system is enabled to flow to the second pre-separation column through the quantitative tube of the third chromatographic column analysis system, enter the inlet end of the second pre-separation column and flow out from the outlet end of the second pre-separation column, and then enter the second chromatographic analytical column through the inlet end of the second chromatographic analytical column.

10. The device according to claim 9, wherein the third sample loading valve is a ten-way valve having a first setting position and a second setting position, the third sample loading valve being provided with a first valve port, a second valve port, a third valve port, a fourth valve port, a fifth valve port, a sixth valve port, a seventh valve port, an eighth valve port, a ninth valve port, and a tenth valve port in clockwise sequence; when the third sample loading valve is in the first setting position, the tenth valve port is connected to the first valve port, the second valve port is connected to the third valve port, the fourth valve port is connected to the fifth valve port, the sixth valve port is connected to the seventh valve port, and the eighth valve port is connected to the ninth valve port; when the third sample loading valve is in the second setting position, the first valve port is connected to the second valve port, the third valve port is connected to the fourth valve port, the fifth valve port is connected to the sixth valve port, the seventh valve port is connected to the eighth valve port, and the ninth valve port is connected to the tenth valve port; and the tenth valve port and the ninth valve port of the third sample loading valve are each connected to the sample loading assembly, the quantitative tube of the third chromatographic column analysis system has one end connected to the first valve port of the third sample loading valve and the other end connected to the eighth valve port of the third sample loading valve, the carrier gas tube of the third chromatographic column analysis system is connected to the seventh valve port and the fourth valve port of the third sample loading valve, the second pre-separation column has the inlet end connected to the second valve port of the third sample loading valve and the outlet end connected to the sixth valve port of the third sample loading valve, and the inlet end of the second chromatographic analytical column is connected to the fifth valve port of the third sample loading valve.

11. The device according to claim 3, wherein the fourth chromatographic column analysis system comprises a fourth sample loading valve which is a multi-way valve having a first setting position and a second setting position; in the fourth chromatographic column analysis system, the fourth sample loading valve is connected to two ends of the quantitative tube, the carrier gas tube, two ends of the third pre-separation column, and the inlet end of the third chromatographic analytical column, respectively, and the fourth sample loading valve is used to control the connection/disconnection of the connecting tubing between the parts of the fourth chromatographic column analysis system and the connection/disconnection of the connecting tubing between the sample loading assembly and the fourth chromatographic column analysis system;

when the fourth sample loading valve is switched to the first setting position, a gas in the sample loading assembly is enabled to be directly discharged from the fourth chromatographic column analysis system after passing through the quantitative tube, a gas in the carrier gas tube of the fourth chromatographic column analysis system is enabled to enter into the outlet end of the third pre-separation column and flow out from the inlet end of the third pre-separation column so as to be discharged from the three analysis systems, and the gas in the carrier gas tube of the fourth chromatographic column analysis system is enabled to enter the third chromatographic analytical column through the inlet end of the third chromatographic analytical column; and when the fourth sample loading valve is switched to the second setting position, the gas in the carrier gas tube of the fourth chromatographic column analysis system is enabled to flow to the third pre-separation column through the quantitative tube of the fourth chromatographic column analysis system, enter into the inlet end of the third pre-separation column and flow out from the outlet end of the third pre-separation column, and then enter the third chromatographic analytical column through the inlet end of the third chromatographic analytical column.

12. The device according to claim 11, wherein the fourth sample loading valve is a ten-way valve having a first setting position and a second setting position, the fourth sample loading valve being provided with a first valve port, a second valve port, a third valve port, a fourth valve port, a fifth valve port, a sixth valve port, a seventh valve port, an eighth valve port, a ninth valve port, and a tenth valve port in clockwise sequence; when the fourth sample loading valve is in the first setting position, the tenth valve port is connected to the first valve port, the second valve port is connected to the third valve port, the fourth valve port is connected to the fifth valve port, the sixth valve port is connected to the seventh valve port, and the eighth valve port is connected to the ninth valve port; when the fourth sample loading valve is in the second setting position, the first valve port is connected to the second valve port, the third valve port is connected to the fourth valve port, the fifth valve port is connected to the sixth valve port, the seventh valve port is connected to the eighth valve port, and the ninth valve port is connected to the tenth valve port; and the tenth valve port and the ninth valve port of the fourth sample loading valve are each connected to the sample loading assembly, the quantitative tube of the fourth chromatographic column analysis system has one end connected to the first valve port of the fourth sample loading valve and the other end connected to the eighth valve port of the fourth sample loading valve, the carrier gas tube of the fourth chromatographic column analysis system is connected to the seventh valve port and the fourth valve port of the fourth sample loading valve, the third pre-separation column has the inlet end connected to the second valve port of the fourth sample loading valve and the outlet end connected to the sixth valve port of the fourth sample loading valve, and the inlet end of the third chromatographic analytical column is connected to the fifth valve port of the fourth sample loading valve.

13. The device according to claim 3, wherein the fifth chromatographic column analysis system comprises a fifth sample loading valve which is a multi-way valve comprising a first setting position and a second setting position; in the fifth chromatographic column analysis system, the fifth sample loading valve is connected to two ends of the quantitative tube, the carrier gas tube, two ends of the fourth pre-separation column, and the inlet end of the fourth chromatographic analytical column, respectively, and the fifth sample loading valve is used to control the connection/disconnection of the connecting tubing between the parts of the fifth chromatographic column analysis system and the connection/disconnection of the connecting tubing between the sample loading assembly and the fifth chromatographic column analysis system;

when the fifth sample loading valve is switched to the first setting position, a gas in the sample loading assembly is enabled to be directly discharged from the fifth chromatographic column analysis system after passing through the quantitative tube, a gas in the carrier gas tube of the fifth chromatographic column analysis system is enabled to enter into the outlet end of the fourth pre-separation column and flow out from the inlet end of the fourth pre-separation column so as to be discharged from the three analysis systems, and the gas in the carrier gas tube of the fifth chromatographic column analysis system is enabled to enter the fourth chromatographic analytical column through the inlet end of the fourth chromatographic analytical column; and when the fifth sample loading valve is switched to the second setting position, the gas in the carrier gas tube of the fifth chromatographic column analysis system is enabled to flow to the fourth pre-separation column through the quantitative tube of the fifth chromatographic column analysis system, enter into the inlet end of the fourth pre-separation column and flow out from the outlet end of the fourth pre-separation column, and then enter the fourth chromatographic analytical column through the inlet end of the fourth chromatographic analytical column.

14. The device according to claim 13, wherein the fifth sample loading valve is a ten-way valve having a first setting position and a second setting position, the fifth sample loading valve being provided with a first valve port, a second valve port, a third valve port, a fourth valve port, a fifth valve port, a sixth valve port, a seventh valve port, an eighth valve port, a ninth valve port, and a tenth valve port in clockwise sequence; when the fifth sample loading valve is in the first setting position, the tenth valve port is connected to the first valve port, the second valve port is connected to the third valve port, the fourth valve port is connected to the fifth valve port, the sixth valve port is connected to the seventh valve port, and the eighth valve port is connected to the ninth valve port; when the fifth sample loading valve is in the second setting position, the first valve port is connected to the second valve port, the third valve port is connected to the fourth valve port, the fifth valve port is connected to the sixth valve port, the seventh valve port is connected to the eighth valve port, and the ninth valve port is connected to the tenth valve port; and the tenth valve port and the ninth valve port of the fifth sample loading valve are each connected to the sample loading assembly, the quantitative tube of the fifth chromatographic column analysis system has one end connected to the first valve port of the fifth sample loading valve and the other end connected to the eighth valve port of the fifth sample loading valve, the carrier gas tube of the fifth chromatographic column analysis system is connected to the seventh valve port and the fourth valve port of the fifth sample loading valve, the fourth pre-separation column has the inlet end connected to the second valve port of the fifth sample loading valve and the outlet end connected to the sixth valve port of the fifth sample loading valve, and the inlet end of the fourth chromatographic analytical column is connected to the fifth valve port of the fifth sample loading valve.

15. A method for analyzing quality indicators of a natural gas product, the method being implemented using a device for analyzing quality indicators of a natural gas product according to any one of claim 1, wherein the method comprises:

loading a sample into the quantitative tubes of the first chromatographic column analysis system, the second chromatographic column analysis system, the third chromatographic column analysis system, the fourth chromatographic column analysis system, and the fifth chromatographic column analysis system such that each of the quantitative tubes is filled with a natural gas sample;

in the first chromatographic column analysis system, using the carrier gas tube to deliver a carrier gas, using the chromatographic column to separate sulfides from the natural gas sample in the quantitative tube under the driving of the carrier gas, and delivering the separated components to a detector for detection to obtain a first detection chromatogram; determining contents of the sulfides in the natural gas sample based on the obtained first detection chromatogram;

in the second chromatographic column analysis system, using the carrier gas tube to deliver a carrier gas, using the chromatographic column to separate hydrocarbons having $C_3$ and higher from the natural gas sample in the quantitative tube under the driving of the carrier gas, and delivering the separated components to a detector for detection to obtain a second detection chromatogram; determining contents of the hydrocarbons having $C_3$ and higher in the natural gas sample based on the obtained second detection chromatogram;

in the third chromatographic column analysis system, using the carrier gas tube to deliver a carrier gas, using the chromatographic column to separate oxygen, nitrogen, methane, and carbon monoxide from the natural gas sample in the quantitative tube under the driving of the carrier gas, and delivering the separated components to a detector for detection to obtain a third detection chromatogram; determining contents of the oxygen, nitrogen, methane and carbon monoxide in the natural gas sample based on the obtained third detection chromatogram;

in the fourth chromatographic column analysis system, using the carrier gas tube to deliver a carrier gas, using the chromatographic column to separate carbon dioxide and ethane from the natural gas sample in the quantitative tube under the driving of the carrier gas, and delivering the separated components to a detector for detection to obtain a fourth detection chromatogram; determining contents of the carbon dioxide and ethane in the natural gas sample based on the obtained fourth detection chromatogram;

in the fifth chromatographic column analysis system, using the carrier gas tube to deliver a carrier gas, using the chromatographic column to separate helium and hydrogen from the natural gas sample in the quantitative tube under the driving of the carrier gas, and delivering the separated components to a detector for detection to obtain a fifth detection chromatogram; determining contents of the helium and hydrogen in the natural gas sample based on the obtained fifth detection chromatogram; and based on the obtained contents of the sulfides in the natural gas sample, contents of the hydrocarbons having $C_3$ and higher in the natural gas sample, contents of the oxygen, nitrogen, methane and carbon monoxide in the natural gas sample, contents of the carbon dioxide and ethane in the natural gas sample, and contents of the helium and hydrogen in the natural gas sample, determining a high calorific value, a total sulfur content, a hydrogen sulfide content, and/or a carbon dioxide content for the natural gas.

16. The method according to claim 15, wherein the step of, in the first chromatographic column analysis system, using the carrier gas tube to deliver a carrier gas, using the chromatographic column to separate sulfides from the natural gas sample in the quantitative tube under the driving of the carrier gas, and delivering the separated components to a detector for detection to obtain a first detection chromatogram comprises:

in the first chromatographic column analysis system, using the carrier gas tube to deliver the carrier gas, delivering the natural gas sample in the quantitative tube to the sulfur column under the driving of the carrier gas to separate the sulfides, and delivering the separated components to a sulfur chemiluminescence detector such that the sulfides in the natural gas sample are detected so as to obtain the first detection chromatogram;

the sulfur column is maintained at 30-50° C. until carbonyl sulfur exits the sulfur column, and the temperature of the sulfur column is then raised at a rate of 10-20° C./min to, and maintained at, 130° C.

17. The method according to claim 15, wherein the step of, in the second chromatographic column analysis system, using the carrier gas tube to deliver a carrier gas, using the chromatographic column to separate hydrocarbons having $C_3$ and higher from the natural gas sample in the quantitative tube under the driving of the carrier gas, and delivering the separated components to a detector for detection to obtain a second detection chromatogram comprises:

in the second chromatographic column analysis system, using the carrier gas tube to deliver the carrier gas, and subjecting the natural gas sample in the quantitative tube under the driving of the carrier gas to separations using the first pre-separation column and the first chromatographic analytical column in sequence; after $C_5^-$ components in the natural gas sample exit the first pre-separation column and enter the first chromatographic analytical column, transferring the carrier gas to the outlet end of the first pre-separation column, connecting the inlet end of the first pre-separation column to the hydrogen flame detector, and under the driving of the carrier gas, back flushing $C_6^+$ hydrocarbon components from the first pre-separation column to a hydrogen flame detector for detection; and after the back flushing is completed, transferring the carrier gas to the inlet end of the first chromatographic analytical column, and under the driving of the carrier gas, sequentially introducing individual $C_3$ hydrocarbon components separated by the first chromatographic analytical column into the hydrogen flame detector for detection, so as to obtain the second detection chromatogram;

the first chromatographic analytical column is maintained at 30-50° C. until the hydrogen flame detector monitors peaks of the $C_6^+$ hydrocarbon components, and the temperature of the first chromatographic analytical column is then raised at a rate of 10-20° C./min to, and maintained at, 130° C.

18. The method according to claim 15, wherein the step of, in the third chromatographic column analysis system, using the carrier gas tube to deliver a carrier gas, using the chromatographic column to separate oxygen, nitrogen, methane, and carbon monoxide from the natural gas sample in the quantitative tube under the driving of the carrier gas, and delivering the separated components to a detector for detection to obtain a third detection chromatogram comprises:

in the third chromatographic column analysis system, using the carrier gas tube to deliver the carrier gas, and subjecting the natural gas sample in the quantitative tube under the driving of the carrier gas to separations using the second pre-separation column and the second chromatographic analytical column in sequence; after the oxygen, nitrogen, methane and carbon monoxide components in the natural gas sample exit the second pre-separation column and enter the second chromatographic analytical column, transferring the carrier gas to the outlet end of the second pre-separation column, and back flushing the remaining components in the second pre-separation column out of the third chromatographic column analysis system under the driving of the carrier gas; and after the back flushing is completed, transferring the carrier gas to the inlet end of the second chromatographic analytical column, and under the driving force of the carrier gas, sequentially introducing the oxygen, nitrogen, methane and carbon monoxide components separated by the second chromatographic analytical column into the thermal conductivity cell detector for detection, so as to obtain the third detection chromatogram;

the column temperature of the second chromatographic analytical column is 50-70° C.

19. The method according to claim 15, wherein the step of, in the fourth chromatographic column analysis system, using the carrier gas tube to deliver a carrier gas, using the chromatographic column to separate carbon dioxide and ethane from the natural gas sample in the quantitative tube under the driving of the carrier gas, and delivering the separated components to a detector for detection to obtain a fourth detection chromatogram comprises:

in the fourth chromatographic column analysis system, using the carrier gas tube to deliver the carrier gas, and subjecting the natural gas sample in the quantitative tube under the driving of the carrier gas to separations using the third pre-separation column and the third chromatographic analytical column in sequence; after the carbon dioxide and ethane components in the natural gas sample exit the third pre-separation column and enter the third chromatographic analytical column, transferring the carrier gas to the outlet end of the third pre-separation column, and back flushing the remaining components in the third pre-separation column out of the fourth chromatographic column analysis system under the driving of the carrier gas; and after the back flushing is completed, transferring the carrier gas to the inlet end of the third chromatographic analytical column, and under the driving of the carrier gas, sequentially introducing the carbon dioxide and ethane components separated by the third chromatographic analytical column into the thermal conductivity cell detector for detection, so as to obtain the fourth detection chromatogram.

20. The method according to claim 15, wherein the step of, in the fifth chromatographic column analysis system, using the carrier gas tube to deliver a carrier gas, using the chromatographic column to separate helium and hydrogen from the natural gas sample in the quantitative tube under the driving of the carrier gas, and delivering the separated components to a detector for detection to obtain a fifth detection chromatogram comprises:

in the fifth chromatographic column analysis system, using the carrier gas tube to deliver the carrier gas, and subjecting the natural gas sample in the quantitative tube under the driving of the carrier gas to separations using the fourth pre-separation column and the fourth chromatographic analytical column in sequence; after the helium and hydrogen components in the natural gas sample exit the fourth pre-separation column and enter the fourth chromatographic analytical column, transferring the carrier gas to the outlet end of the fourth pre-separation column, and back flushing the remaining components in the fourth pre-separation column out of the fifth chromatographic column analysis system under the driving of the carrier gas; and after the back flushing is completed, transferring the carrier gas to the inlet end of the fourth chromatographic analytical column, and under the driving of the carrier gas, sequentially introducing the helium and hydrogen components separated by the fourth chromatographic analytical column into the thermal conductivity cell detector for detection, so as to obtain the fifth detection chromatogram.

* * * * *